United States Patent
Gordon

(10) Patent No.: US 9,624,532 B2
(45) Date of Patent: Apr. 18, 2017

(54) ULTRA-SENSITIVE DETECTION OF EXTREMELY LOW LEVEL BIOLOGICAL ANALYTES USING ELECTROCHEMICAL SIGNAL AMPLIFICATION AND BIOSENSOR

(71) Applicant: Neil Gordon, Hampstead (CA)

(72) Inventor: Neil Gordon, Hampstead (CA)

( * ) Notice: Subject to any disclaimer, the term of this patent is extended or adjusted under 35 U.S.C. 154(b) by 593 days.

(21) Appl. No.: 14/173,064

(22) Filed: Feb. 5, 2014

(65) Prior Publication Data

US 2015/0141272 A1    May 21, 2015

Related U.S. Application Data

(60) Provisional application No. 61/760,848, filed on Feb. 5, 2013.

(51) Int. Cl.
   *G01N 27/28*     (2006.01)
   *C12Q 1/68*      (2006.01)

(52) U.S. Cl.
   CPC ........... *C12Q 1/682* (2013.01); *C12Q 1/6804* (2013.01); *C12Q 1/6825* (2013.01)

(58) Field of Classification Search
   CPC .... C12Q 1/6804; C12Q 1/6825; C12Q 1/682; C12Q 2563/113; C12Q 2563/143; C12Q 2563/149; C12Q 2565/102; C12Q 2565/607; C12Q 2565/629
   See application file for complete search history.

(56) References Cited

U.S. PATENT DOCUMENTS

| | | | |
|---|---|---|---|
| 5,514,253 A | 5/1996 | Davis et al. |
| 6,027,886 A | 2/2000 | Leying et al. |
| 6,083,763 A | 7/2000 | Balch |
| 7,682,789 B2 | 3/2010 | Chen et al. |
| 7,852,470 B2 | 12/2010 | Burrell et al. |
| 7,939,734 B1 | 5/2011 | Li et al. |

(Continued)

OTHER PUBLICATIONS

U.S. Appl. No. 03/134,267-A1, filed Aug. 2003, Kang, et al.

(Continued)

*Primary Examiner* — Gurpreet Kaur

(57) ABSTRACT

This invention allows ultra-low levels of virtually any biological analyte to be detected and quantified rapidly, simply and inexpensively with an electrochemical biosensor using a novel electrochemical signal amplification technique. The invention amplifies detection signals from low level analytes using an innovative sandwich ELISA structure that replaces optical labels with a massive amount of electrochemically detectable guanine rich oligonucleotide tags. Selective binding is achieved with matched pairs of either commercial or custom analyte binding materials such as monoclonal antibodies or single strand DNA. The guanine tags are eluted from the sandwich structures and hybridize with complementary cytosine rich oligonucleotide recognition probes attached to the surface of a biosensor working electrode. An electrochemical technique generates a signal in proportion to the guanine level on the working electrode which is also proportional to the analyte level in the sample. Magnetic separation and a nanosensor are used to improve the signal-to-noise ratio for measuring analyte levels 1,000,000 times lower than enzyme-linked immunosorbent assay (ELISA).

20 Claims, 25 Drawing Sheets

(56) References Cited

U.S. PATENT DOCUMENTS

| | | | |
|---|---|---|---|
| 7,996,054 B2 | 8/2011 | Say et al. | |
| 8,030,094 B2 | 10/2011 | Walt et al. | |
| 2004/0018495 A1* | 1/2004 | Li | C07H 21/02 |
| | | | 435/6.1 |
| 2013/0034847 A1* | 2/2013 | Kojic | C12Q 1/6804 |
| | | | 435/6.1 |

OTHER PUBLICATIONS

U.S. Appl. No. 05/079,520-A1, filed Apr. 2005, Wu.
U.S. Appl. No. 06/292,624-A1, filed Dec. 2006, Thorp, et al.
U.S. Appl. No. 07/166,744-A1, filed Jul. 2007, Knobel.
U.S. Appl. No. 09/181,852-A1, filed Jul. 2009, Clark, et al.
U.S. Appl. No. 10/006,451-A1, filed Jan. 2010, Gordon, et al.
U.S. Appl. No. 10/327,847-A1, filed Dec. 2010, Leiber, et al.
U.S. Appl. No. 11/223,583-A1, filed Sep. 2011, Gordon, et al.
U.S. Appl. No. 12/203,085-A1, filed Aug. 2012, Rebec.
U.S. Appl. No. 12/214,686-A1, filed Aug. 2012, Scaboo, et al.
Anon., "Product Data Sheet 721, ProActive® Streptavidin Coated Microspheres", Bangs Laboratories, Inc. (2013).
Anon., "Tech Tip # 65: ELISA technical guide and protocols", Thermo Fisher Scientific Inc.
Anon., "Technical Guide for ELISA", KPL Inc., (2013).
Anon., "Thermo Scientific Pierce Assay Development Technical Handbook", V2, Thermo Fisher Scientific Inc (2011).
Anon., "Quanterix's Ultrasensitive Simoa™ Technology Forges New Ground with Direct Detection of Genomic DNA in Human Blood . . . ", Press Release, Quanterix Inc., (Jan. 2013).
Arumugam, P., at al, "Wafer-scale fabrication of patterned carbon nanofiber nanoelectrode arrays . . . ", Biosensors and Bioelectronics 24: 2818-2824 (2009).
Borgmann, S., et al, "Advances in electrochemical science and engineering", WILEY-VCH Verlag GmbH & Co., 1-83 (2011).
Burd, E., "Validation of Laboratory-Developed Molecular Assays for Infectious Diseases", Clin. Microbiol. Rev. 23(3):550 (2010).

Chikkaveeraiah, B., et al, "Electrochemical Immunosensors for Detection of Cancer Protein Biomarkers", ACS Nano, 6(8): 6546-6561 (Aug. 2012).
Chita, G., et al., "Electrochemical DNA biosensor for environmental monitoring," Analytica Chimica Acta 427:155-164 (2001).
Claussen, J., et al, "Electrochemical Glucose Biosensor of Platinum Nanospheres Connected by Carbon Nanotubes", J Diabetes Sci Technol 4(2): 312-319, (Mar. 2010).
Cromley, J., "ELISA Assays recent innovations take analyte detection to new levels", Drug Discovery World Fall 2012, 23-45 (2012).
Drummond, T., et al, "Electrochemical DNA sensors." Nature Biotechnology, 21(10): 1192-1199 (Oct. 2003).
Keresztes, M., "ELISA: a solid-phase immune assay", Theoretical course: Basic biochemical methods and ischemic heart models, University of Szeged, Hungary.
Kim, J., et al. "Microfluidic Integrated Multi-walled Carbon Nanotube (MWCNT) Sensor for Electrochemical . . . ", Sensors and Actuators B: Chemical, 186: 370-376 (Aug. 2013).
Kuila, T., et al, "Recent advances in graphene-based biosensors". Biosensors and Bioelectronics 26 (12): 4637-4648 (Aug. 2011).
Muti, M., et al, "Electrochemical Monitoring of Nucleic Acid Hybridization by Single-Use Graphene Oxide-Based Sensor", Electroanalysis 23 (1): 272-279 (2011).
Shen, H., et al, "Biomedical applications of graphene", Theranostics, 2(3): 283-294 (2012).
Thevenot, D., et al, "Electrochemical Biosensors: Recommended Definitions and Classification", Pure Appl. Chem., 71(12) 2333-2348 (1999).
Toghill, K., Electrochemical Non-enzymatic Glucose Sensors: A Perspective and an Evaluation:, Int. J. Electrochem. Sci., 5:1246-1301 (2010).
Yoo, E., et al, "Glucose Biosensors: An Overview of Use in Clinical Practice", Sensors 2010 (10): 4558-4576 (2010).
Wang, H., "Glucose biosensor based on platinum nanoparticles supported sulfonated-carbon nanotubes modified glassy carbon elec . . . ", Int. J. Electrochem. Sci., 2: 508-516 (2007).
Zhu, Z., et al, A Critical Review of Glucose Biosensors Based on Carbon Nanomaterials: Carbon Nanotubes and Graphene, Sensors 12: 5996-6022 (2012).

* cited by examiner

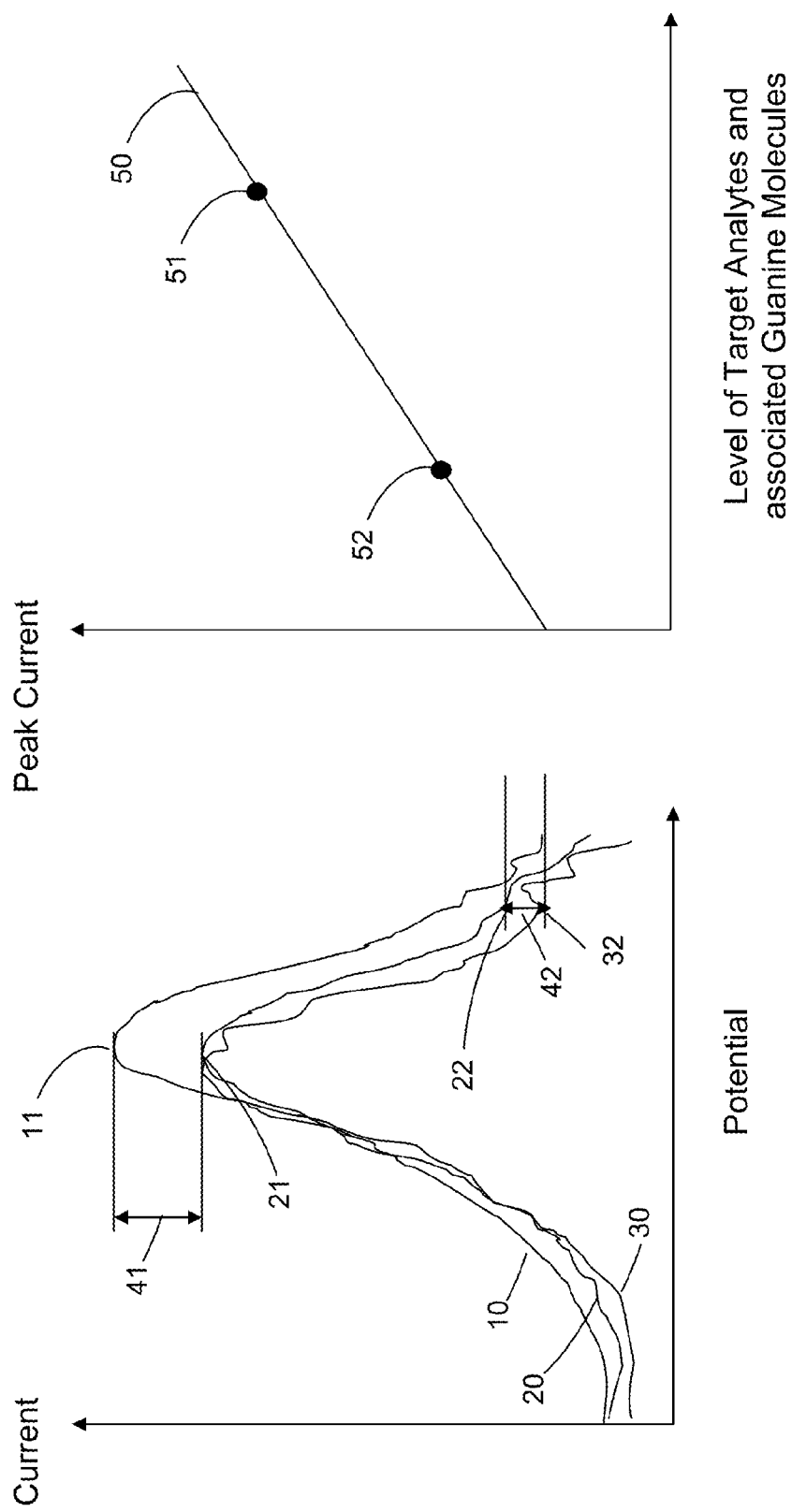

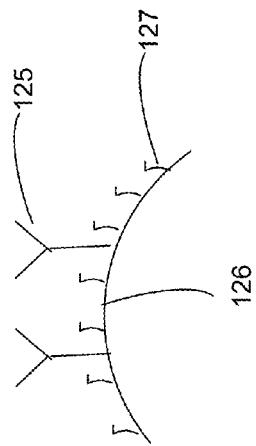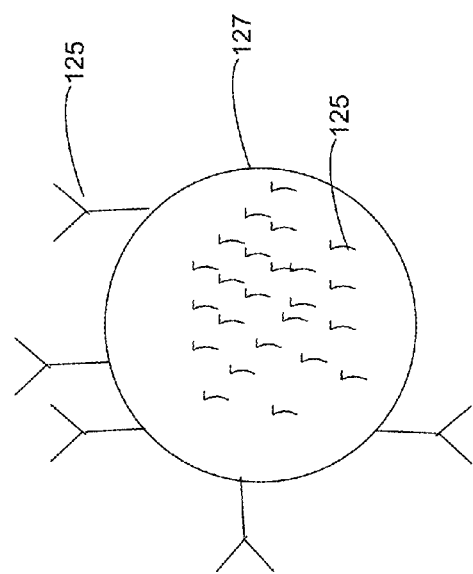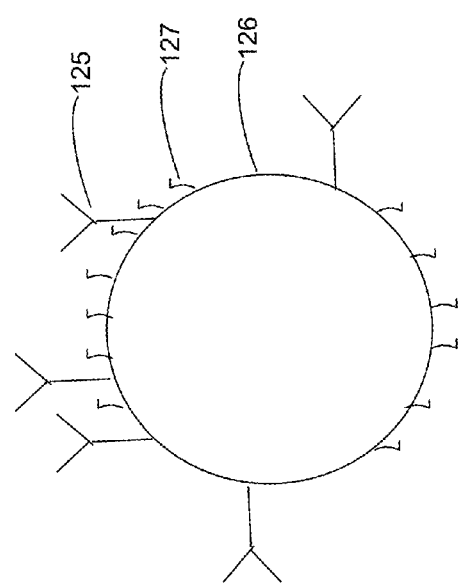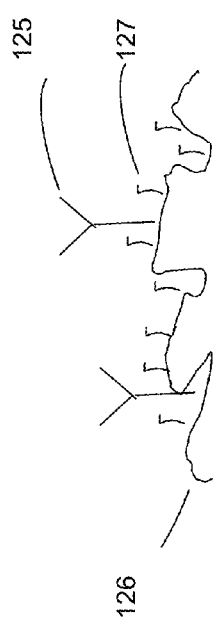
FIG. 11A
FIG. 11B
FIG. 11C
FIG. 11D

ULTRA-SENSITIVE DETECTION OF EXTREMELY LOW LEVEL BIOLOGICAL ANALYTES USING ELECTROCHEMICAL SIGNAL AMPLIFICATION AND BIOSENSOR

CROSS-REFERENCE TO RELATED APPLICATIONS

This application claims benefit under 35 U.S.C. §119(e) of U.S. provisional patent application Ser. No. 61/760,848 titled "Amplification and electrochemical quantification of non-redox species of biological analytes using electrochemically detectable tags", filed on Feb. 5, 2013, which, including all figures and tables, is incorporated herein by reference in its entirety.

This application refers to a sequence listing, which is provided as an electronic document filename "Amplification Tags_Rev1_ST25", 2896 bytes in size, created on Sep. 10, 2014, and which is incorporated herein by reference in its entirety.

FIELD OF THE INVENTION

The present invention relates generally to the field of biological assays. More particularly, the invention related to devices and methods that allow ultra-low levels of virtually any biological analyte to be detected and quantified rapidly, simply and inexpensively.

BACKGROUND OF THE INVENTION

The following discussion of the background of the invention is merely provided to aid the reader in understanding the invention and is not admitted to describe or constitute prior art to the present invention. All references, including publications, patent applications, and patents, cited herein are incorporated by reference in full to the same extent as if each individual publication was specifically and individually indicated to be incorporated by reference.

The analysis of biological analytes is critical for human health, safety and the environment. For example, infectious diseases can be diagnosed and treated by identifying the specific causes of the disease. This can be done by analyzing bodily samples using biological assays for the presence of disease-causing biological analytes including cells such as bacteria, protozoa and fungi, virus particles, toxins caused by the infectious materials, as well as biomolecular constituents of the infectious materials such as DNA, RNA and proteins.

Diseases, cancers and medical conditions such as cardiac arrest can be identified by the presence and levels of protein antigens and antibodies produced by the human immune system or other bodily mechanism. Genetic markers can also be used to indicate an abnormal state or predisposition to diseases, cancers and medical conditions. Hazardous biological materials can also be transmitted by infected food, plants, water, air, objects such as surfaces or containers, insects, birds, fish, lizards, rodents, animals, and people. Samples can be analyzed for pathogenic cells, virus particles, protein toxins, and biomolecules such as nucleic acids and proteins. Some hazardous biological materials are naturally occurring while others can be intentionally released by bioterrorists. Many other applications and sectors such as biotechnology, pharmaceutical, and forensic also require analysis for the identification, presence and levels or concentrations of biological analytes.

Accurate, timely and practical analysis of biological analytes is extremely complex. Some analytes can be present as substances that are difficult and costly to accurately assay. Some analytes are not specific to a single disease, cancer, or medical condition, and some diseases, cancers and medical conditions are not specific to a single analyte. Therefore identification of analytes can require multiplex assays for multiple analytes and in some cases multiple types of analytes for confirmation.

Some analytes can be present in extremely low levels and may not be detected by an assay, resulting in false negative outcomes. This requires highly sensitive assays and preferably the additional use of an amplification or enrichment process to increase the level of analytes before assaying.

Some analytes can be surrounded by non-specific materials in several orders of magnitude greater levels, as well as non-specific materials comprising non-specific strains and species of the target analyte which are physically and chemically similar. Non-specific materials can prevent the analytes from being detected by an assay, and result in false negative outcomes. In the case where the analyte is not present in the sample, the non-specific material may be incorrectly detected by the assay, causing a false positive outcome. This requires highly specific assays and preferably the additional use of a purification process to remove non-specific materials before assaying.

Even though some analytes may be present in a sample and correctly detected by the assay, some analytes can have an abnormal or harmful level which is higher or lower than a normal level. Some analytes have levels that change over time. This requires assays that can quantify analyte levels or concentrations, accurately and frequently.

Some analytes are highly infectious, extremely harmful, and costly to treat or remediate. These analytes need to be analyzed in a very timely manner to minimize the transmission of the infection. As well, some analytes have an elevated level for a limited period of time. Some assay operators have limited technical proficiency and need assays that are automated and easy to use. Some testing organizations have budgetary constraints and require assays to be low cost for consumables, labor, sample collection, assay equipment and laboratory facilities.

Numerous assays are known for detecting biological analytes in a sample. Four general types of biological analytes are cells, nucleic acids, proteins and redox active species. The technologies and assays directed at detecting these analytes are basically separate and independent. In certain cases different technologies can be used to measure the presence of analytes associated with the same disease. As an example, Table 1 illustrates the relative limits of detection and turnaround times for selected commercial products that use cell cultures, nucleic acid amplification tests and protein immunoassays for detecting analytes associated with certain infectious diseases. Cell cultures and nucleic acid amplification tests have the lowest limits of detection but also have longer turnaround times because of the test complexity, labor-intensity, and laboratory logistics. Protein immunoassays can be done in laboratories, and are also available as simple rapid point-of-care tests that have a higher limit of detection.

TABLE 1

Relative Limits of Detection and Turnaround Times of Different Detection Technologies Used by Commercial Products

| Analyte | Cell Culture | Nucleic Acid Amplification Test | Protein Immuno-assay (Lab Test) | Protein Immuno-assay (POC Test) |
|---|---|---|---|---|
| Limit of Detection | | | | |
| *C. difficile* Toxin Protein | 1 pg/mL | 10 pg/mL | 300 pg/mL | 1000 pg/mL |
| *Campylobacter C. jejuni* Bacteria | $3 \times 10^2$ cfu/mL | $3 \times 10^3$ cfu/mL | $3 \times 10^6$ cfu/mL | $3 \times 10^7$ cfu/mL |
| HIV Virus | Not applicable to viruses | ~15 virions/mL | ~3000 virions/mL | >>3000 virions/mL |
| Turnaround Time | | | | |
| Time between sample and test result | 2-7 days | 1-2 days | 1-2 days | 5-60 min |

Cell assays employ viable cells to reproduce outside of their natural environment to amplify the detection signals. Targets cells reproduce in a growth media incubated at an appropriate temperature, gas mixture and pH. Materials can be included to suppress the growth of non-specific cells. Detectable dyes provide color which intensifies with an increasing number of cells. Cell cultures are sensitive assays, but have a slow turnaround time (2-7 days) for producing a detectable number of cell colonies, and can result in false positive results caused by non-specific strains of the target cells that reproduce in the growth media. Cell assays can fail if target cells are unable to reproduce due to cells being dead or injured, or from contamination of the growth media. Because of the labor-intensive processing, cell assays can also fail from technician error due to an incorrect manual process, or from an inability to distinguish target cells from non-specific materials.

Nucleic acid assays cause a target region of DNA strands to amplify using polymerase chain reaction (PCR) during repeated thermally-induced biochemical processes. DNA fragments are exposed to appropriate denaturing conditions including high temperature to melt double helix DNA into single DNA strands. The temperature is lowered and target regions of the single stands act as templates which anneal with complementary nucleotide primers. The temperature is raised to an activity temperature where a polymerase enzyme causes a chemical reaction to synthesize new single DNA strands complementary to the single strand DNA templates, which form double helix DNA. The process is repeated until a sufficient number of copies are produced. Fluorescent dyes or fluorophore-containing DNA probes create a detectable signal which intensifies with an increasing number of target DNA fragments. Nucleic acid assays are highly specific and increase in sensitivity when more detectable target DNA fragments are produced. Because of the complex processes for sample preparation, amplification, detection and quantification, nucleic acid assays require highly skilled operators using costly equipment and expensive laboratory facilities. This limits the number of organizations that can conduct nucleic acid assays. Bottlenecks can occur at test labs and cause delays in testing, treatment and remediation. Nucleic acid assays can fail when non-specific DNA products amplify due to contamination or improper sample processing in advance of PCR. Failure can also occur if detectable fluorescent dyes or fluorophores are not adequately delivered along with the replicated target DNA fragments.

Protein assays identify and quantify proteins such as hormones and enzymes, by acting as antigens or antibodies in a chemical reaction. One of the most common protein assays is enzyme-linked immunosorbent assay (ELISA). In a direct ELISA an antigen analyte is adsorbed to a plate and a blocking agent is added to block potential binding sites from non-specific materials. An antibody-enzyme complex is added to bind with the antigen analyte and the plate is washed to remove unbound antibody-enzyme complexes. An appropriate enzyme substrate is added to produce an optical signal proportional to the amount of antigen analyte in the sample. In a Sandwich ELISA, a matched pair of antibodies forms a sandwich structure containing a first outer antibody layer to capture the analyte, an internal layer comprising the antigen analyte and a second outer antibody layer to detect the analyte. The capture antibody is initially bound to the plate and then binds with the antigen analyte contained in a test sample. After washing, a detection antibody-enzyme complex is added to bind with the antigen analyte and the plate is washed to remove unbound capture antibody-enzyme complexes. An appropriate enzyme substrate is added to produce an optical signal proportional to the amount of antigen analyte in the sample. Direct ELISA is faster because only one antibody is being used and fewer steps are required. Sandwich ELISA can have a lower detection limit because each capture antibody can contain several epitopes that can be bound by detection antibodies. Sandwich ELISA can also be made more sensitive using avidin-biotin complexes which have several sites for enzymes to provide multiple enzymes per analyte. This can amplification the detection signal by ten to a few hundred times. In contrast, cell cultures and PCR can produce millions or more copies. Protein assays are relatively easy to use, rapid and low cost. A major disadvantage is the inability to significantly amplify protein signals, making it necessary for the subject or its immune system to produce a detectable level of target protein analytes. This waiting period can delay detection and subsequent treatment by weeks or months. If the protein analytes are assayed using immunoassay before a detectable level is secreted, then a false negative detection outcomes will be produced causing the disease to be undetected.

Another problem is the specificity of antibodies and antigens. Many antibodies, and particularly polyclonal can detect a wide range of species; however these can include non-specific strains that produce false positive detection outcomes. The use of highly specific monoclonal antibodies greatly improves the specificity.

All of the abovementioned assays suffer from limitations. None of these assays can identify all types of analytes. Unlike cell and nucleic acid assays, protein assays cannot support significant signal amplification which can limit the sensitivity of protein assays. Amplification used in nucleic acid amplification tests and cell cultures adds time, cost and complexity. Cell and protein assays can have insufficient specificity and can benefit from purification steps such as magnetic separation. This adds to the assay cost and complexity. Quantification can be difficult if done manually or expensive if a transduction system is needed to convert optical signals to electrical signals. Nucleic acid amplification assays are sensitive and specific, however the complex processes used for sample preparation, amplification, detection and quantification require highly skilled operators, costly equipment, expensive laboratory facilities, and timeconsuming laboratory logistics. This complexity limits the number of organizations that can conduct nucleic acid assays.

Another general type of biological assay is for redox species and works when a redox analyte electrochemically reduces and/or oxidizes at an electrode. A redox analyte is placed in close proximity to a set of electrodes and undergoes electrical stimulation such as applying a potential. This causes the analyte to lose electrons through oxidation or gain electrons through reduction, which can be measured as an electrical signal at the working electrode. The amount of analyte oxidized or reduced and the corresponding electrical signal reflect the quantity of analyte in the sample. Other materials may be also be present such as a mediator to transport redox electrons, and non-specific materials, both of which can cause electrical noise that interferes with the electrical signal from the analyte. When redox analytes are present in high levels, such as approximately $10^{14}$ glucose molecules in blood associated with 1.1 mmol/L, redox signals are relatively high compared with background noise and can be directly measured to provide rapid quantification with acceptable sensitivity and specificity. Since the detection signal is electrical, no expensive transduction system is needed to convert optical signals. This allows glucose meters using redox assays to be performed in rapid, easy to use, low cost instruments.

Other redox analytes can be present in very low levels such as approximately $10^4$ to $10^6$ guanine molecules associated with 5,000 copies/mL of HIV RNA in blood as required for clinical use. Low levels of guanine bases in nucleic acids such as RNA can be oxidized to generate very low electrical current signals while significant background noise currents are produced due to the relatively high potentials required for guanine oxidation. This makes it difficult to distinguish oxidation signals from background noise signals.

TABLE 2

Examples of Redox Analytes

| Redox Analyte | Sample | Level Required for Clinical Use | Redox Analytes Available for Electrochemical Quantification |
| --- | --- | --- | --- |
| Glucose | 1 µL whole blood | 1.1 mmol/L glucose (20 mg/dL) | ~$10^{14}$ glucose molecules |
| HIV | 100 µL whole blood | 5,000 RNA copies/mL | ~$10^4$-$10^6$ guanine molecules |

Various approaches have been employed to quantify nucleic acid analytes using redox assays by improving the signal-to-noise ratio. One approach reduces the active surface area of a biosensor working electrode by replacing a conventional solid working electrode with a nanobiosensor comprising randomly distributed forests of nanoscale structures on the electrode surface (Lieber, et al, Thorpe, et al). Another nanobiosensor approach replaces the randomly distributed forests of nanoscale structures with ordered arrays of nanoscale structures spaced at least 1 µm apart to further reduce the surface area of a working electrode (Gordon, et al). These approaches allowed the guanine signal to be better distinguished from noise over conventional solid working electrodes but not to the degree required for direct measurement of the low level of redox species associated with target bio-analytes such as guanine molecules. Fabrication of nanoscale structures, such as 100 nm diameter carbon nanotubes, provides additional complexity over microscale structures that result in the need for specialized production equipment with high cost and limited throughput, poor production yields, and high unit costs for nanobiosensors.

Another approach employs PCR to amplify target DNA before detection by a conventional biosensor (Ozkan, et al). The use of PCR provides added complexity, time and cost which negates the benefits experienced from the glucose redox assay.

Another approach employs magnetic separation to purify analytes by removing background interferences before detection by a conventional biosensor. Palesecek et al, and Wang and Kawde capture target sequences using probe DNA immobilized onto magnetic particles. After target hybridization, the particles are magnetically separated from the pool of analytes. The collected DNA is denatured in acidic solutions, and the free guanine and adenine nucleotides are collected and analyzed using anodic stripping voltammetry. Although the noise from other interferents can be reduced, the inherent background signal from water electrolysis always presents. As a result, the guanine oxidation signal is too low for direct measurement in the presence of such large background currents.

There is a need for an assay that can determine the presence and quantity of very low level analytes including multiple analytes and multiple types of analytes in the same sample, provide high sensitivity preferably with signal amplification, provide high specificity preferably with purification, and provide the above in a rapid, easy to use and low cost device, including the capability for point-of-care use.

SUMMARY OF THE INVENTION

In accordance with a first aspect of the present invention, there is provided a signal amplification sandwich structure for amplifying detection signals from analytes in a fluid sample, wherein said structure consists essentially of (a) a first outer layer comprising a magnetic particle conjugated with a plurality of an analyte binding material, (b) an inner layer comprising an analyte, and (c) a second outer layer comprising a nonmagnetic particle conjugated with a plurality of an analyte binding material and also conjugated with a plurality of an electrochemically detectable tag in greater amounts than the bound associated analyte. The signal amplification sandwich structure employs electrochemically detectable oligonucleotide tags for signal amplification, with the majority of said tags being guanine and selected from the group consisting of non-random placements of guanine, adenine, thymine and combinations thereof. Analyte amplification performance of said signal amplification sandwich structure can be tuned to meet the desired limit of detection by adjusting one or more of the following parameters: (a) the number of oligonucleotides per nonmagnetic particle; (b) the number of guanines per oligonucleotide; (c) the size of the nonmagnetic particle; and (d) the surface area of the nonmagnetic particle for binding electrochemically detectable tags. The number of oligonucleotides per nonmagnetic particle ranges from about $10^2$ to about $10^{13}$, the number of guanines per oligonucleotide ranges from about 10 to about 400, the diameter of a spherical nonmagnetic particle ranges from about 1 to about 400 microns, and the surface of the nonmagnetic particle may be smooth, rough, porous, or extended with attachments to other nonmagnetic particles. No optically detectable tags are used for amplification, detection or quantification.

In accordance with another aspect of the invention, there is also provided a device for amplifying, detecting and/or quantifying the level of one or more target analytes in a fluid sample, wherein said device consists essentially of (a) a magnetic separation unit, (b) an analyte amplification unit, (c) a tag discharge unit, and (d) an electrochemical detection unit; wherein said device employs one or more signal amplification sandwich structures for amplifying detection signals from analytes in a fluid sample, wherein said structure consists essentially of a first outer layer comprising a magnetic particle conjugated with a plurality of an analyte binding material, an inner layer comprising an analyte, and a second outer layer comprising a nonmagnetic particle conjugated with a plurality of an analyte binding material and also conjugated with a plurality of an electrochemically detectable tag in greater amounts than the bound associated analyte. The signal amplification sandwich structure employs electrochemically detectable oligonucleotide tags for signal amplification, with the majority of said tags being guanine and selected from the group consisting of non-random placements of guanine, adenine, thymine and combinations thereof. Analyte amplification performance of said signal amplification sandwich structure can be tuned to meet the desired limit of detection by adjusting one or more of the following parameters: (a) the number of oligonucleotides per nonmagnetic particle; (b) the number of guanines per oligonucleotide; (c) the size of the nonmagnetic particle; and (d) the surface area of the nonmagnetic particle for binding electrochemically detectable tags. The number of oligonucleotides per nonmagnetic particle ranges from about $10^2$ to about $10^{13}$, the number of guanines per oligonucleotide ranges from about 10 to about 400, the diameter of a spherical nonmagnetic particle ranges from about 1 to about 400 microns, and the surface of the nonmagnetic particle may be smooth, rough, porous, or extended with attachments to other nonmagnetic particles. No optically detectable tags are used for amplification, detection or quantification.

In accordance with another aspect of the invention, there is also provided a method for amplifying, detecting and/or quantifying the level of one or more analytes in a fluid sample, wherein said method consists essentially of the following steps performed sequentially: (a) providing a fluid sample that may contain non-specific materials and one or more analytes, (b) providing one or more sets of magnetic particles, wherein each set comprises a plurality of magnetic particles conjugated with a plurality of an analyte binding material to create analyte-magnetic particle complexes if an associated analyte is present, (c) providing one or more sets of nonmagnetic particles, wherein each set comprises a plurality of nonmagnetic particles conjugated with a plurality of an analyte binding material and also conjugated with a plurality of an electrochemically detectable tag in greater amounts than the bound associated analyte to create electrochemically detectable tag-nonmagnetic particle-analyte-magnetic particle structures if an associated analyte is present, and (d) providing one or more working electrodes, wherein each working electrode is conjugated with a plurality of a recognition probe to bind with associated electrochemically detectable tags, and an electrochemical detection technique produces electrochemical signals on each working electrode in proportion to the level of an associated analyte if said analyte is present in the fluid sample; wherein said method employs one or more signal amplification sandwich structures for amplifying detection signals from analytes in a fluid sample, wherein said structure consists essentially of a first outer layer comprising a magnetic particle conjugated with a plurality of an analyte binding material, an inner layer comprising an analyte, and a second outer layer comprising a nonmagnetic particle conjugated with a plurality of an analyte binding material and also conjugated with a plurality of an electrochemically detectable tag in greater amounts than the bound associated analyte. The signal amplification sandwich structure employs electrochemically detectable oligonucleotide tags for signal amplification, with the majority of said tags being guanine and selected from the group consisting of non-random placements of guanine, adenine, thymine and combinations thereof. Analyte amplification performance of said signal amplification sandwich structure can be tuned to meet the desired limit of detection by adjusting one or more of the following parameters: (a) the number of oligonucleotides per nonmagnetic particle; (b) the number of guanines per oligonucleotide; (c) the size of the nonmagnetic particle; and (d) the surface area of the nonmagnetic particle for binding electrochemically detectable tags. The number of oligonucleotides per nonmagnetic particle ranges from about $10^2$ to about $10^{13}$, the number of guanines per oligonucleotide ranges from about 10 to about 400, the diameter of a spherical nonmagnetic particle ranges from about 1 to about 400 microns, and the surface of the nonmagnetic particle may be smooth, rough, porous, or extended with attachments to other nonmagnetic particles. No optically detectable tags are used for amplification, detection or quantification.

Other features and advantages of the present invention will be better understood upon reading of preferred embodiments thereof with reference to the appended drawings.

BRIEF DESCRIPTION OF THE DRAWINGS

FIGS. 2 and 6 show a detailed flow chart illustrating a detection method according to an embodiment of the present invention.

FIG. 9 is a graph of electrical current versus potential illustrating three electrochemical detection scans.

FIG. 10 is a graph of peak electrical current versus analyte level or concentration for quantifying test samples.

FIG. 11A is a schematic representation of an electrochemically detectable tag delivery system with the tags bound on the surface of the structure.

FIG. 11B is a schematic representation of a delivery system with a smooth surface.

FIG. 11C is a schematic representation of a delivery system with a rough or porous surface.

FIG. 11D is a schematic representation of a delivery system with the tags contained on the inside of the structure.

DETAILED DESCRIPTION OF THE PREFERRED EMBODIMENTS

Figure 1:
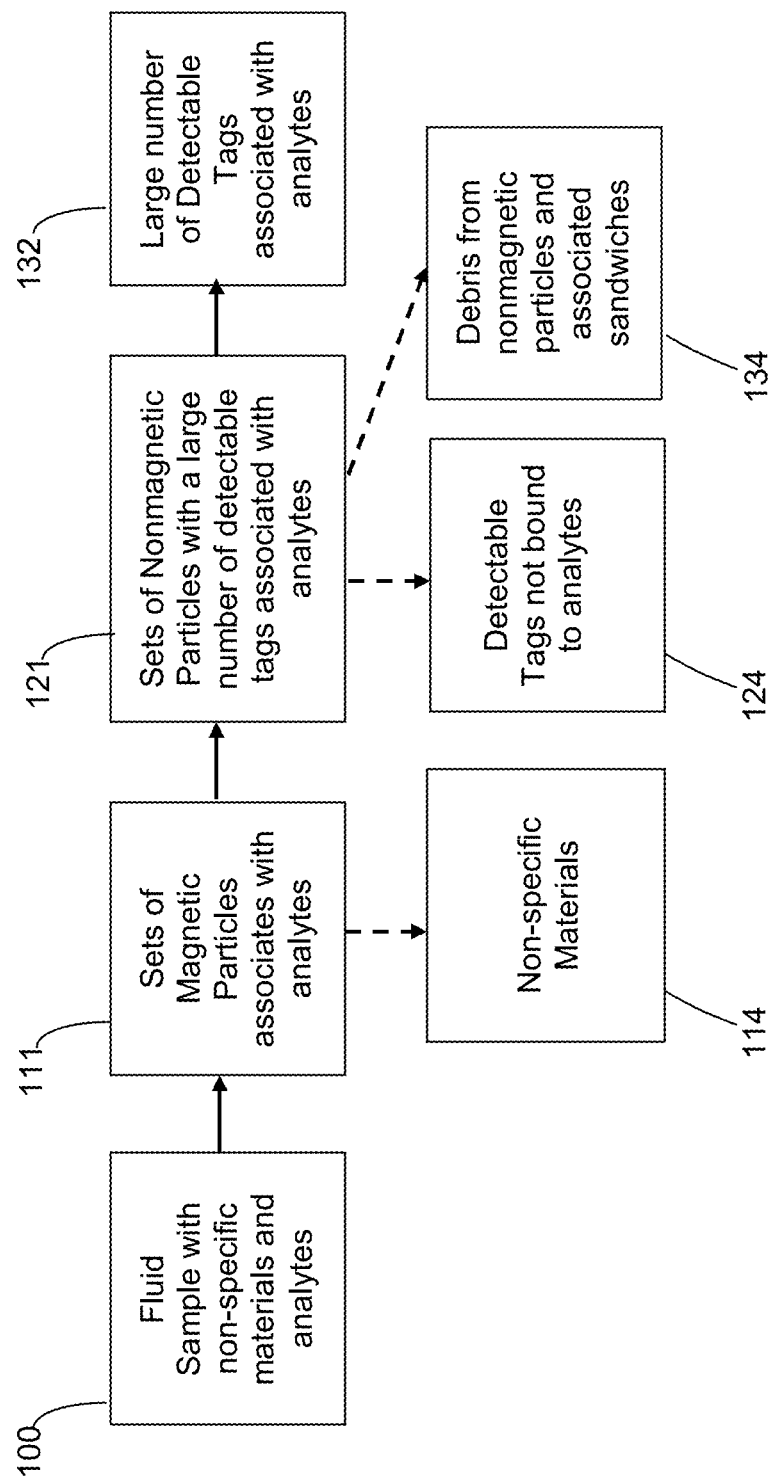
FIG. 1 shows a flow chart generally illustrating an amplification method according to an embodiment of the present invention.

In this specification, although the preferred embodiments have been described in detail, it should be understood that various changes, substitutions and alterations may be made therein without departing from the spirit and scope of the instant invention. Therefore, the specification is to be regarded in an illustrative rather than a restrictive sense.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context.

In order to facilitate review of the various examples of this disclosure, the following explanations of specific terms are provided:

Amplification ratio—The ratio of guanine molecules per target analyte to be detected and/or quantified. The guanine molecules are provided as bases in electrochemically detectable tags.

Analyte—A substance of interest being analyzed in an analytic procedure.

Analyte Binding Material—A natural or synthetic material that can bind with an analyte such as an antibody with an antigen analyte or an oligonucleotide with a nucleic acid analyte.

Biosensor—An analytical device for detecting a biological analyte using a biological receptor that recognizes the analyte, and a transducer that converts the recognition event into a measurable signal. An example of a recognition event is hybridization.

Electrochemical biosensor—A biosensor that employs an electrochemical transducer.

Electrochemical detection—A series of techniques for determining the presence and/or level of a redox species by measuring the electrical signal in a solution between a working electrode and a counter electrode due to the loss or gain of electrons in a redox reaction. The reaction is caused by electrical stimulation such as applying an electrical potential.

Electrochemically detectable tag—A tag used for electrochemical detection comprising at least one redox species such as guanine. A tag can be an oligonucleotide.

Electron transport mediator—A material or molecule that shuttles electrons. In the case of an electrochemical biosensor, electrons are shuttled between biological receptors and working electrodes.

Guanine—One of the four main nucleobases found in the nucleic acids DNA and RNA and forms a base pair with cytosine. Guanine is the only nucleobase that is a redox species.

Level of Quantification—The lowest quantity of an analyte that needs to be quantified in a particular application. The "Level" of Quantification can be much higher than the "Limit" of Quantification that is possible with a detection system.

Limit of Detection (LOD)—The lowest quantity of an analyte that can be distinguished from the absence of that substance (a blank value) within a stated confidence limit (generally 1%).

Limit of Quantification (LOQ)—The lowest quantity of an analyte that can be quantified within a stated confidence limit. Since quantifying an analyte is more difficult than detecting an analyte, the Limit of "Quantification" is typically higher than the Limit of "Detection".

Linear Dynamic Concentration Range—The concentration range over which the response of the biosensor is linear and constant (generally to within 5%).

Nanobiosensor—A biosensor that employs nanoscale features to improve its ability to distinguish target analyte signals from background noise. In the context of electrochemical biosensors, signal-to-noise resolution improves with smaller working electrode surface areas. Electrochemical nanobiosensors can employ nanoscale structures such as the edge plane tips in carbon nanotubes to reduce the active surface area of a biosensor working electrode by several orders of magnitude.

Oligonucleotide—A short single-stranded nucleic acid chain that is synthetically produced with a sequence of bases complimentary to a specific biological target.

Recognition probe—A probe that can act as a biological receptor in a biosensor. In the case of an electrochemical biosensor, the recognition probe typically comprises cytosine which can hybridize with redox active guanine tags.

Redox reaction—A class of electrode reactions involving oxidation/reduction of two dissolved redox species.

Redox species—A species of an element which can occur in more than one oxidation state in natural aqueous environments. Examples of redox species include glucose, guanine and ruthenium bipyridine.

Signal-to-Noise Ratio—The ratio of the level of a desired detection signal to the level of background noise.

The present invention generally provides methods, devices and structures for amplifying the detection signal from low level biological analytes in a fluid sample, and delivering a greatly amplified number of detectable tags to a separate device for detection and/or quantification. The present invention also provides methods, devices and structures for purifying, amplifying and quantifying biological analytes in a fluid sample from a single integrated method or device.

Electrochemical detection is among the easiest, most rapid and least costly biodetection technique on the market and is the gold standard for quantifying glucose, metabolites, electrolytes, and blood gases. However, its applications are limited to the subset of analytes that have redox properties and also are present in concentrations that are high enough to be detected by an electrochemical biosensor.

This invention allows ultra-low levels of virtually any biological analyte to be detected and quantified rapidly, simply and inexpensively with an electrochemical biosensor using a novel electrochemical signal amplification technique. The invention amplifies detection signals from low level analytes using an innovative sandwich ELISA structure that replaces optical labels with a massive amount of electrochemically detectable guanine rich oligonucleotide tags. Selective binding is achieved with matched pairs of either commercial or custom analyte binding materials such as monoclonal antibodies or single stand DNA. The guanine tags are eluted from the sandwich structures and hybridize with complementary cytosine rich oligonucleotide recognition probes attached to the surface of a biosensor working electrode. An electrochemical technique generates a signal in proportion to the guanine level on the working electrode which is also proportional to the analyte level in the sample. Magnetic separation and a nanobiosensor are used to improve the signal-to-noise ratio for measuring analyte levels 1,000,000 times lower than enzyme-linked immunosorbent assay (ELISA).

Not only could this invention allow diseases, cancers and medical conditions to be detected at a much earlier stage when treatment options are less expensive and more successful, it could also enable a new generation of diagnostics that can measure extremely low level analytes using a rapid, simple and inexpensive point-of-care device, similar to a glucose meter.

The invention's signal amplification sandwich structure consists essentially of (a) a first outer layer comprising a magnetic particle conjugated with a plurality of an analyte binding material, (b) an inner layer comprising an analyte, and (c) a second outer layer comprising a nonmagnetic particle conjugated with a plurality of an analyte binding material and also conjugated with a plurality of an electrochemically detectable tag in greater amounts than the bound associated analyte. Unlike other sandwich ELISA configurations, this invention uses no optically detectable tags for amplification, detection or quantification. The electrochemically detectable tags are oligonucleotides with the majority being guanine in non-random placements of guanine, adenine and/or thymine. The nonmagnetic particle can be a spherical bead and made from styrene, polystyrene, porous polystyrene, polymer, agarose, glass, ceramic, composite material and combinations thereof. The analyte binding materials can be antibodies, monoclonal antibodies, polyclonal antibodies, amino acids, peptides, proteins, haptens, nucleic acids, oligonucleotides, DNA, RNA, aptamers, and combinations thereof. As known by one skilled in the art, sandwich ELISAs typically require two different binding materials referred to as matched pairs and in the case of an antigen analyte, each of the binding materials will be antibodies that react with a different epitope of the antigen. Furthermore monoclonal antibodies are specific for a single epitope and can be obtained in very pure form to be reactive with different epitopes. By using different antibodies on the magnetic bead and non-magnetic bead, the sandwich structure will increase the specificity of the assay, since few potentially cross reacting molecules will share two epitopes.

An innovative aspect of this invention is that the analyte amplification performance can be tuned to meet the desired limit of detection by adjusting the number of oligonucleotides per nonmagnetic particle, the number of guanines per oligonucleotide, and the size and surface area of the nonmagnetic particle for binding electrochemically detectable tags. As an illustration of the optional configurations, the number of oligonucleotides per nonmagnetic particle can range from about $10^2$ to about $10^{13}$, the number of guanines per oligonucleotide can range from about 10 to about 400, the diameter of a spherical nonmagnetic particle can range from about 1 to about 400 microns, and the surface of the nonmagnetic particle can be smooth, rough, porous, or extended with attachments to other nonmagnetic particles.

As an example of an embodiment of the invention, the amplification performance was set at $1.46 \times 10^8$ guanine molecules per analyte by binding $7.3 \times 10^6$ oligonucleotide tags per nonmagnetic bead, with each oligonucleotide tag containing 20 guanines of 30 bases GTG GGT GGG TAA GGA GTG AGG GTG GGA GTT. It is necessary to ensure that the nonmagnetic bead used for the assay has sufficient surface area to fit the required number of oligonucleotide tags. In this example, $7.3 \times 10^6$ oligonucleotides can fit on a 15.28 micron spherical bead based the maximum packing density of oligonucleotides per surface area being $\sim 10^{12}/\text{cm}^2$. If additional amplification is required to attain a lower limit of detection, then adjustments can be made for using longer oligonucleotides, a greater number of guanines per oligonucleotide, a larger bead size, a bead material with a porous surface, an attachment to other nonmagnetic particles, or combinations thereof.

This invention also employs techniques to reduce noise and remove non-specific materials that could interfere with the detection process. In the sandwich structure, one of the outer layers comprises a magnetic particle conjugated with a plurality of an analyte binding material which forms a magnetic bead-analyte complex when analytes are present in the sample. A magnetic field is applied to magnetically extract magnetic bead-analyte complexes from the sample which could contain non-specific materials that interfere with detection and generate noise. Non-specific materials are subsequently washed away. Magnetic separation is especially useful when an extremely low level of analyte is surrounded by a high level of non-specific materials, including non-specific species or strains of the analyte being detected. In another step when the complete sandwich structures are formed, unbound guanine tags are separated from the sandwich structures then a magnetic field is applied and unattached nonmagnetic particles are washed away.

As a further example of an embodiment of the invention, test samples were prepared with known concentrations of ultra-low levels of E. coli O157:H7 ranging from $5 \times 10^{-21}$ M to $5 \times 10^{-19}$ M in wastewater. Using a sample size of 1 mL, the range of analytes was calculated to be between approximately $5 \times 10^{-24}$ mols and $5 \times 10^{-22}$ mols The number of analytes in the 1 mL sample can alternatively be expressed as between approximately 3 and 300 E. coli O157:H7 cfu by multiplying the number of moles by Avogadro constant of $6.02 \times 10^{23}$/mol. Samples were exposed to approximately 2,000,000 magnetic beads conjugated with antibodies specific for E. coli O157:H7, then magnetic particles were magnetically separated from the sample and repeatedly washed. A lower number of magnetic beads could potentially be used to reduce the cost of processing a 1 mL sample. In addition, the sample could be filtered to reduce its volume.

The magnetic beads were then released from the magnetic field and mixed with a solution containing 100,000 nonmagnetic beads conjugated with a second antibody specific to E. coli O157:H7 and also conjugated with guanine oligonucleotide tags to provide each nonmagnetic particle with approximately $1.46 \times 10^8$ guanine molecules as described above. As is known to one skilled in the art, magnetic separation may not recover 100% of the analytes in a sample, and lower recovery is typically experienced at lower analyte levels. As well, sandwich ELISA tends to have lower recoveries than direct ELISA due to binding of two matched antibodies instead of a single antibody. By optimizing process variables such as the number of beads, antibody selection, contact time with the sample, and washing, meaningful recovery rates can be attained for low analyte levels such as about 80% for a single antibody and 60% for matched pairs. By accounting for these factors, it is possible to estimate the number of guanine molecules being available for detection by multiplying the number of analytes to be detected by the amplification ratio of guanine tags per analyte by the expected recovery rate. As a result, the range of 3 to 300 E. coli cfu should correspond to approximately $2.6 \times 10^8$ and $2.6 \times 10^{10}$ guanine molecules. Alternatively, this can be expressed as $4.4 \times 10^{-16}$ to $4.4 \times 10^{-14}$ mols of guanine associated with the E. coli O157:H7 analyte.

The guanine oligonucleotide tags were eluted from the sandwich structures and then delivered to an electrochemical biosensor. The biosensor comprises one or more working electrodes, wherein each working electrode is conjugated with a plurality of a cytosine rich recognition probe that hybridizes with complementary guanine rich tags. The recognition probes are oligonucleotides with the majority being cytosine in non-random placements of cytosine, thymine and/or adenine. Only complementary guanine tags and cytosine recognition probes form duplex structures. A nanobiosensor containing small working electrode surface areas for improved signal-to-noise resolution can be used for measuring signals from low level analytes.

A benefit of this invention is that multiple analytes can be measured at the same time from the same sample using unique sets of magnetic beads, nonmagnetic beads, guanine tags, working electrodes and cytosine recognition probes associated with specific analytes. A unique set can also be associated with a control analyte which is added in to the sample in a known concentration to ensure that the process steps are functioning properly.

As a further example of an embodiment of the invention, a graphene oxide nanostructure was formed on a glassy carbon electrode (GO-GCE) and was functionalized with cytosine oligonucleotides CAC CCA CCC ATT CCT CAC TCC CAC CCT CAA-3' Amine which complemented the GTG GGT GGG TAA GGA GTG AGG GTG GGA GTT guanine oligonucleotides used for amplification. Approximately $1 \times 10^{10}$ cytosine oligonucleotide probes were able to fit on a 1 mm² working electrode surface based the maximum packing density of oligonucleotides per surface area. The number of cytosine oligonucleotide probes on the sensor surface ($1 \times 10^{10}$) exceeded the number of guanine oligonucleotide tags on a non-magnetic bead ($7.3 \times 10^6$). By calculating the ratio of $1 \times 10^{10}$ cytosine oligonucleotide probes to $7.3 \times 10^6$ guanine oligonucleotide tags, it was possible to estimate that up to approximately 1,400 duplexes could be made before the working electrode surface becomes saturated. This ratio is also an indicator of the maximum linear dynamic range of analyte concentrations that could be established.

An innovative aspect of this invention is that the linear dynamic concentration range can be tuned to meet the desired requirement by adjusting the size of the working electrode, number of cytosine oligonucleotides probes per working electrode, and the amplification ratio of guanine tags per analyte. In cases where extremely wide linear dynamic concentration ranges are required then a dilution process can also be used to dilute a portion of the initial sample into a second sample and a portion of the second sample into a third sample and so on. Subsequently, the original sample and each dilution would be assigned a unique set of magnetic beads, nonmagnetic beads, guanine tags, working electrodes and cytosine recognition probes associated with specific analytes.

Another benefit of this invention is that the guanine oligonucleotide tags hybridize with complementary tags at the working electrode surface. This produces a bigger signal than if the guanine molecules were disbursed throughout the solution then transported to the working electrode surface during detection scans.

A mediator is used to transport electrons from the duplexes to the sensor surface during the detection process. The mediator is a redox species that oxidizes at about the same potential as guanine (approximately 1.04 v), and reduces in subsequent scans. Since guanine does not reduce, it will only produce a signal during the first scan. For example, if the mediator is tris(bipyridine)ruthenium or $Ru(bpy)_3$, then during the first oxidation scan the following reactions will take place when tris(bipyridine)ruthenium first oxidizes, then guanine oxidizes and tris(bipyridine) ruthenium transports guanine electrodes by reducing and oxidizing at the electrode:

$$Ru(bpy)_3^{2+} \rightarrow Ru(bpy)_3^{3+} + e^-$$

$$Ru(bpy)_3^{3+} + Guanine \rightarrow Ru(bpy)_3^{2+} + Guanine^+$$

$$Ru(bpy)_3^{2+} \rightarrow Ru(bpy)_3^{3+} + e^-$$

During subsequent oxidation scans only the tris(bipyridine)ruthenium oxidizes:

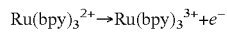

The invention's use of a mediator provides other useful information about the detection process. For example the signal generated by guanine plus the mediator is larger than guanine alone making it easier to measure signals associated with very low analyte levels. The mediator also provides an effective baseline measurement for measuring noise. When there is no guanine oxidation then the mediator oxidation signals should be approximately the same during each detection scan. Any variation in repeated scans would be due to noise and provides a cut-off threshold level for present/absent testing. The mediator signal should be relatively constant from scan to scan, from working electrode to working electrode, and from sensor to sensor. This allows the mediator to be used as a control to demonstrate that the sensor is working and as a calibrant to compare analyte signals from different sensors.

One method used by the invention for electrochemical detection is to perform a first, a second and a third amperometric detection scan with an electron transport mediator. The generated signal from guanine oxidation is measured as the difference in peak signal from a first scan minus peak signal from a second scan. The threshold presence/absence signal is the cut-off measurement due to noise where there is no guanine in the solution, and is measured as the greatest variation in signal from a second scan minus a third scan. An analyte is determined to be present if the generated signal from its associated electrochemically detectable tags is greater than the threshold presence/absence signal. In addition the level or concentration of an analyte is determined by comparing the generated electrochemical signal from an associated electrochemically detectable tag with predetermined signals from known levels of the analyte.

As a further example of an embodiment of the invention, approximately $1.3 \times 10^7$ guanine oligonucleotide tags were eluted from magnetically immobilized sandwich structures and delivered to a GO-GCE biosensor working electrode conjugated with approximately $1 \times 10^{10}$ cytosine oligonucleotide probes to form up to approximately $1.3 \times 10^7$ duplexes. As each guanine oligonucleotide in the duplex contained 20 guanine bases, then up to approximately $2.6 \times 10^8$ guanine molecules were bound to the surface of the working electrode. Following hybridization, sequential differential pulse voltammetry scans were applied in 0.2 M NaOAC buffer (pH 5) containing 5.0 µM $Ru(bpy)_3^{2+}$. The three electrode system also included a platinum counter electrode and silver/silver chloride reference electrode.

The detection peak signal generated from guanine plus $Ru(bpy)_3$ in scan 1 was approximately 80 nA. The detection signal generated from only $Ru(bpy)_3$ in the second scan was approximately 25 nA, leaving 55 nA as the difference from the first scan and second scan. The variability in subsequent scans was also measured and attributed to noise in the system when there was no guanine. The maximum variability between subsequent scans of only $Ru(bpy)_3$ was approximately 10 nA, which was less than the 55 nA associated with guanine. This confirmed the presence of guanine associated with $5 \times 10^{-21}$ M of E. coli O157:H7 analyte at the source.

As known by one skilled in the art, many factors can cause detection signals from the same concentration to vary from sensor to sensor such as surface oxidation of the electrode, fouling, working electrode fabrication quality especially with nanobiosensors, test operating conditions, etc. In order to more accurately compare signals from test to test, the invention provides a baseline signal from the mediator.

The mediator signal can be used to normalize signals from the guanine scan. The rationale is that if the signal from the mediator with a fixed concentration is different than the baseline signal, then the signal from guanine associated with an analyte concentration will also be different in proportion to the expected baseline signal. The ratio of the guanine signal divided by the guanine plus mediator signal will allow guanine signals to be more comparable from sensor to sensor. More specifically, the normalized calibration curve is formed by plotting the ratio of the signal from the guanine associated with the analyte (Scan 1 minus Scan 2) divided by the signal of guanine plus the mediator (Scan 1) versus the analyte concentration.

Figure 25:
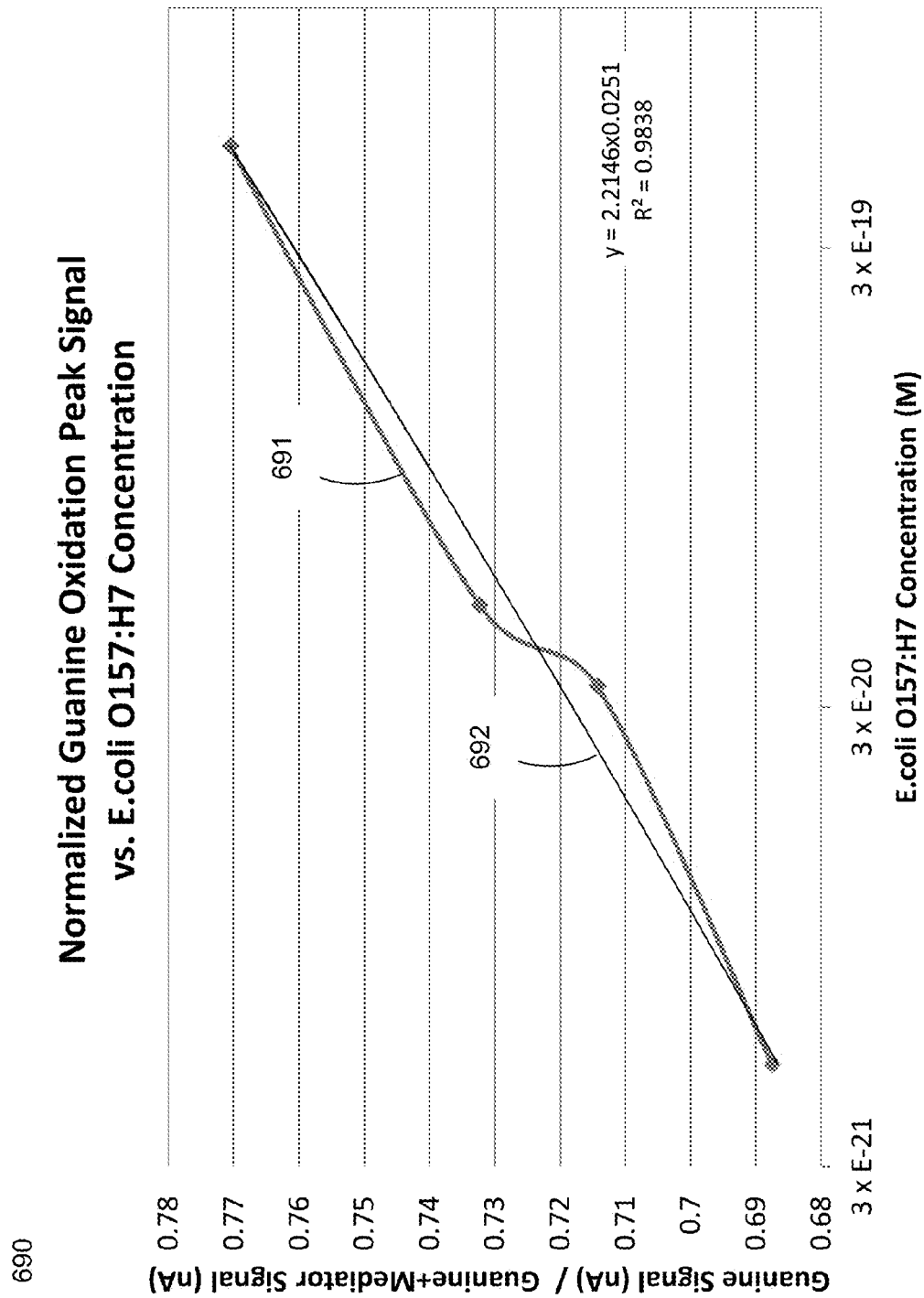
FIG. 25 is a graph of normalized guanine oxidation peak signal versus *E. coli* O157:H7 concentration from experiments using a dynamic concentration range of $5 \times 10^{-21}$ M to $5 \times 10^{-19}$ M.

As a further example of an embodiment of the invention, a linear dynamic concentration range was established for detecting ultra-low levels of E. coli O157:H7 between $5 \times 10^{-21}$ M and $5 \times 10^{-19}$ M. Multiple concentrations within the range were tested for detection signals and plotted as normalized guanine oxidation peak signal versus E. coli O157:H7 concentration as illustrated in FIG. 25. It should be noted that the current peak for $Ru(bpy)_3$ varied by 14% from $29.2 \pm 4.2$ nA, which was used to normalize the signals and produce a coefficient of determination of 0.9838 indicating the fit of the data.

Some of the other benefits and unique features of the invention include:
  Robustness—The invention can be used for a wide range of analyte types and specific protein markers, such as immunoglobulins, surface proteins on bacteria and viruses, protein toxins, hormones, and enzymes. Nucleic acids can also be detected and quantified.
  Rapid Detection Time—All process steps can be undertaken in about 1 hour using prefabricated consumables.
  Low Cost—By avoiding optional detection and transduction, relatively inexpensive reagents and equipment are needed to conduct a test.
  Ease of Use—The invention's process steps invention can be automated and used in a point-of-care device with no operator involvement.

However, the truly innovative aspect of the invention is allowing ultra-low levels of virtually any biological analyte to be detected and quantified rapidly, simply and inexpensively with an electrochemical biosensor. A comparison of the measurement capabilities of the invention with other biodetection platforms is provided in the following tables. The values and estimates are sourced from references that describe detection limits for a wide range of similar groups of technologies and platforms. Specific technologies can have values that deviate from the values being reported. The term measurement capability is used as a general term to correlate comparative values reported for sensitivity, limit of detection and limit of quantification.

Redox biosensors are described in Table 4. Values are reported for glucose meters since the vast majority of commercial redox biosensors are used for the detection of glucose in blood. Values are provided for the lower range of blood glucose measurements, commercial glucose enzyme biosensors, and experimental glucose nanobiosensors. Comparative values from this invention are also provided to illustrate the vastly improved measurement capability from the invention's amplification capability.

The first rows of Table 4 show the lower concentration requirement for measuring glucose in whole blood as 1.1 mmol/L (or 20 mg/dL). Some commercial glucose meters such as Abbott FreeStyle® (Abbott Diagnostics Care, Alameda, Calif.) detect glucose from a 0.3 μL sample. This corresponds to $3.3 \times 10^{-10}$ moles of glucose by multiplying 1.1 mmol/L concentration by 0.3 μL sample volume. The level can also be expressed as $2 \times 10^{14}$ glucose molecules by multiplying $3.3 \times 10^{-10}$ mols by Avogadro constant $6.02 \times 10^{23}$/mol.

Since commercial glucose meters need to measure the lowest required glucose levels, they typically have the additional capability to measure significantly lower levels as a safety margin. Kozar indicates a measurement capability of 0.033 mmol/L for Accu-Chek Compact Plus® portable instrument (Roche Diagnostics GmbH, Mannheim, Germany). This converts to about $6.0 \times 10^{12}$ molecules which is approximately 33 times lower than the lower range of glucose levels.

Lower measurement limits have been achieved with nanobiosensors that employ nanometer-scaled structured materials as the working electrode. Nanobiosensor working electrodes have a smaller electro-active surface area than conventional biosensors. This improves the biosensor's signal-to-noise resolution by allowing small electrical signals generated from lower levels of analytes to be distinguished from background noise. Zhu reports a measurement capability of approximately 0.00001 mmol/L for certain nanobiosensors, which converts to measuring $1.8 \times 10^{10}$ molecules or about 300 times lower levels than conventional biosensors. Many nanobiosensor are not commercially viable as they encounter high fabrication costs, inconsistency signals from sensor to sensor due to poor fabrication quality at the nanoscale, difficulties in measuring low nano-Amp and picoAmp signals.

In contrast, this invention has attained $5.0 \times 10^{-18}$ mmol/L levels, which was a 13 order of magnitude improvement over the measurement capabilities of glucose nanobiosensors, by using a unique combination of detection technologies. The invention's amplification beads converted 3 analyte molecules into $2.6 \times 10^8$ detectable guanine redox molecules. A greater amplification ratio of up to $10^{15}$ electrochemically detectable targets per analyte could have been used to generate a bigger signal. Non-specific materials were removed from analytes using magnetic separation to reduce noise during detection. The guanine molecules were bound near the working electrode surface when hybridized with cytosine probes to generate a higher signal than if the redox materials were disbursed throughout the solution. A graphene oxide nanobiosensor was used which is low cost, easy to fabricate and generated easy-to-measure signals in the 30-100 nA range. As well, a normalization process was able to correct measurement inconsistencies from sensor to sensor.

TABLE 4

Relative Measurement Capabilities of Representative Redox Biosensors and the Invention

| Measurement Capabilities | Blood Glucose Lower Limit | Glucose Enzyme Biosensor | Glucose Nano-biosensor | Invention Amplification & Nanobiosensor |
|---|---|---|---|---|
| Source Concentration ||||| 
| mM | 1.1 | 0.033 | 0.0001 | $5.0 \times 10^{-18}$ |
| M | $1.1 \times 10^{-3}$ | $3.3 \times 10^{-5}$ | $1.0 \times 10^{-7}$ | $5.0 \times 10^{-21}$ |
| Sample Volume ||||| 
| Sample (mL) | 0.0003 | 0.0003 | 0.0003 | 1.0 |
| Analytes in Sample ||||| 
| Molecules | $2.0 \times 10^{14}$ | $6.0 \times 10^{12}$ | $1.8 \times 10^{10}$ | 3 |
| Moles | $3.3 \times 10^{-10}$ | $1.0 \times 10^{-11}$ | $3.0 \times 10^{-14}$ | $5.0 \times 10^{-24}$ |

TABLE 4-continued

Relative Measurement Capabilities of Representative Redox Biosensors and the Invention

| Measurement Capabilities | Blood Glucose Lower Limit | Glucose Enzyme Biosensor | Glucose Nano-biosensor | Invention Amplification & Nanobiosensor |
|---|---|---|---|---|
| System Amplification ||||| 
| Amplified Targets per Analyte | 1 | 1 | 1 | $1.5 \times 10^8$ |
| Recovery by Antibodies | 100% | 100% | 100% | 60% |
| Amplified Targets in Sample ||||| 
| Molecules | $2.0 \times 10^{14}$ | $6.0 \times 10^{12}$ | $1.8 \times 10^{10}$ | $2.6 \times 10^8$ |
| Moles | $3.3 \times 10^{-10}$ | $1.0 \times 10^{-11}$ | $3.0 \times 10^{-14}$ | $4.4 \times 10^{-16}$ |

Table 5 provides the relative measurement capabilities of representative direct ELISA and sandwich ELISA platforms used for the detection of proteins. The values and estimates are provided from ELISA technical documents published by KPL (Gaithersburg, Md.) and Thermo Scientific (Rockford, Ill.).

Sandwich ELISAs using horseradish peroxide (HRP) enzymes and colorimetric detection are the most common immunoassays. ELISA measurement capabilities are typically expressed in pg/mL. For a typical protein such as Interleukin 2 (IL-2), the relative detection limits are approximately 2,125 pg/mL for direct ELISA and 1.4 pg/mL for sandwich ELISA. ELISA applications requiring sensitivities below 1 pg/mL can be obtained using chemiluminescent or chemifluorescent substrates which are much more expensive and more difficult to use. Because the molecule weights of proteins vary, a better unit to compare detection platforms is pmols. For example, in the case of Interleukin 2 (IL-2) protein with a molecular weight of 17,000 g/mol, 2125 pg/mL can be converted to pM by dividing the concentration of 2125 pg/mL by the molecular weight of 17,000 g/mol and multiplying by 1000 mL/L. This provides detection capabilities of approximately 125 pmols for direct ELISA and 0.08 mmols for sandwich ELISA.

The sensitivity for sandwich ELISA is higher because of signal amplification. Each primary antibody contains several epitopes that can be bound by the labeled secondary antibody. Sandwich ELISA can also be made more sensitive using avidin-biotin complexes which have multiple sites for enzymes. This allows up to about 200 enzymes per analyte. In comparison, this invention provides many orders of magnitude greater amplification by binding up to $10^{15}$ electrochemically detectable tags per analyte. Using data from the E. coli O157:H7 example described earlier, the invention was able to detect 7 orders of magnitude lower levels than sandwich ELISA as illustrated in Table 5.

TABLE 5

Relative Measurement Capabilities of Direct ELISA, Sandwich ELISA and the Invention

| Measurement Capabilities | Direct ELISA | Sandwich ELISA | Invention Amplification & Nanobiosensor |
|---|---|---|---|
| Source Concentration |||| 
| pM | 125 | 0.08 | $5.0 \times 10^{-9}$ |
| M | $1.3 \times 10^{-10}$ | $8.3 \times 10^{-14}$ | $5.0 \times 10^{-21}$ |
| Sample Volume |||| 
| Sample (mL) | 0.1 | 0.1 | 1.0 |

TABLE 5-continued

Relative Measurement Capabilities of Direct ELISA,
Sandwich ELISA and the Invention

| Measurement Capabilities | Direct ELISA | Sandwich ELISA | Invention Amplification & Nanobiosensor |
|---|---|---|---|
| Analytes in Sample | | | |
| Molecules | $7.5 \times 10^9$ | $5.0 \times 10^6$ | 3 |
| Moles | $1.3 \times 10^{-14}$ | $8.3 \times 10^{-18}$ | $5.0 \times 10^{-24}$ |
| System Amplification | | | |
| Amplified Targets per Analyte | 1 | 200 | $1.5 \times 10^8$ |
| Recovery by Antibodies | 80% | 60% | 60% |
| Amplified Targets in Sample | | | |
| Molecules | $6.0 \times 10^9$ | $6.0 \times 10^8$ | $2.6 \times 10^8$ |
| Moles | $1.0 \times 10^{-14}$ | $1.0 \times 10^{-15}$ | $4.4 \times 10^{-16}$ |

Table 6 provides the relative measurement capabilities of emerging biodetection technologies. One group of technologies is bead sandwich ELISA where sandwiches are made using a first bead with a capture antibody, and a second bead with a detection antibody and an optical detectable label. Bead sandwich ELISA replaces a solid substrate from conventional ELISA with beads to provide less surface area for non-specific materials to bind to. The capture bead is typically a magnetic bead that permits magnetic separation to remove non-specific materials that could interfere with detection. The detection bead is typically a polymer and is also attached to an optical label. Singulex (Alameda, Calif.) uses detection beads with fluorescent dyes which are individually counted using an optical measurement device. Quanterix (Lexington, Mass.) uses fluorophores to generate optical signals in individual femtoliter wells. The measurement capabilities reported by Quanterix is shown in Table 6 as an improvement over sandwich ELISA by approximately 5 orders of magnitude. These systems are more expensive and more difficult to use than ELISA. Luminex (Austin, Tex.) has a second type of bead sandwich ELISA (xMAP). xMAP replaces the magnetic bead with a second polymer bead which uses a second fluorescent which is unique to the analyte to allow each analyte to be identified. The xMAP approach is less sensitive than magnetic bead sandwich ELISA but is more effective for high throughput and large multiplexing detection applications.

Another group of emerging detection technologies is immuno-nanobiosensors which use nanobiosensors, antibodies and enzymes to detect proteins. Immuno-nanobiosensors have employed gold nanoparticles, carbon nanotubes, magnetic particles, and quantum dots to improve the detection capabilities over conventional biosensors. Chikkaveeraiah reports that certain immuno-nanobiosensors have been able to detect approximately 0.17 pM levels using multi-label amplification which can have up to a few thousand detectable labels per analyte. However, this limited amplification is unable to reach limits of detection required by clinical applications. Furthermore, none of these technologies come close to attaining the invention's amplification capability of $10^{15}$ electrochemically detectable tags per analyte to detect extremely low levels, or implement capabilities to remove non-specific materials, multiplex, and normalize signals from inconsistent fabrication of nanobiosensors.

TABLE 6

Relative Measurement Capabilities of
Emerging Detection Technologies and the Invention

| Measurement Capabilities | Bead Sandwich ELISA | Immuno-Nanobiosensor | Invention Amplification & Nanobiosensor |
|---|---|---|---|
| Source Concentration | | | |
| pM | $7.6 \times 10^{-5}$ | 0.17 | $5.0 \times 10^{-9}$ |
| M | $7.6 \times 10^{-17}$ | $1.7 \times 10^{-13}$ | $5.0 \times 10^{-21}$ |
| Sample Volume | | | |
| Sample (mL) | 0.025 | 0.1 | 1.0 |
| Analytes in Sample | | | |
| Molecules | $1.1 \times 10^3$ | $1.0 \times 10^7$ | 3 |
| Moles | $1.9 \times 10^{-21}$ | $1.7 \times 10^{-17}$ | $5.0 \times 10^{-24}$ |
| System Amplification | | | |
| Amplified Targets per Analyte | 1 | 3,000 | $1.5 \times 10^8$ |
| Recovery by Antibodies | 100% | 60% | 60% |
| Amplified Targets in Sample | | | |
| Molecules | $1.1 \times 10^3$ | $1.8 \times 10^{10}$ | $2.6 \times 10^8$ |
| Moles | $1.9 \times 10^{-21}$ | $3.0 \times 10^{-14}$ | $4.4 \times 10^{-16}$ |

In term of its usefulness. the present invention can be valuable for the early diagnosis of diseases, cancers, and medical conditions, as well as in bioterrorism, food and water safety, biotechnology, pharmaceutical, and forensic applications. Representative applications are shown below.

TABLE 7

Representative Infectious Disease Applications

| | Blood/Plasma/Serum | Respiratory Swab/Sputum | Stool |
|---|---|---|---|
| Bacterial Infections | *Yersinia pestis* (Plague)<br>*Rickettsia* (Typhus)<br>VRE<br>*Salmonella typhi*<br>(Typhoid Fever)<br>*B. burgdorferi*<br>(Lyme disease)<br>*Listeria* | *Mycobacterium tuberculosis*<br>*Bacillus anthracis*<br>(Anthrax)<br>MRSA<br>*Acinetobacter baumannii*<br>*Mycobacterium leprae*<br>(Leprosy)<br>*Legionella* | *Clostridium difficile*<br>*Klebsiella*<br>*Vibrio cholerae*<br>(cholera)<br>*Salmonella*<br>*Campylobacter*<br>*Escherichia coli* |
| Viral Infections | Human Immunodeficiency Virus<br>Hepatitis<br>West Nile Virus | Influenza (H1N1, H5N1)<br>SARS<br>Variola (Smallpox)<br>Adenovirus (cold, | *Norovirus*<br>*Rotavirus*<br>Poliovirus |

TABLE 7-continued

Representative Infectious Disease Applications

| | Blood/Plasma/Serum | Respiratory Swab/Sputum | Stool |
|---|---|---|---|
| | Ebola (Hemorrhagic fever) Marburg virus Arenaviruses Dengue Fever Flaviviridae (Yellow Fever) | pneumonia) *Morbillivirus* (Measles) Varicella zoster virus (Chickenpox) Rubella (German Measles) | |
| Parasitic/Fungal Infections | *Plasmodium* (malaria) | *Aspergillus* | *Schitosoma Cryptosporidium Giardia* |

TABLE 8

Representative Cancer and Medical Condition Applications

| | Cancer Biomarkers | Medical Condition or Disease Biomarkers |
|---|---|---|
| Protein Biomarkers | Ovarian cancer (HE4) Various cancer types (CA125, CEA) | Rheumatoid arthritis (Anti-CCP) Rheumatoid arthritis (Anti-RF) Pre-eclampsia (sFlt/PlGF) Heart failure (NT-proBNP) Acute coronary syndrome (Troponin T/Troponin I) Osteoporosis (b-crosslaps, P1NP levels) Growth disorders (hGH) Transplantation (MPA levels) |
| Genetic Biomarkers | Melanoma (BRAF Mutation) Colorectal cancer (KRAS Mutation) | Sepsis Septi Fast Test |

It is understood that the above list and subsequent descriptions are given by way of example only, and is in no way limitative to the scope of the present invention. "Pharmaceutically acceptable" in the context of the present invention means a device or composition that is generally safe, non-toxic and biologically acceptable for veterinary and human use.

The invention's amplification and detection paradigm can be extended to a wide variety of applications using either a low cost conventional biosensor with a high amplification ratio of guanine molecules per analyte, or an ultrasensitive nanobiosensor with a lower amplification ratio of guanine molecules per analyte. Some representative examples are as follows.

TABLE 9

Representative Examples of the Invention For Amplification Required for Biosensor and Nanobiosensor

| Analyte | Sample | Level for Quantification | Analytes for Quantification | Amplification to provide $10^{14}$ guanine to a Biosensor | Amplification to provide $10^{8}$ guanine to a Nanobiosensor |
|---|---|---|---|---|---|
| Human Immunodeficiency Virus | 1 mL whole blood | 5,000 copies/mL HIV-1 RNA | 5,000 copies | $2 \times 10^{10}$ guanine molecules per analyte | $2 \times 10^{4}$ guanine molecules per analyte |
| *Clostridium difficile* (Multiplex) | 1 mL stool | 1 pg/mL Toxin B tcdB proteins | 1,900,000 proteins | $5 \times 10^{7}$ guanine molecules per analyte | 50 guanine molecules per analyte |
| | | 100 cfu/mL *C. difficile* BI/NAP1/027 | 100 cfu | $1 \times 10^{12}$ guanine molecules per analyte | $1 \times 10^{6}$ guanine molecules per analyte |
| Airborne Anthrax (Viable and dead spores) | 4 mL liquefied air filter concentrate | 25 cfu/mL Anthrax spores | 100 cfu | $1 \times 10^{12}$ guanine molecules per analyte | $1 \times 10^{6}$ guanine molecules per analyte |
| Airborne Anthrax (Only Viable spores) | 4 mL liquefied air filter concentrate | 25 cfu/mL Viable Anthrax spores | 100 cfu | $1 \times 10^{12}$ guanine molecules per analyte | $1 \times 10^{6}$ guanine molecules per analyte |
| *Salmonella Enteritidis* Group D1 | 100 mL egg pool | 10 cfu/mL *Salmonella Enteritidis* Group D1 | 1,000 cfu | $1 \times 10^{11}$ guanine molecules per analyte | $1 \times 10^{5}$ guanine molecules per analyte |

TABLE 9-continued

Representative Examples of the Invention
For Amplification Required for Biosensor and Nanobiosensor

| Analyte | Sample | Level for Quantification | Analytes for Quantification | Amplification to provide $10^{14}$ guanine to a Biosensor | Amplification to provide $10^{8}$ guanine to a Nanobiosensor |
|---|---|---|---|---|---|
| *Escherichia coli* O157:H7 | 100 mL chlorinated tap water | 1 cfu/100 mL (0.01 cfu/mL) | 1 cfu | $8 \times 10^{13}$ guanine molecules per analyte | $8 \times 10^{6}$ guanine molecules per analyte |

The invention also comprises many other unique capabilities. A partial list includes a purification-amplification-detection method that allows multiplexing, a delivery system capable of supplying guanine molecules, a sandwich structure for binding guanine tags with analytes, an ultra-sensitive nanobiosensor that does not require difficult-to-fabricate nanoscale structures, a family of analyzer configurations, a developer kit that can reduce the time-to-market for a diagnostic application from years to months for any validated monoclonal antibody or DNA probe, and a cartridge preparation instrument that allow developers to produce their own test cartridges in a few hours.

The starting sample may be embodied by any fluid which may contain an analyte, such as blood or other bodily fluids, liquefied solids or tissues, water or other liquids, or liquefied materials from air or gases. Examples include but are not limited to peripheral blood, plasma, serum, urine, saliva, nasal swab, tissue biopsy, surgical specimen, amniocentesis sample, autopsy material, body fluid, stool, surface, container, water, liquefied air particles, gases, food, food extracts, beverages, and other materials coming from human subjects, veterinary subjects, animals, rodents, lizards, fish, birds, insects, plants, and biological structures. Original samples may be taken from any source. A sample may also be a liquid derived from the original sample by removing or adding components.

The analyte may be any biological material of interest which one may wish to identify, detect or quantify. Examples of analytes include cells, bacteria, protozoa, fungi, virus particles, proteins, peptides, enzymes, hormones, haptens, cancer markers, nucleic acids, genes, oligonucleotides, DNA, RNA, small molecules, drugs, pesticides, organic chemicals, industrial chemicals and compounds. Analytes can be species-specific, strain-specific, genotype-specific, or cluster-specific. The use of the term "target" can be applied to indicate one of more specific analytes that one wishes to identify, detect or quantify.

In addition to biological analytes, the fluid sample may contain other non-specific materials such as non-target biological materials and non-biological materials. These non-specific materials are not the object of the determination being performed. Some of these non-specific materials can interfere with or aggregate with analytes to prevent the detection of analytes, causing undesirable false negative detection outcomes. Some of these non-specific materials including non-specific species of the analytes can be falsely detected in the absence of the analytes, causing false positive detection outcomes. As well the total sum of non-specific materials can outnumber the sum of analytes in a sample by several orders of magnitude to create substantial noise that prevents the detection signal generated from the analytes to be distinguished from said noise, causing undesirable false negative or inconclusive detection outcomes.

The level, amount, copies and/or concentration of an analyte can vary greatly in a sample. As would be understood by those skilled in the art, it is much more difficult to identify, detect and quantity low levels of analytes, particularly in the presence of much greater levels of non-specific materials.

The expression "magnetic separation" refers to a process that physically separates analytes from non-specific materials by binding analytes to magnetically extractable particles. The material used for binding analytes with magnetic particles can include antibodies, monoclonal antibodies, polyclonal antibodies, amino acids, peptides, proteins, haptens, nucleic acids, oligonucleotides, DNA, RNA, aptamers, and combinations thereof.

The expression "electrochemical system" refers to a system that determines the presence and/or quantity of a redox analyte through measurements of electrical signal in a solution between a working electrode and a counter electrode, such as induced by a redox reaction or electrical potential from the release or absorption of ions. The redox reaction refers to the loss of electrons (oxidation) or gain of electrons (reduction) that a material undergoes during electrical stimulation such as applying a potential. Redox reactions take place at the working electrode, and which, for chemical detection, is typically constructed from an inert material such as platinum or carbon. The potential of the working electrode is measured against a reference electrode, which is typically a stable, well-behaved electrochemical half-cell such as silver/silver chloride. The electrochemical system can be used to support many different techniques for determining the presence and concentration of the target biomolecules including, but not limited to, various types of voltammetry, amperometry, potentiometry, coulometry, conductometry, and conductimetry such as AC voltammetry, differential pulse voltammetry, square wave voltammetry, electrochemical impedance spectroscopy, anodic stripping voltammetry, cyclic voltammetry, and fast scan cyclic voltammetry. The electrochemical system may further include one or more negative control electrode, and positive control electrode. In the context of the present invention, a single electrochemical system may be used to detect and quantify more than one type of target analyte.

It will be readily understood by those skilled in the art that the amplification methods and devices of embodiments of the present invention may be used in combination with different types of detection devices than the one described above. For example, these can include detection devices that measure changes in electrical properties, light output or absorbance, mass, temperature, and size, shape and conductivity of a conductive channel in a field effect transistor, among others.

Amplification Method

Referring to FIG. 1, a flow chart is shown illustrating the main steps of an embodiment of a method for amplifying the number of one or more analytes in a fluid sample. The method comprising: a) providing a fluid sample 100 that may contain non-specific materials and one or more analytes. b) providing one or more sets of magnetic particles 111, wherein each set comprises a plurality of magnetic particles conjugated with a plurality of an analyte binding material to create analyte-magnetic particle complexes if an associated analyte is present, c) providing one or more sets of nonmagnetic particles 121, wherein each set comprises a plurality of nonmagnetic particles conjugated with a plurality of an analyte binding material and also conjugated with a plurality of detectable tags in greater amounts than the bound associated analyte to create detectable tag-nonmagnetic particle-analyte-magnetic particle sandwiches if an associated analyte is present, and d) unbinding the detectable tags from said sandwiches 132.

In another embodiment, the analyte-magnetic particle complexes in step (b) are magnetically immobilized and the non-magnetically immobilized constituents of the fluid sample which may contain non-specific materials is washed and flushed away 114. In another embodiment the detectable tag-nonmagnetic particle-analyte-magnetic particle sandwiches in step (c) are magnetically immobilized and unbound nonmagnetic particles conjugated with detectable tags are washed and flushed away 124. In yet another embodiment the detectable tag-nonmagnetic particle-analyte-magnetic particle sandwiches in step (d) are magnetically immobilized 134 and the unbound detectable tags are washed and separated from said sandwiches 132.

Figure 2:
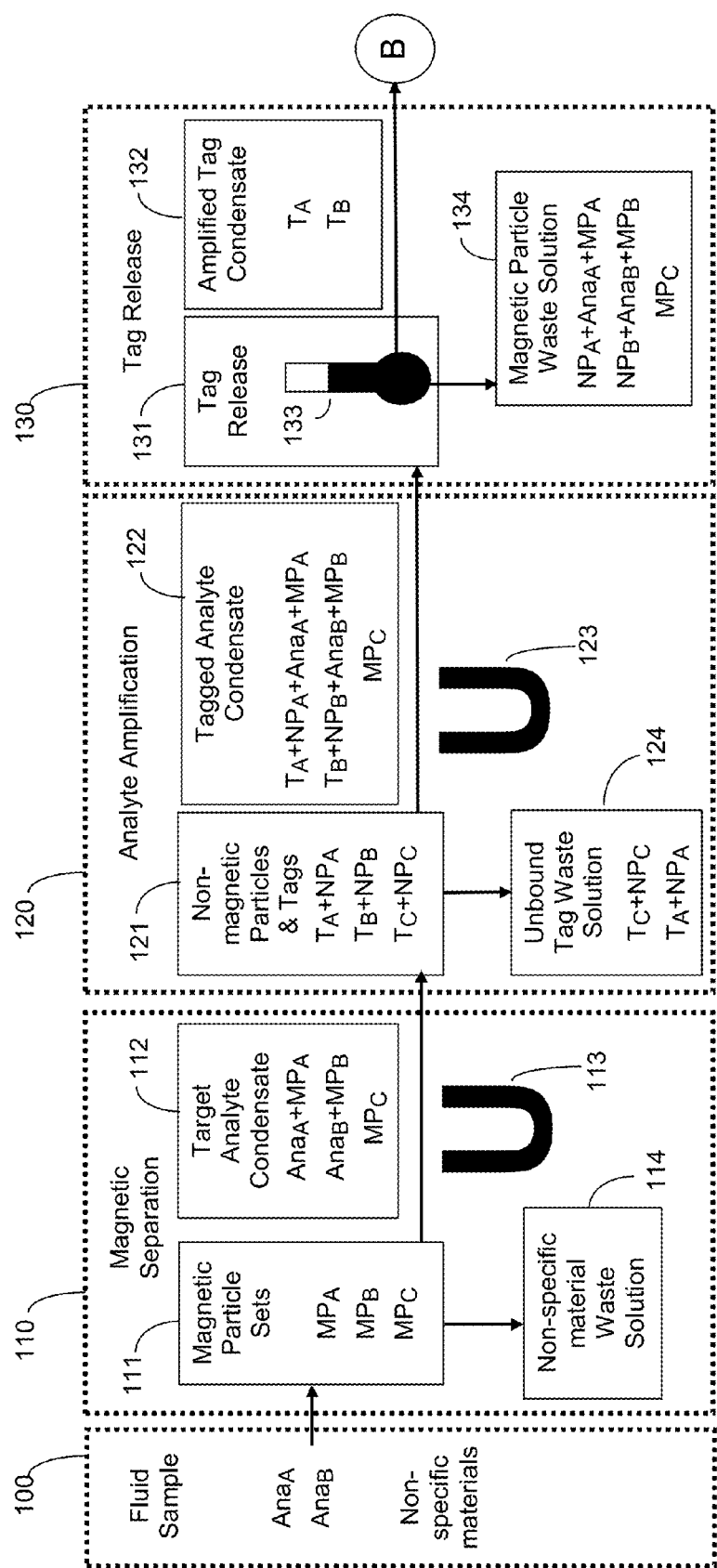
FIG. 2 shows a detailed flow chart illustrating an amplification method according to an embodiment of the present invention.

Referring to FIG. 2, a detailed flow chart is shown illustrating the main steps of an embodiment of an amplification method for amplifying the number of one or more analytes in a fluid sample.

The method first includes a step for extracting analytes from non-specific materials to reduce the incidence of undesirable false negative and false positive detection outcomes. Said method includes a magnetic separation process 110 for separating a fluid sample 100 into a target analyte condensate 112 containing target analytes from the sample, if any, and a non-specific material waste solution 114 containing non-specific materials which are not intended to be detected but can interfere with the detection of analytes.

The fluid sample 100 that may contain non-specific materials and one or more analytes is provided to the magnetic separation process 110. Also provided is one of more sets of magnetic particles 111 wherein each set comprises a plurality of an analyte binding material that conjugates with a target analyte to be detected if the associated analyte is present in the sample. For example a first magnetic particle set $MP_A$ Is associated with extracting target analyte $Ana_A$, a second magnetic particle set $MP_B$ Is associated with extracting target analyte $Ana_B$, and third magnetic particle set $MP_C$ Is associated with extracting target analyte $Ana_C$. In one example, target analyte $Ana_C$ is not present in sample 100.

Figure 3:
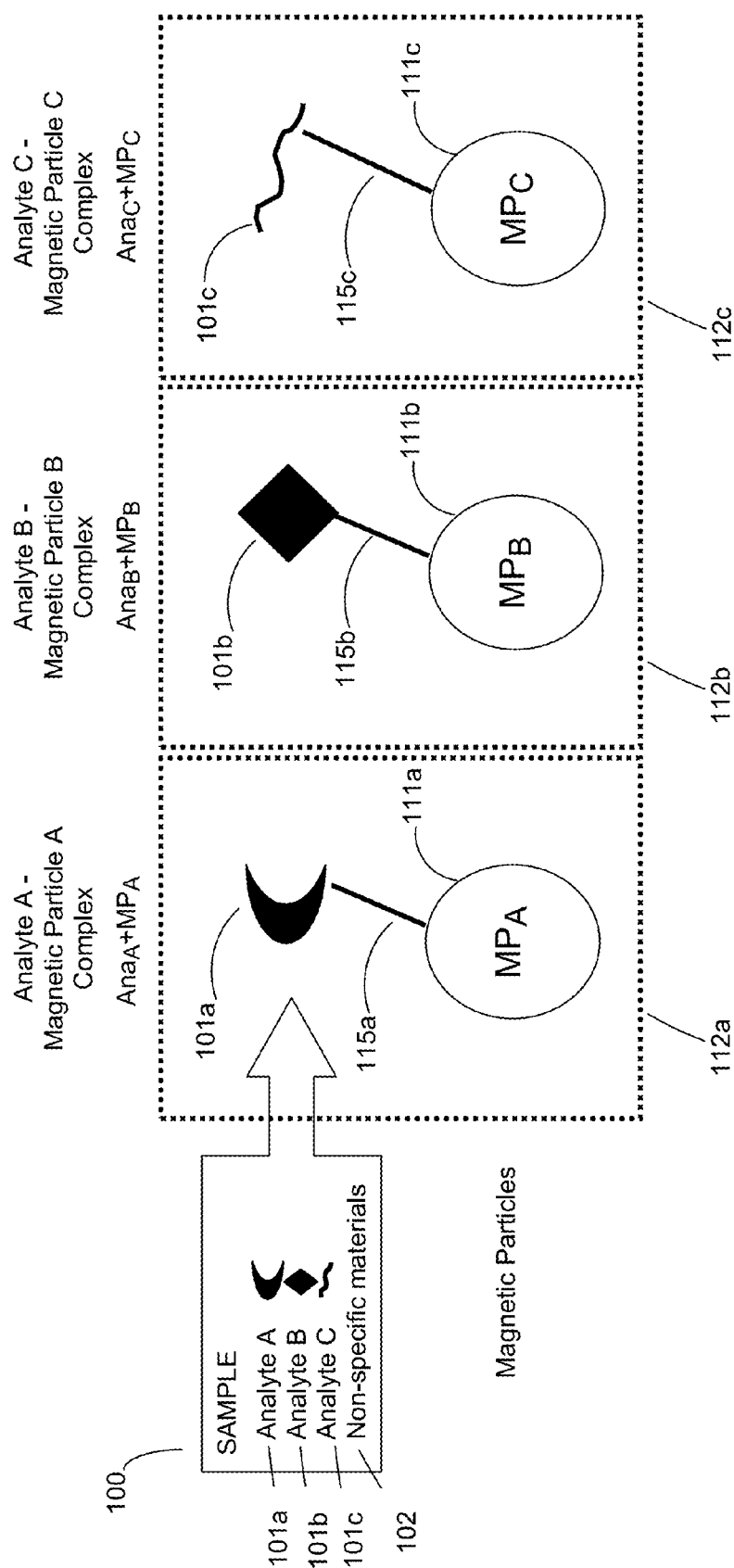
FIG. 3 is a schematic representation of analyte-magnetic particle complexes.

Referring to FIG. 3, as an example, the fluid sample 100 comprises 3 target analytes: microorganism analyte A 101a, protein analyte B 101b, and nucleic acid analyte C 101c along with non-specific materials 102. There is also provided sets of magnetic particles 111a, 111b. 111c. The first magnetic particle set $MP_A$ 111a Is associated with extracting target analyte $Ana_A$ 101a and is conjugated with a suitable analyte binding material 115a. Each set of magnetic particles 111a, 111b, 111c, would have its own analyte binding material 115a, 115b 115c that is used to bind to the associated target analyte. In the case of a cell, virus particle or protein, the analyte binding material can be an antibody, and preferably a highly specific monoclonal antibody. In the case of a nucleic acid the analyte binding material can be a complementary DNA probe. Other analyte binding materials can also be provided. The first magnetic particle set $MP_A$ 111a would form an analyte A-magnetic particle A complex $Ana_A$-$MP_A$ 112a should analyte A 101a be present in the fluid sample and bind with analyte binding material 115a which is conjugated with a first magnetic particle set $MP_A$ 111a. While this example illustrates the presence of 3 sets of magnetic particles associated with three target analytes, it should be clear that a plurality of sets of magnetic particles can be employed for multiplexed and multi-analyte applications. In some embodiments a set of magnetic particles may be associated with a specific analyte. In some embodiments a set of magnetic particles may be associated with a group of multiple analytes. In some embodiments multiple sets of magnetic particles may be associated with a specific analyte. The method described herein can be adapted to a variety of other samples and analyte configurations.

Referring to FIG. 2, the fluid sample 100 and magnetic particle sets 111 are mixed by mechanical agitation, diffusion, or other method. After an allotted time the target analytes will bind with the associated sets of magnetic particles to form target analyte-magnetic particle complexes, if the target analytes are present in the fluid sample. A magnetic field 113 is applied to draw the target analyte-magnetic particle complexes away from non-specific materials and then immobilize the complexes while the remaining non-specific waste solution 114 is flushed away to a waste reservoir. Additional washes can be used. In this example, the target analyte condensate 112 contains magnetic particle complexes for analyte A, $Ana_A$+$MP_A$, and analyte B, $Ana_B$+$MP_B$. Magnetic particles $MP_C$ are also magnetically extracted and contained in the target analyte condensate even though there is no analyte C in the fluid sample.

The magnetic separation step may optionally include one or more steps for pre-treating the fluid sample. In one embodiment, a membrane is used to prevent large materials from entering the mixing chamber.

In another embodiment, a chemical such as an adherent could be employed to remove interfering materials. In another embodiment, a disaggregation technique such as a chemical surfactant, sonication or hydrodynamic cavitation can be employed to disaggregate clumps potentially containing target analytes.

The method next includes a step to provide a greatly increased number of detectable tags per target analyte to improve the ability of detecting low abundance analytes. Said method includes an analyte amplification process 120 for creating a tagged analyte condensate 122 where detectable tags are bound to target analyte-magnetic particle complexes, and an unbound tag waste solution 124 containing left over tags that are not bound to complexes because their corresponding target analytes are not present in fluid sample 100 or are present in a low level so that all analyte-magnetic particle complexes have already been bound to tags.

The target analyte condensate 112 containing target analyte-magnetic particle complexes is provided to the analyte amplification process 120. Also provided is one or more sets of nonmagnetic particles 121, wherein each set comprises a plurality of nonmagnetic particles conjugated with a plurality of an analyte binding material and also conjugated with a plurality of detectable tags in much greater amounts than the associated analyte in the fluid sample. The nonmagnetic particles may be styrene, polymer, glass, ceramic, composite, or other material that can readily conjugate analyte binding materials and detectable tags.

Figure 4:
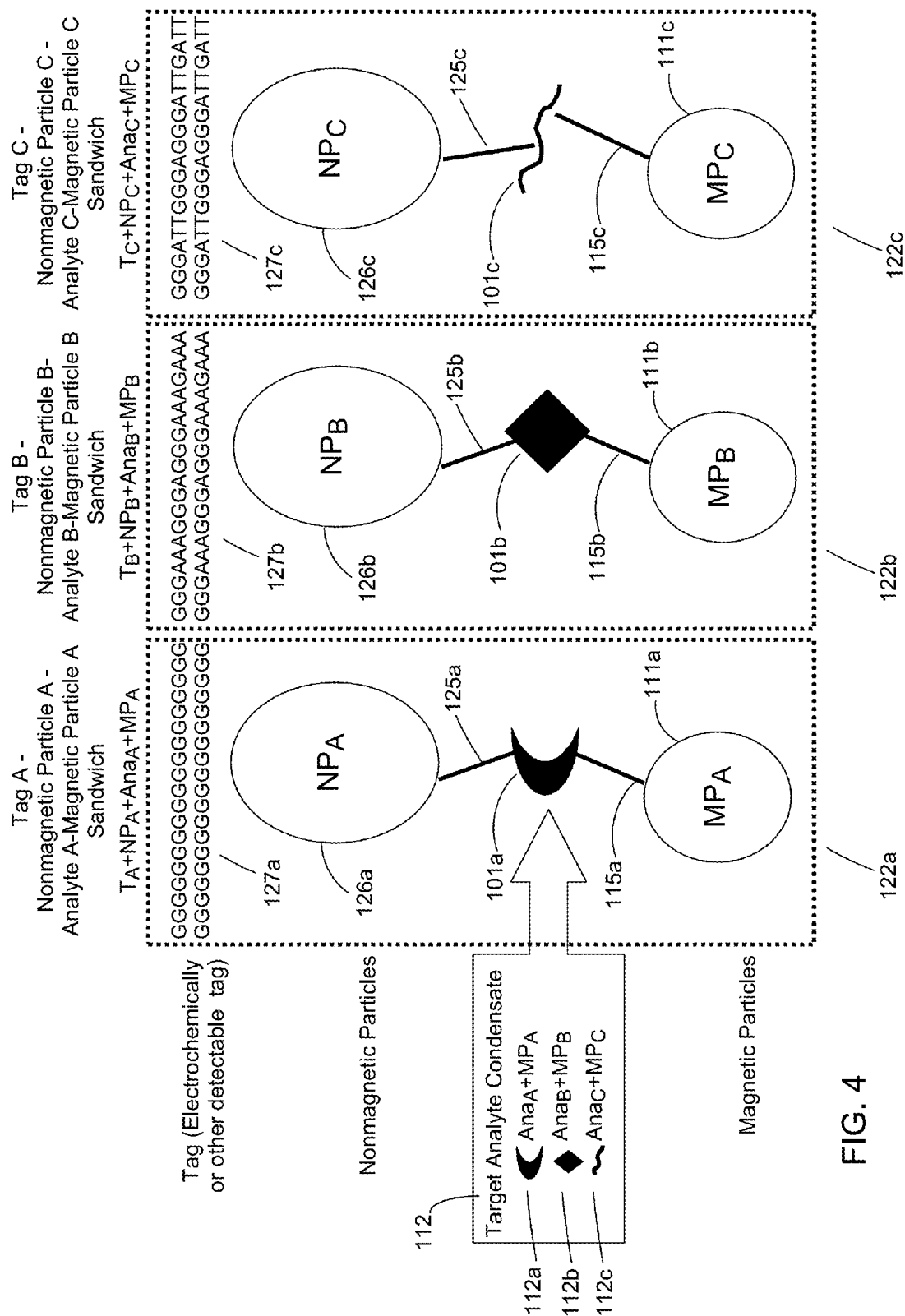
FIG. 4 is a schematic representation of electrochemically detectable tag-nonmagnetic particle-target analyte-magnetic particle sandwiches

Referring to FIG. 4, as an example, the target analyte condensate 112 may contain 3 sets of analyte-magnetic particle complexes 112a, 112b, 112c, associated with three target analytes: microorganism analyte A 101a, protein analyte B 101b and nucleic acid analyte C 101c. There is also provided sets of nonmagnetic particles 126a, 126b. 126c. The first nonmagnetic particle set $NP_A$ 126a Is associated with amplifying target analyte $Ana_A$101a and is conjugated with a suitable analyte binding material 125a which may bind with analyte A 101a conjugated to the analyte A-magnetic particle complex 112a.

Each set of nonmagnetic particles 126a, 126b, 126c, would have its own analyte binding material 125a, 125b 125c that is used to bind to the associated target analyte, and may be the same or different than the analyte binding materials 115a, 115b, 115c, conjugated to the magnetic particles 115a, 115b 115c. In the case of a cell, virus particle or protein, the analyte binding can be an antibody, and preferably a highly specific monoclonal antibody. In the case of a nucleic acid the analyte binding can be a complementary DNA probe. Other analyte binding materials can also be provided.

Said nonmagnetic particle set $NP_A$ 126a is also conjugated with a plurality of detectable tags 127a. Referring to FIG. 4, in one embodiment the tags 127a are electrochemically detectable tags comprising oligonucleotides with 30-500 bases with the majority being guanine. In the event of the determination of multiple target analytes from the same sample, the tags will be slight variations with the majority being guanine in non-random placements of guanine, adenine and thymine 127b, 127c. In another embodiment the tags are detectable by other detection methods which may include detection methods that measure changes in electrical properties, light output or absorbance, mass, temperature, and size, shape and conductivity of a conductive channel in a field effect transistor.

Furthermore referring again to the example where the detectable tags are electrochemically detectable tags, said first nonmagnetic particle set 126a would form an electrochemical tag A-nonmagnetic particle A-analyte A-magnetic particle A sandwich $T_A$–$NP_A$–$Ana_A$–$MP_A$ 122a should analyte A 101a be present in the fluid sample and bind with analyte binding material 115a which is conjugated with a first magnetic particle set $MP_A$ 111a, and analyte binding material 125a which is conjugated with a first nonmagnetic particle set $NP_A$ 126a and linked with a large number of electrochemically detectable tags 127a. While this example illustrates the presence of 3 sets of nonmagnetic particles associated with three target analytes, it should be clear that a plurality of sets of nonmagnetic particles can be employed for multiplexed and multi-analyte applications. The method described herein can be adapted to a variety of other samples, analyte configurations, and types of detectable tags.

Referring to FIG. 2, each nonmagnetic particle set may conjugate to one associated target analyte-magnetic particle complex. In the abovementioned example a first nonmagnetic particle set $NP_A$ Is associated with amplifying target analyte $Ana_A$, a second nonmagnetic particle set $NP_B$ Is associated with amplifying target analyte $Ana_B$, and third nonmagnetic particle set $NP_C$ Is associated with amplifying target analyte $Ana_C$. In this example, target analyte $Ana_C$ is not present in sample 100.

The target analyte condensate 112 and nonmagnetic particle sets 121 are mixed by mechanical agitation, diffusion, or other method. After an allotted time the target analytes bind with the associated sets of nonmagnetic particles to form tag-nonmagnetic particle-target analyte-magnetic particle sandwiches, if the target analyte-magnetic particle complexes are present in the target analyte condensate. A magnetic field 123 is applied to draw the tag-nonmagnetic particle-target analyte-magnetic particle sandwiches away from unbound tags and then immobilize the sandwiches while the remaining unbound tag waste solution 124 is flushed away to a waste reservoir. In the abovementioned example the tagged analyte condensate 122 contains tag-nonmagnetic particle-target analyte-magnetic particle sandwiches for analyte A, $T_A$+$NP_A$+$Ana_A$+$MP_A$ and analyte B, $T_B$+$NP_B$+$Ana_B$+$MP_B$. Magnetic particles $MP_C$ are also magnetically extracted and contained in the tagged analyte condensate even though there is no analyte C in the fluid sample.

The unbound tag waste solution 124 contains unbound tags along with nonmagnetic particles associated with analyte C, $T_C$+$NP_C$, since there is no analyte C-magnetic particle C complexes in the tagged analyte condensate. In this example there is also a low abundance of analyte A in the fluid sample 100. As a consequence, all of the analyte A bound to magnetic particles $Ana_A$+$MP_A$ may be fully bound with tags A-nonmagnetic particles A complexes $T_A$+$NP_A$, leaving a surplus of unbound $T_A$+$NP_A$ complexes. These surplus unbound tags will be flushed to the unbound tag waste solution 124 when the detectable tag-nonmagnetic particle-analyte-magnetic particle sandwiches are magnetically immobilized.

The number of detectable tags must exceed the number of associated target analytes, preferably by several orders of magnitude, in order to amplify the analyte level. In one embodiment there are $10^6$ detectable tags bound to each nonmagnetic particle. Each of the detectable tags contains about 10 guanine molecules from 40 bases of which about 25% are guanine. This produces an amplification ratio of about $1 \times 10^7$ guanine molecules per target analyte. In every situation the amplification ratio of guanine molecules to target analyte needs to be statistically calibrated to account for losses from the magnetic separation process, the analyte binding materials, type and concentration of the target analytes, type and amount of non-specific materials in the sample, etc.

The method next includes a step to unbind the detectable tags from the detectable tag-nonmagnetic particle-analyte-magnetic particle sandwiches and deliver the unbound detectable tags to a detection process. Said method includes a tag release process 130 for creating an amplified tag condensate 132 comprising detectable tags unbound from said sandwiches and a magnetic particle waste solution 134 containing the non-detectable portions of said sandwiches along with magnetic particles associated with analytes not present in fluid sample 100.

The tagged analyte condensate 122 containing sandwiches is provided to the tag release process 130. In the abovementioned example, the tagged analyte condensate 122 contains detectable tag-nonmagnetic particle-target analyte-magnetic particle sandwiches for analyte A, $T_A$+$NP_A$+$Ana_A$+$MP_A$ and analyte B, $T_B$+$NP_B$+$Ana_B$+$MP_B$. Magnetic particles $MP_C$ are also magnetically extracted and contained in the tagged analyte condensate even though there is no analyte C in the fluid sample.

A magnetic field 123 is applied to immobilize the sandwiches and unbound magnetic particles while a tag release system 133 is used to unbind, denature or release the detectable tags bound to the nonmagnetic particles in the sandwiches. In one embodiment a heating element or thermistor may be provided for denaturing oligonucleotide tags from detectable tag-nonmagnetic particle-analyte-magnetic particle sandwiches at an appropriate temperature and for a length of time sufficient to denature the tags. Other processes may be used to unbind tags from the sandwiches and also to prevent the delivery of magnetic particle waste materials to the amplified tag condensate 132.

The unbound tags are washed and discharged to an amplified tag condensate 132. In the abovementioned example the amplified tag condensate 132 contains electrochemically detectable tags for analyte A $T_A$ and analyte B $T_B$. In some embodiments additional processes such as filters and chemicals are provided to prevent materials other than the detectable tags from entering the amplified tag condensate. These unwanted materials may include unwanted sandwich components that become unbound during the denature or release process.

Detection Method

Figure 5:
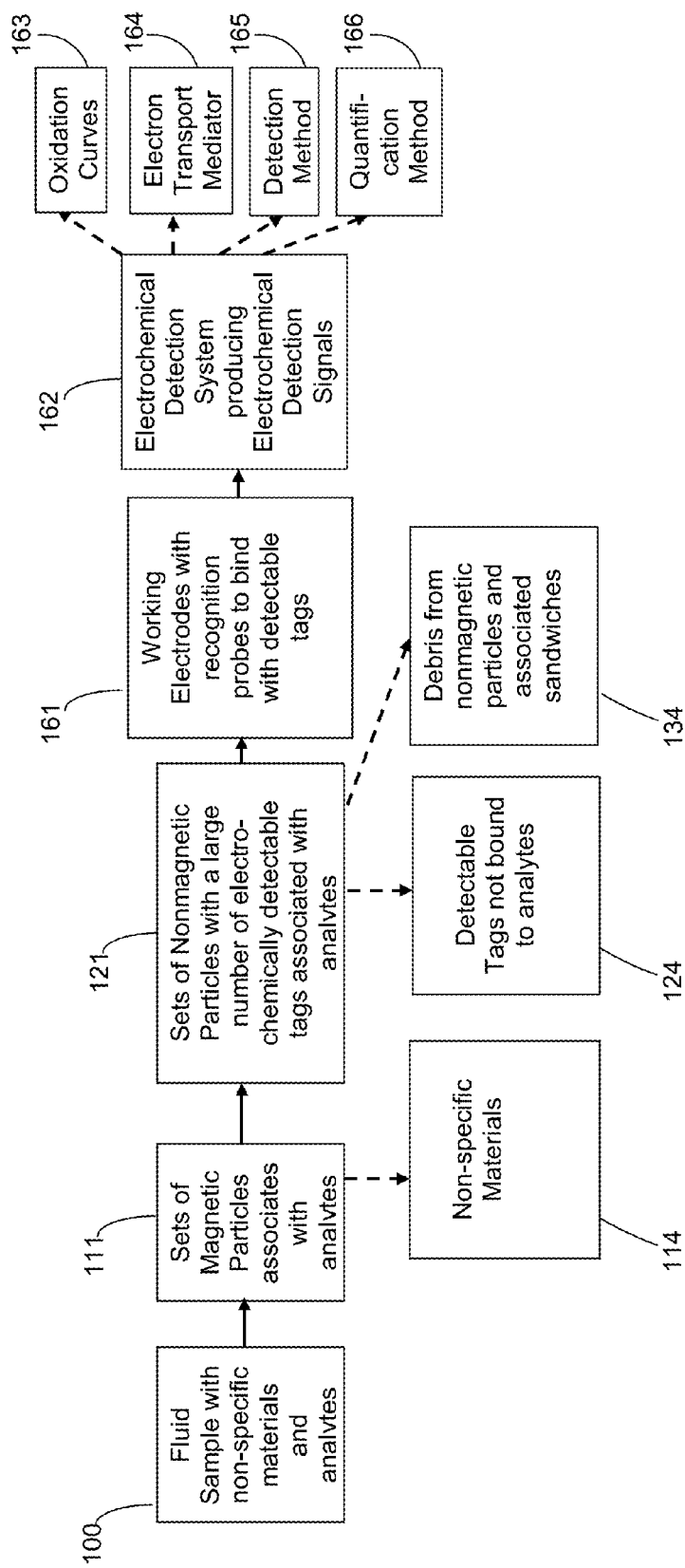
FIG. 5 shows a flow chart generally illustrating a detection method according to an embodiment of the present invention.

Referring to FIG. 5, a flow chart is shown illustrating the main steps of an embodiment of a method for detecting and/or quantifying the level of one or more analytes in a fluid sample. The method comprises: a) providing a fluid sample 100 that may contain non-specific materials and one or more analytes, b) providing one or more sets of magnetic particles 111, wherein each set comprises a plurality of magnetic particles conjugated with a plurality of an analyte binding material to create analyte-magnetic particle complexes if an associated analyte is present, c) providing one or more sets of nonmagnetic particles 121, wherein each set comprises a plurality of nonmagnetic particles conjugated with a plurality of an analyte binding material and also conjugated with a plurality of electrochemically detectable tags in greater amounts than the bound associated analyte to create electrochemically detectable tag-nonmagnetic particle-analyte-magnetic particle sandwiches if an associated analyte is present, and d) providing one or more working electrodes, wherein each working electrode is conjugated with a plurality of a recognition probe to bind with associated electrochemically detectable tags, and an electrochemical detection system that produces electrochemical signals 162 on each working electrode in proportion to the level of an associated analyte if said analyte is present in the fluid sample.

In another embodiment the analyte-magnetic particle complexes in step (b) are magnetically immobilized and the non-magnetically immobilized constituents of the fluid sample that may contain non-specific materials is washed and flushed away 114. In another embodiment the electrochemically detectable tag-nonmagnetic particle-analyte-magnetic particle sandwiches in step (c) are magnetically immobilized and unbound nonmagnetic particles conjugated with electrochemically detectable tags are washed and flushed away 124. In another embodiment after step (c) the electrochemically detectable tag-nonmagnetic particle-analyte-magnetic particle sandwiches are magnetically immobilized 134 and electrochemically detectable tags are unbound from said sandwiches, and washed and delivered to the working electrodes in step (d) 161. In another embodiment the electrochemical detection technique in step (d) generates oxidation curves within a predetermined range and the generated electrochemical signals 162 can be measured from the peak values of an oxidation curve or from the area under an oxidation curve 163. In another embodiment step (d) includes an electron transport mediator 164.

In another embodiment the electrochemical detection technique in step (d) performs a first, a second and a third detection scan with an electron transport mediator, whereby a) the generated signal from guanine oxidation is measured as the difference in peak signal from a first scan minus the signal from a second scan, b) the threshold presence/absence signal is measured as the greatest variation in signal from a second scan minus a third scan, and c) the analyte is determined to be present if the generated signal from the associated electrochemically detectable tags is greater than the threshold presence/absence signal 165.

In another embodiment the electrochemical detection technique in step (d) quantifies the level of an analyte by comparing the generated electrochemical signal from an associated electrochemically detectable tag with predetermined signals from known levels of said analyte 166.

Figure 6:
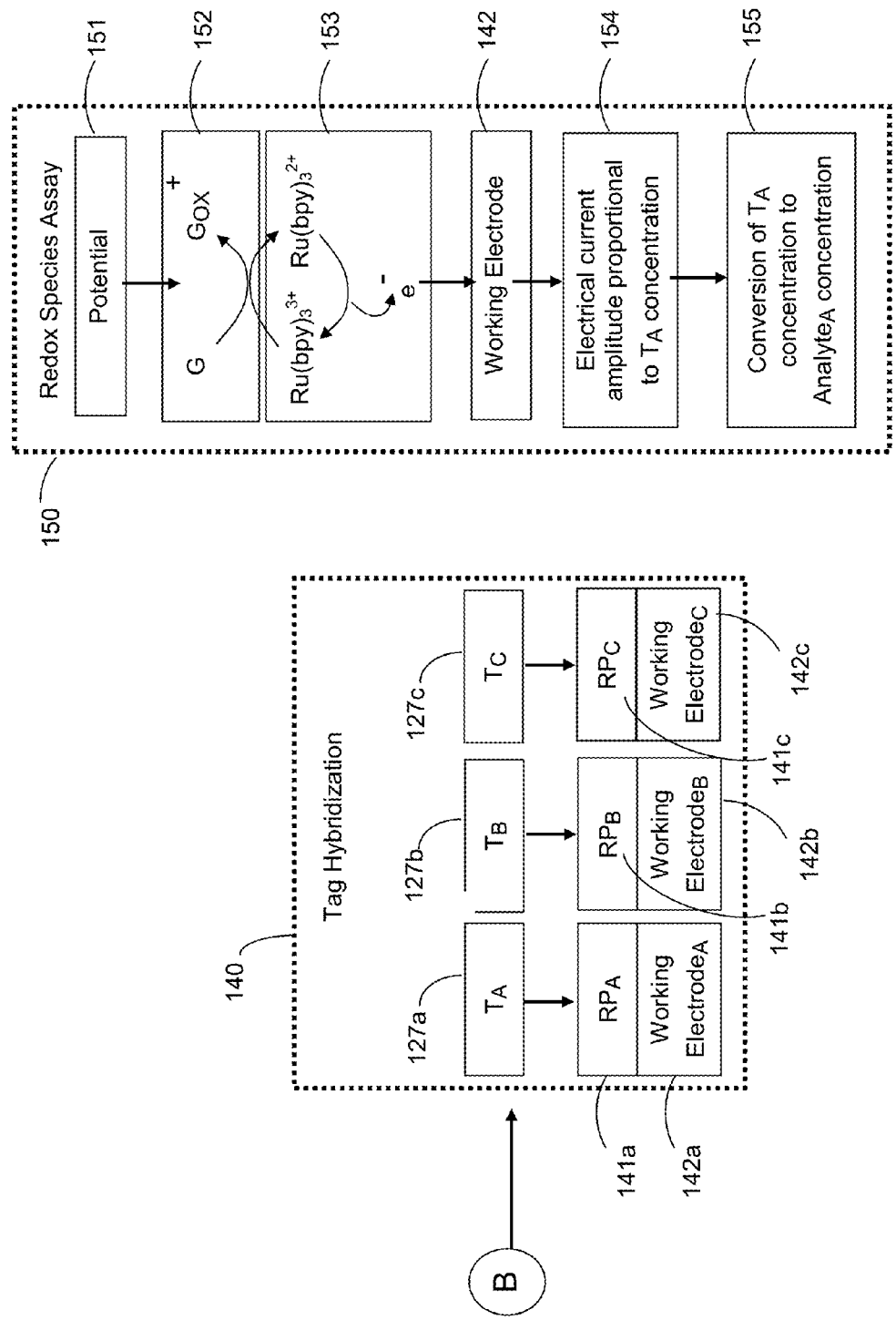

Referring to FIGS. 2 and 6, a detailed flow chart is shown illustrating the main steps of a detection method for detecting and/or quantifying one or more analytes in a fluid sample that are amplified with the amplification method in FIG. 2. As described above, the amplification method may be used with many detection methods. However, when the amplification method is used as part of the detection method referred to in FIGS. 2 and 6, the amplification method makes use of electrochemically detectable tags.

Following the steps in the amplification method referred to in FIG. 2 and described above, the detection method next includes a step to detect and/or quantify the electrochemically detectable tags in the amplified tad condensate 132 being released for detection.

In one embodiment, the method includes a tag hybridization process 140 for creating tag-probe duplexes. The amplified tag condensate 132 from the tag release process 130 is provided to an electrochemical detection system where electrochemically detectable tags 127 hybridize with complementary recognition probes 141 which are attached to electrochemical working electrodes 142. In one embodiment the electrochemically detectable tags 121 are oligonucleotides with the majority being guanine in non-random placements of guanine, adenine and/or thymine, and the recognition probes are oligonucleotides with the majority being cytosine in non-random placements of cytosine, thymine and/or adenine.

Figure 7:
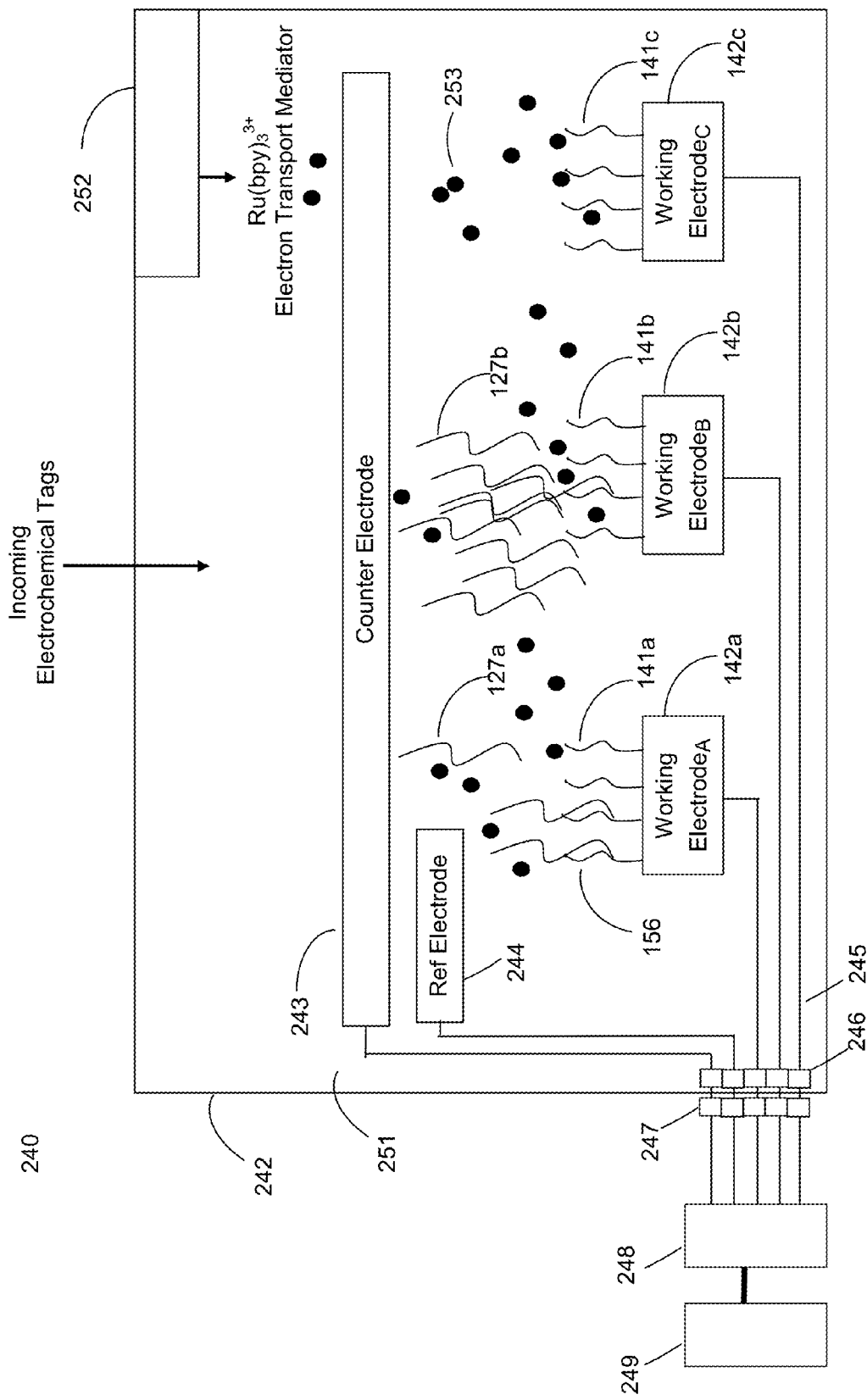
FIG. 7 is a schematic representation of an electrochemical biosensor according to one embodiment of the invention to which the amplified tag condensate may be provided.

Referring to FIG. 7, as an example, an electrochemical detection system may comprise a biosensor providing three working electrodes 142a, 142b, 142c, associated with the detection and/or quantification of three analytes 101a, 101b, 101c. Each working electrode is conjugated with a plurality of recognition probes 141a, 141b, 141c to bind with associated electrochemically detectable tags. The electrochemical detection system further provides a counter electrode 243, a reference electrode 244, a reservoir 252 for providing an electron transport mediator and other required electrochemical selection capabilities will be readily understood by those skilled in the art.

Figure 8:
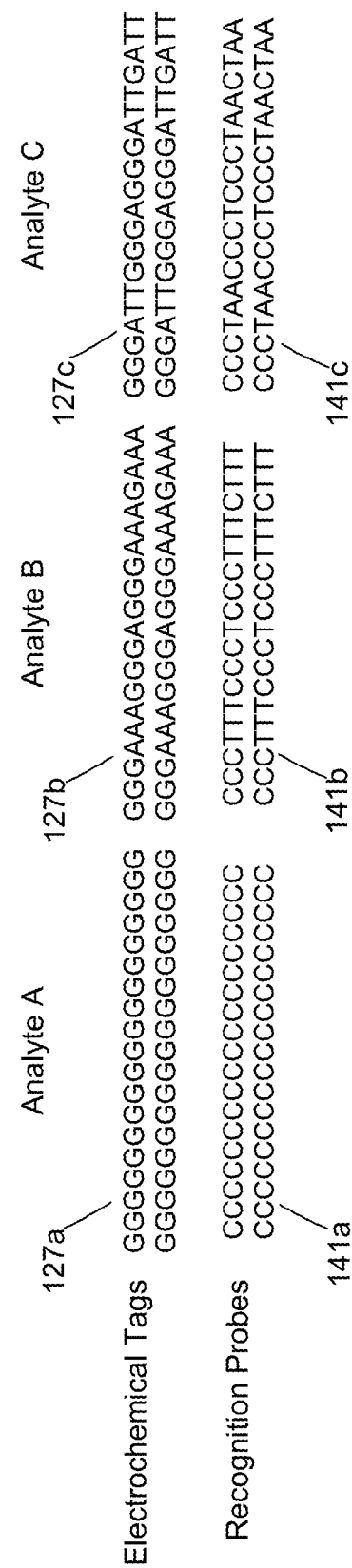
FIG. 8 is a schematic representation of examples of electrochemically detectable tags and complementary recognition probes.

FIG. 8 illustrates an embodiment that provides examples of complementary electrochemically detectable tags and recognition probes containing a non-random sequence of base pairs that can uniquely hybridize with their complements and be used for detecting multiple target analytes A, B and C simultaneously from the same sample. In this embodiment the recognition probes 141a for analyte A are oligonucleotides and comprise 30-500 bases that are primarily cytosine. In the event of the determination of multiple target analytes from the same sample, the recognition probes will be slight variations with the majority of the bases being cytosine in non-random placements of cytosine, thymine and/or adenine 141b, 141c.

As the recognition probes 141a, 141b, 141c . . . have a large amount of cytosine for matching the guanine in the associated tags 127a, 127b, 127c, . . . there is a risk of cross hybridization where some tags may inadvertently hybridize with non complementary probes, such as 127b with 141a. A step may be added to raise the temperature to a value close to but below the melting point of perfect matched hybridization to get rid of the cross hybridization.

Referring to FIGS. 2 and 6, the amplified tag condensate 132 containing unbound electrochemically detectable tags $T_A$ 127a and $T_B$ 127b, associated with analytes $Ana_A$ 101a and $Ana_B$ 101b, are delivered to the working electrodes 142a and 142b. The first set of tags $T_A$ hybridize with its complement recognition probes $RP_A$, and the second set of tags $T_B$ hybridize with its complement recognition probes $RP_B$. Since analyte C $Ana_C$ is absent from the sample 100, its associated tags $T_C$ did not form sandwiches and consequently were removed in the unbound tag waste solution 124.

As a result, there were no tags $T_C$ in the amplified tag condensate. In said example, the associated working electrode 142c is without any electrochemically detectable tags 127c for hybridizing with its recognition probes 141c. Furthermore, there was a low level of $Ana_A$ 101a in the fluid sample 100, and as mentioned above, there is a proportionately low level of associated tags 127a delivered to working electrode A. This allows analyte A to be electrochemically detected but at a lower signal than the more abundant analyte B, reflecting the relative levels of the analytes. The method described herein can be adapted to a variety of other electrode configurations including the use of positive and negative control electrodes, as will be readily understood by those skilled in the art.

In one embodiment electrochemically detectable tags from the amplified tag condensate are delivered to the working electrodes and then are mechanically agitated repeatedly back and forth from one working electrode to the next. This provides contact between complementary tags and recognition probes to allow hybridization to take place. In another embodiment electrophoresis may be used in addition to or instead of agitating the fluid back and forth, to facilitate hybridization through the motion of dispersed tags under the influence of a spatially uniform electric field. In every case, a sufficient contact time is provided to permit hybridization to take place.

The method next includes a step for electrochemically determining the presence and/or level of electrochemically detectable tags in the amplified tag condensate which can then correlate to the presence and/or level of associated analytes in the fluid sample. In one embodiment, a tag detection process 150 employs an amperometric measurement technique. But as will be readily understood by those skilled in the art, the detection process can readily be adapted to support other electrochemical detection techniques such as voltammetry, potentiometry, coulometry, and conductimetry, AC voltammetry, differential pulse voltammetry, square wave voltammetry, electrochemical impedance spectroscopy, anodic stripping voltammetry, cyclic voltammetry, or fast scan cyclic voltammetry.

Referring to FIGS. 6 and 7, in one embodiment an amperometric measurement technique applies a potential scan 151 across a range of potentials to create an electrical current flowing between a counter electrode 243 and one or more working electrodes 142 through a liquid solution 251. In some embodiments the liquid solution contains an electron transport mediator 253. In one embodiment the electron transport mediator is the metal tris(2,2'-bipyridyl)ruthenium (II) complex or Ruthenium bipyridine or $Ru(bpy)_3^{2+}$. The electron transport mediator oxidizes when potential is applied and electrical signals are generated at each working electrode due to the ions from the mediator being attracted to the working electrodes. A peak current is generated at approximately 1.04 V. Ion binding from the mediator is reversible and releases from the working electrodes with a reduction scan after the oxidation scan, which can be repeatedly oxidized and subsequently reduced.

In the case of analytes, guanine is a natural constituent of DNA and RNA and oxidizes at around 1.04 V for all types of analytes. When natural or synthetic guanine is in close proximity to a working electrode and an electrochemical detection technique is applied, guanine will be oxidized, and in the presence of sufficient ruthenium bipyridine analyte, guanine electrons generated from oxidation 152 are transported by the Ruthenium bipyridine analyte 153 to the working electrode surface 142. This provides an incremental electrical current due to guanine oxidation which is measured at the same time as the Ruthenium bipyridine oxidation current. Unlike Ruthenium bipyridine, guanine oxidation is not reversible and will not be able to be reduced to regain its lost electrons. Therefore subsequent potential scans of the analyte will only provide electrical current from Ruthenium bipyridine oxidation. In this way, the electrical current generated from the presence of guanine tags can be determined by measuring the peak current from a first scan produced from guanine oxidation and Ruthenium bipyridine oxidation, minus a second scan produced only from Ruthenium bipyridine oxidation.

In one embodiment, differential pulse voltammetry is used with applied potential from 0.50 volts to 1.20 volts, a pulse size of 20 mV, a step size of 5 mV, sample time of 1.5 seconds and pulse time of 0.1 seconds to each working electrode. Referring to FIG. 9, the method includes performing a first 10, a second 20 and a third 30 potential scan, during which the potential is applied and varied within a predetermined range in a same manner for each scan. In said embodiment, for each scan a potential is applied by the measurement electronics on the working electrodes. During each scan, the change of electrical signal such as current is measured at each working electrode. The peak currents at around 1.04 V from a first 10 and a second 20 potential scan are used to determine the signal from guanine oxidation in the electrochemically detectable tags as the peak current in the first scan 11 minus the peak current in the second scan 21, where the first scan 11 comprises the generated electrical current from guanine oxidation and Ruthenium bipyridine oxidation, and the second scan 21 comprises the generated electrical current from only Ruthenium bipyridine oxidation, the different being guanine oxidation current 41.

Data points can also be used to determine the presence/absence threshold for detecting guanine oxidation in the tags. In the event that there is no guanine attached to a working electrode due to the absence of an associated analyte in a sample 100, there will be no incremental current or signal from guanine oxidation. However, there may be noise produced from the Ruthenium bipyridine mediator and potentially other materials. The method provides data points for determining the variability or noise produced by the Ruthenium bipyridine which is used as the threshold presence/absence current which needs to be exceeded if the target analyte is present and its associated tags generate incremental electrical current from guanine oxidation. The presence/absence threshold is determined in two successive Ruthenium bipyridine potential scans 20 and 30 as the greatest variability 42 at a potential 22 minus 32. Therefore the guanine tags (and associated analytes) are present in sample 100 when the peak guanine oxidation current 41 is greater than the presence/absence threshold current 42. Alternatively, fluctuations of the background noise over different potentials can be accounted for and the threshold detection limit set to three times the standard deviation of the background noise signal amplitude weighted average.

Optionally, the method above may include determining the level or concentration of each target analyte detected in the solution using a comparison of the measured changes of electrical signal from the corresponding working electrodes with predetermined values from samples of known levels of these target analytes. The level of target analytes is related to the level of guanine molecules from the associated detectable tags. Referring to FIG. 10, in one embodiment, a linear relationship 50 is established between peak signals 1, such as current, and analyte levels. At least two standard predetermined signal values 51, 52, . . . could be used to obtain such a relationship. For example, the level of a given type of target analytes may be set equal to the peak signal from the corresponding working electrode multiplied by the ratio of the level of Standard 1 minus the level of Standard 2, divided by the peak signal of Standard 1 minus the peak signal of Standard 2. In another embodiment, a nonlinear relationship such as a logarithmic relationship can exist between peak signals and analyte levels. In this embodiment a suitable formula would be determined for extrapolating peak signals into the levels or concentrations.

The method above could be adapted for use with a different number and configuration of working electrodes. For example, electrical signals from more than one working electrode could be obtained and combined to increase detection of a given type of target analytes. Electrical signals from one or more working electrodes could also be factored in the calculation of the background or threshold limit. In any embodiment, the current may be normalized. But as will be readily understood by those skilled in the art, many variation for determining analyte presence and/or concentration can readily be adapted depending on the detection technique.

Delivery System

With reference to FIGS. 11A, 11B, 11C and 11D, illustrations are shown of a structure for delivering a plurality of an analyte binding material and also a plurality of detectable tags in greater amounts than an associated analyte that may be bound to an analyte binding material. The structure first provides a substrate, such as a nonmagnetic particle 126. The shape of the substrate may be a sphere, a rod, a plate, a disk, a dendrimer, or other shape having a surface which can be used to bind with a plurality of an analyte binding material such antibodies, and also a plurality of detectable tags such as oligonucleotides. The structure next provides a plurality of an analyte binding material 127, and a plurality of a detectable tag 125 which are bound to the surface of the substance 126. As illustrated in FIG. 11B, in some embodiments the substance has a smooth surface. As illustrated in FIG. 11C, in some embodiments the surface is rough or porous in order to increase the surface area for binding a greater number of detectable tags and analyte binding materials.

In some embodiments, the structure's material is agarose, silica, polymer, glass, composite or other material which has suitable chemical processes for attaching analyte binding materials and detectable tags. In some embodiments which provide magnetic materials for magnetic separation as described above, the substrates 126 are nonmagnetic materials.

As illustrated in FIG. 11D, in some embodiments a plurality of an analyte binding material 127 are bound to the surface of the substance 126, and a plurality of a detectable tag 125 are provided inside a hollow substrate 126. In these embodiments, the substrates can be opened during a tag release process in order to release the detectable tags.

Sandwich Structure

Figure 12:
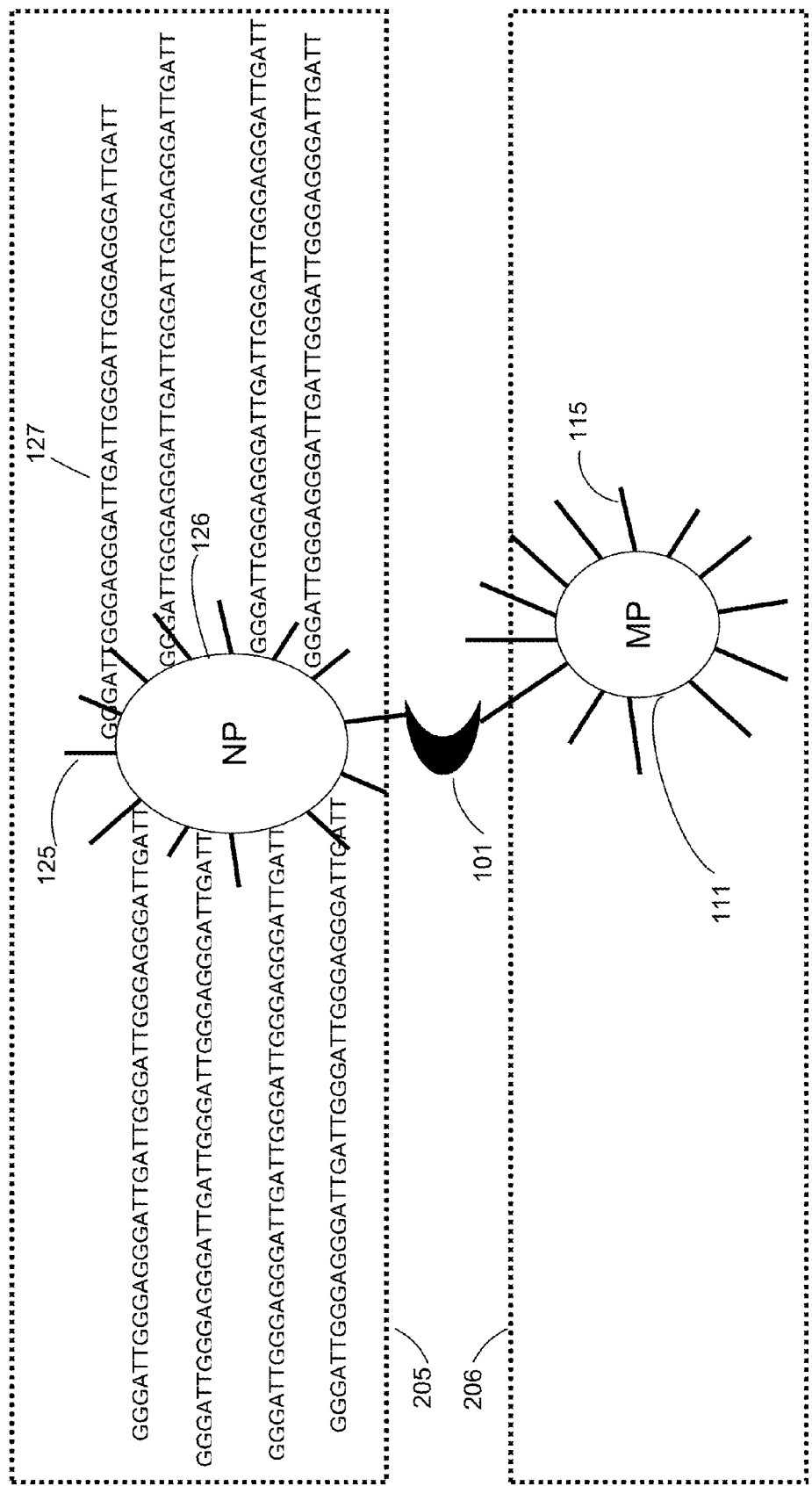
FIG. 12 is a schematic representation of an electrochemically detectable tag-nonmagnetic particle-analyte-magnetic particle sandwich.

With reference to FIG. 12, an illustration is shown of a structure for amplifying the number of analytes in a fluid sample. The structure first comprises an outer layer 205 comprising a nonmagnetic particle 126 conjugated with a plurality of an analyte binding material 125 and also conjugated with a plurality of detectable tags 127 in greater amounts than the bound associated analyte. The structure next comprises an inner layer comprising an analyte 101. The structure further provides an outer layer 206 comprising a magnetic particle 111 conjugated with a plurality of an analyte binding material 115.

In some embodiments the analyte binding materials 125 and 115 are highly specific monoclonal antibodies for proteins, cells, and virus particles, and oligonucleotides for nucleic acid targets. However, the analyte binding materials can be antibodies, monoclonal antibodies, polyclonal antibodies, amino acids, peptides, proteins, haptens, nucleic acids, oligonucleotides, DNA, RNA, aptamers or combinations thereof.

The analyte binding materials 125 on the nonmagnetic particles can be the same as the analyte binding materials 115 on the magnetic particles, but normally are different. For example, antibodies would be selected based on the highest specificity that can be achieved for binding with the target analyte along with a low cross reactivity with non-specific materials including non-specific strains or species of a target analyte. A different antibody on the nonmagnetic particles would avoid the potential problem of the binding site being fully taken by the first antibody on magnetic particles.

A unique aspect of this amplification invention is the ability of the sandwich structure to improve the detection limit of a device used to detect the targets. In one embodiment each nonmagnetic particle is conjugated with monoclonal antibodies and $10^6$ electrochemically detectable tags. Each of the detectable tags contains about 10 guanine molecules from 40 bases of which about 25% are guanine. This produces an amplification ratio of about $1\times10^7$ guanine molecules per target analyte with the potential to amplify the number of analytes in the sample by up to 10,000,000 times. The actual amplification needs to be validated for the number of individual analytes that bind with a unique nonmagnetic particle and a unique magnetic particle. Ideally each target analyte could bind with a unique nonmagnetic particle. But statistically, some targets may bind with multiple nonmagnetic particles and there is also the possibility that some targets will not bind to any nonmagnetic particles. So statistically it is likely that there will be a reduced average yield of targets linked to unique detectable tag-nonmagnetic particle complexes forming the sandwich.

The amplification ratio of guanine molecules per target analyte is limited by the size of the particle that is used. A larger particle will be able to bind with a larger number of tags. In addition it is possible to temporarily place the detectable tags on the inside of the delivery system or attach secondary structures to the nonmagnetic particles to further increase the available surface area. All of the factors impacting the tag amplification ratio need to be developed and validated for specific applications.

Amplification Device

Figure 13:
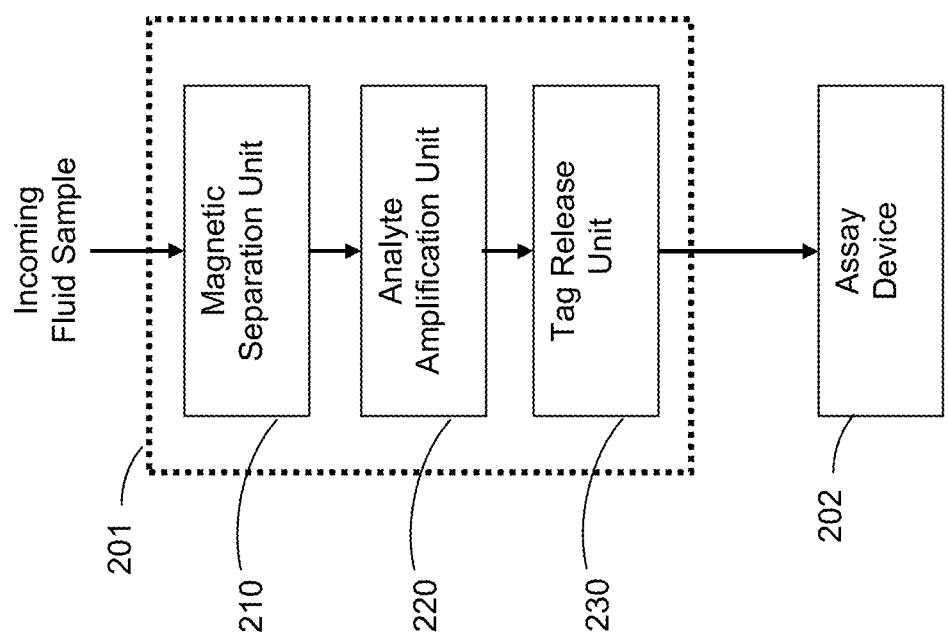
FIG. 13 is a schematic representation of the main units of an analyte amplification device according to an embodiment of the present invention.

With reference to FIG. 13, the main units are shown of a device 201 for amplifying one or more target analytes in a fluid sample according to an embodiment of the invention.

The device first includes a magnetic separation unit 210 comprising one or more sets of magnetic particles, wherein each set comprises a plurality of magnetic particles conjugated with a plurality of an analyte binding material to create analyte-magnetic particle complexes if an associated analyte is present. The magnetic separation unit also comprises a magnet for magnetically extracting said complexes. An incoming fluid sample that may contain non-specific materials and one or more analytes is separated into a target analyte condensate containing said complexes and a non-specific waste solution containing non-specific materials that could interfere with detection or cause false detection outcomes.

The device next includes an analyte amplification unit 220 comprising one or more sets of nonmagnetic particles, wherein each set comprises a plurality of nonmagnetic particles conjugated with a plurality of an analyte binding material and also conjugated with a plurality of detectable tags in greater amounts than the bound associated analyte to create detectable tag-nonmagnetic particle-analyte-magnetic particle sandwiches if an associated analyte is present. The analyte amplification unit also comprises a magnet for magnetically extracting said sandwiches. An incoming target analyte condensate containing said analytes is separated into a tagged analyte condensate containing the formed sandwiches with an amplified number of detectable tags per analyte and a waste solution containing unbound tags that do not link to associated target analytes because the analytes are absent from the fluid sample or already bound other sandwiches.

The device also includes a tag release unit 230 comprising a system for unbinding the detectable tags from the tag-nonmagnetic particle-target analyte-magnetic particle sandwiches, and a magnet for immobilizing the remaining constituents of the sandwiches while the unbound tags are washed and flushed away. An incoming tagged analyte condensate containing an amplified number of detectable tags is separated into an amplified tag condensate containing the released tags and a waste solution containing debris from nonmagnetic particles and associated sandwiches.

Magnetic Separation Unit

Figure 14:
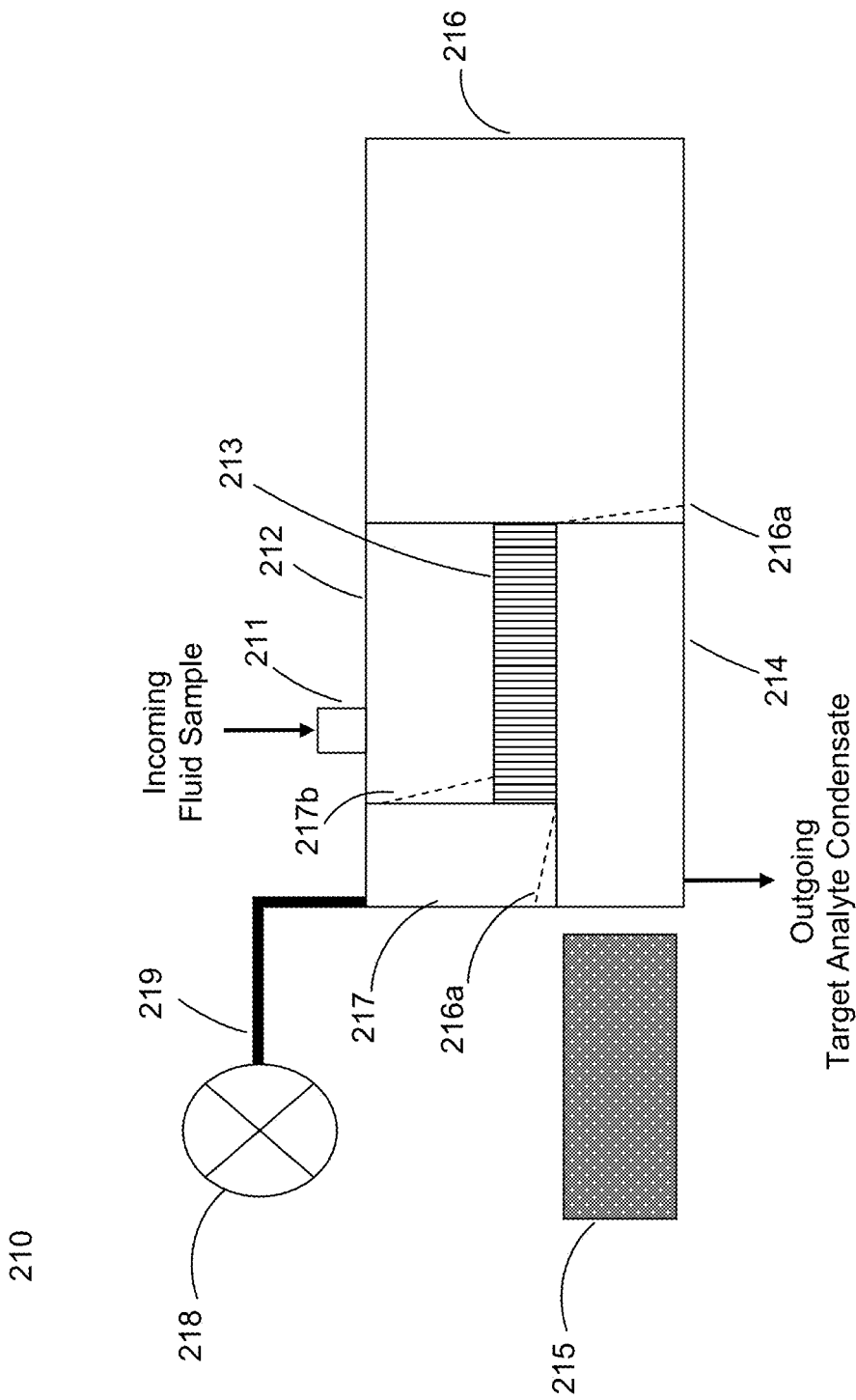
FIG. 14 is a schematic representation of a magnetic separation unit according to one embodiment of the invention.

With reference to FIG. 14, there is shown a magnetic separation unit 210 according to an embodiment of the invention. The incoming fluid sample is placed into an inlet 211 and fills an input reservoir 212. In one embodiment, the fluid sample is mechanically pushed or pulled through a membrane 213 into a mixing chamber 214 in order to filter out larger non-specific materials that could interfere with the amplification and detection processes. In one embodiment as an example, the fluid sample is 1 mL of whole blood and the target analytes are virus particles and RNA both of which are under 100 nm in size. The membrane provides pores that are 250 nm in diameter to prevent larger non-specific materials such as bacteria from entering the mixing chamber. The input reservoir may be modified to accommodate smaller and larger sample volumes, as well as different fluids or liquefied solids.

In another embodiment, a disaggregation system is provided before the filter to break up clumps that may encapsulate the target analytes and prevent targets from being amplified and detected. Examples include sonication and hydrodynamic cavitation. Other configurations can be provided depending on the type of sample, the sample volume, the size of the target analytes and the size of the non-specific materials in the fluid sample, and may not employ a filter or disaggregation system. Additional chambers can also be provided.

In one embodiment, magnetic separation takes place in the mixing chamber 214 which is preloaded with one or more sets of magnetic particles. Each set of magnetic particles is conjugated with a plurality of an analyte binding material associated with a target analyte. It is desirable to select analyte binding materials such as monoclonal antibodies and DNA that are highly specific to the target analyte that have little or no cross reactivity with non-specific materials belonging to the same species or strains of the target analyte.

When the analyte binding material comes in close proximity with the associated target analyte, the analyte binds with the analyte binding material on the magnetic particles, forming analyte-magnetic particle complexes. In one embodiment the contact time between the fluid sample and sets of magnetic particles is 20 minutes. Times could vary depending on the application, analyte binding effectiveness, sample types, sample volume, target analyte concentrations, types and levels of non-specific materials, environmental conditions, and the number of magnetic particles, with longer contact times typically providing a higher recovery of target analytes.

The magnetic separation unit further provides a magnet 215 which is applied to the analyte-magnetic particle complexes in mixing chamber 214. The magnet could be a permanent magnet or electromagnet that is activated to create a magnetic field for drawing and immobilizing the complexes to a portion of mixing chamber. During magnetic activation, the non-specific materials are not attached to magnetic particles and are not drawn by the magnetic field. As a consequence the non-specific materials may be flushed out of the mixing chamber 214 into a waste reservoir 216 when valve 216a is opened. One or more rinses can be used to wash and further flush away non-specific materials using rinsing agents provided in reservoir 217. A mechanical mechanism 218 such as a pump is provided and is in fluid communication 219 with the magnetic separation unit to facilitate the movement of fluids. The resulting target analyte condensate is provided to the analyte amplification unit.

Analyte Amplification Unit

Figure 15:
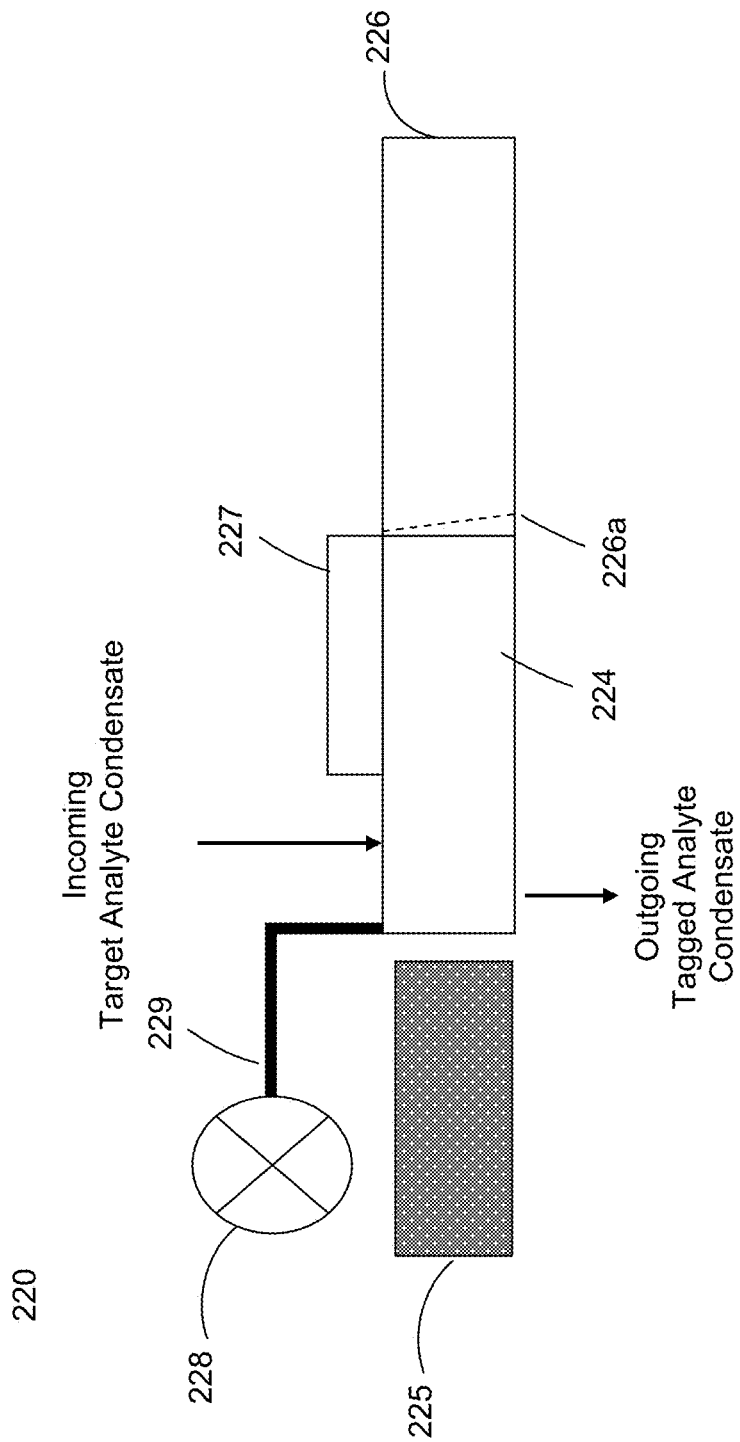
FIG. 15 is a schematic representation of an analyte amplification unit according to one embodiment of the invention.

With reference to FIG. 15, there is shown an analyte amplification unit 220 according to an embodiment of the invention. In one embodiment, the incoming target analyte condensate fills a mixing chamber 224 which is preloaded with one or more sets of nonmagnetic particles. Each set of nonmagnetic particles is conjugated with a plurality of an analyte binding material associated with a target analyte and also conjugated with a plurality of detectable tags in much greater quantity than the associated analyte. When the analyte binding materials on a nonmagnetic particle come in close proximity with an associated analyte on an analyte-magnetic particle complex, the analyte binds with the nonmagnetic particles, forming detectable tag-nonmagnetic particle-analyte-magnetic particle sandwiches. In one embodiment the contact time between a target analyte condensate and sets of nonmagnetic particles is 20 minutes.

The analyte amplification unit further provides a magnet 225 which is applied to the detectable tag-nonmagnetic particle-analyte-magnetic particle sandwiches in mixing chamber 224. The magnet could be a permanent magnet or electromagnet that is activated to create a magnetic field for magnetically drawing and immobilizing the sandwiches to a portion of mixing chamber. In one embodiment the magnet 225 is the same magnet 215 from the magnetic separation unit. During magnetic activation, some of the detectable tags bound to nonmagnetic particles do not bind with associated target analytes attached to magnetic particles and are not drawn by the magnetic field. This may be due to the absence of the associated analyte or a low level of associated analytes which are already bound to other nonmagnetic particles. As a consequence the unbound tags may be flushed out of the mixing chamber 224 into a waste reservoir 226 when valve 226a is opened. One or more rinses can be used to further wash and flush away unbound tags using rinsing agents provided in reservoir 227. A mechanical mechanism 228 such as a pump is provided and is in fluid communication 229 with the analyte amplification unit to facilitate the movement of fluids. The resulting tagged analyte condensate is provided to the tag release unit.

A unique aspect of this invention is the ability to improve the detection limit of the device used to detect the targets. This is achieved by increasing the amplification ratio of guanine molecules per target analyte for electrochemical detection applications. For all other applications the detection limit can be improved by increasing the number of detectable tags per target analyte.

Tag Release Unit

Figure 16:
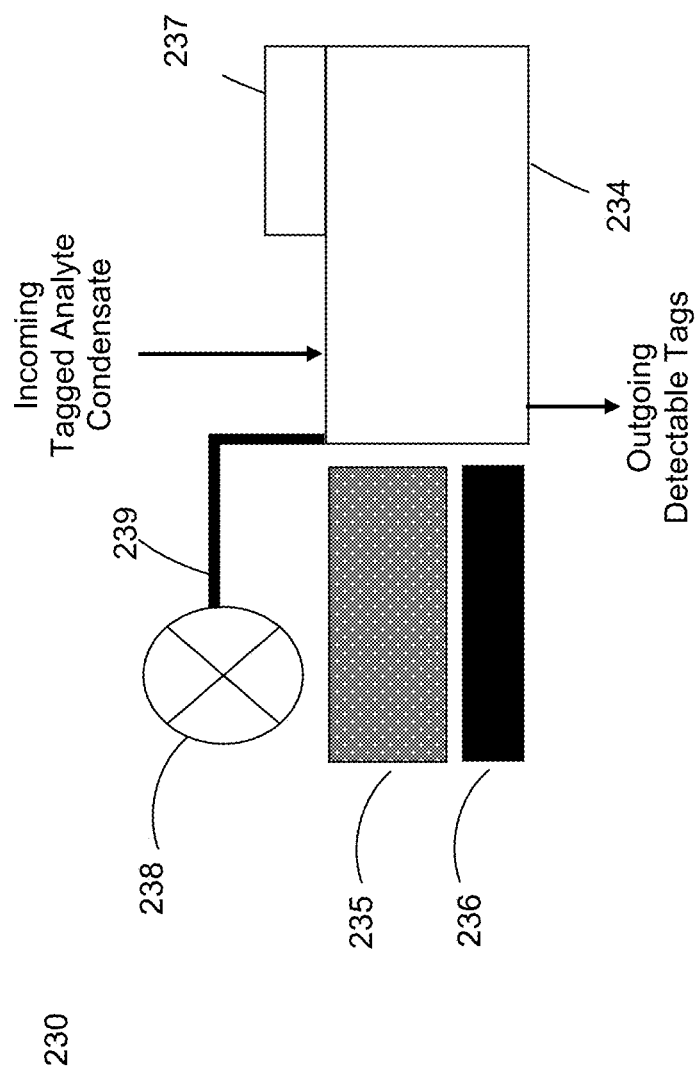
FIG. 16 is a schematic representation of a tag release unit according to one embodiment of the invention.

With reference to FIG. 16, there is shown a tag release unit 230 according to an embodiment of the invention. In one embodiment, the incoming tagged target condensate fills a mixing chamber 234. The tag release unit further provides a magnet 235 which is applied to the detectable tag-non-magnetic particle-analyte-magnetic particle sandwiches in mixing chamber 234. The magnet could be a permanent magnet or electromagnet that is activated to create a magnetic field for drawing the sandwiches to a portion of the chamber. In another embodiment the magnet could be the same magnet 225 or 215 contained in one of the other device units. During magnetic activation, the sandwiches are drawn by a magnetic field to a side of chamber 234.

There is also provided a tag release system 236, such as a heating element or thermistor, that heats the magnetically immobilized sandwiches to about 70° C. or higher to permit denaturing and unfolding of oligonucleotide tags. Other tag release methods can be used in addition to or instead of heating depending on the type of tags and binding materials. A rinse solution from rinse reservoir 237 is used to wash and flush the detectable tags out of the mixing chamber to provide an amplified tag condensate for the detection system. One or more rinses can be used. A mechanical mechanism 238 such as a pump is provided and is in fluid communications 239 with the tag release unit to facilitate the movement of fluids. Once the sandwiches are rinsed, the resulting amplified tag condensate is provided to the detection unit. A filter can optionally be added to prevent any unwanted sandwich materials from leaving the tag release unit along with the tags.

Biosensor

Figure 17:
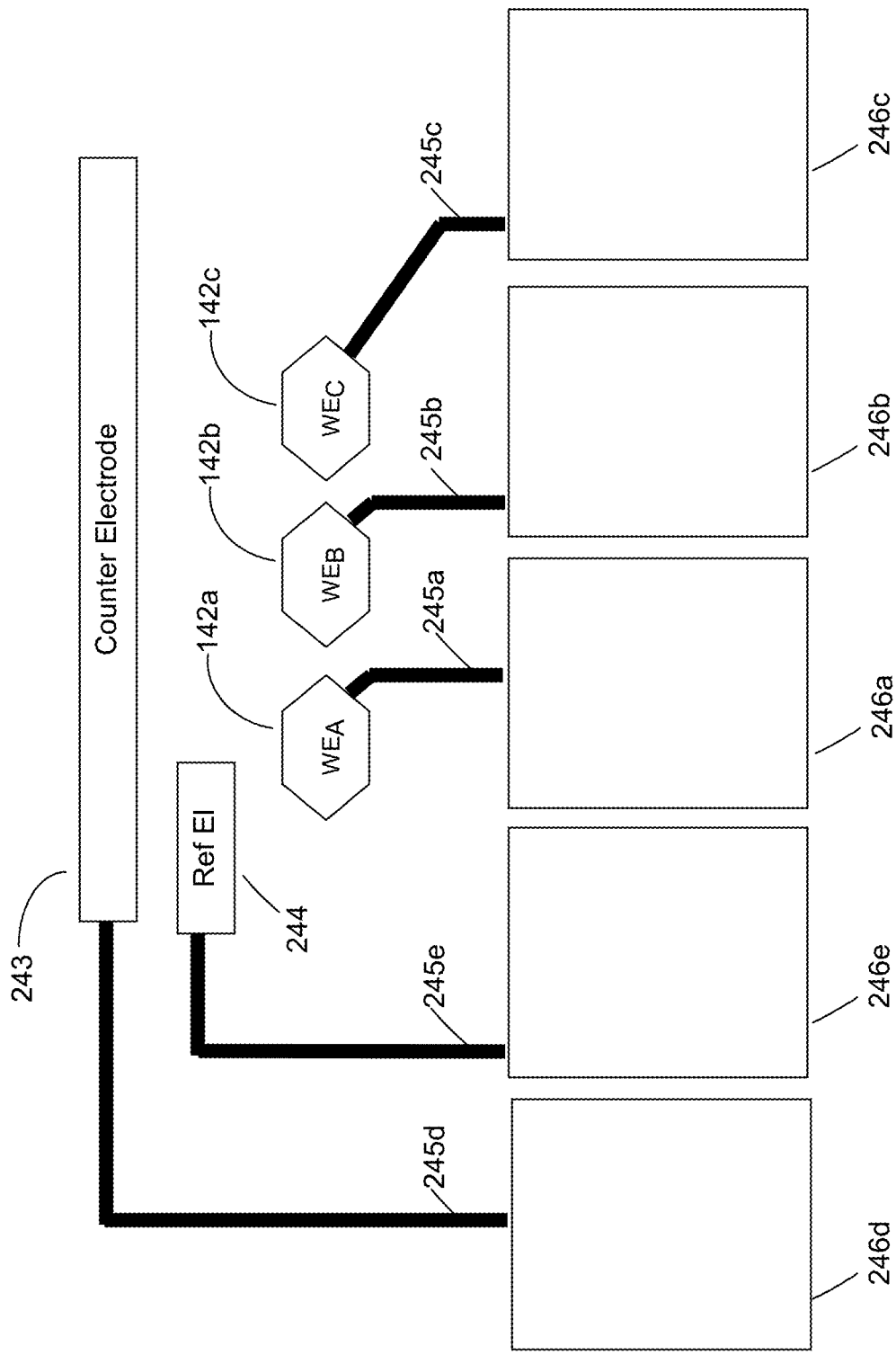
FIG. 17 is a schematic representation of an electrochemical biosensor according to one embodiment of the invention.

With reference to FIG. 17, an illustration is shown of a biosensor for detecting and/or quantifying the level of one or more analytes in a fluid sample. The biosensor first comprises one or more working electrodes 142, a counter electrode 243, a reference electrode 244, and connections to an electrochemical detection system 246.

A unique aspect of this invention is the shape of the electrode surface which facilitates hybridization or other types of binding by maximizing the physical contact between recognition probes and electrochemically detectable tags. Referring to FIG. 17, in one embodiment the working electrode shape is diamond or oblong and the working electrodes 142 are placed in a 1×n series. The electrochemically detectable tags are directed in the fluid to move across the surfaces of the working electrodes back and forth in contact with the recognition probes to allow a longer contact time compared with other shapes or placement of the working electrodes. In another embodiment, the electrochemical detection unit employs electrophoresis to electrically draw the electrochemically detectable tags to the recognition probes to better assist with hybridization.

Figure 18:
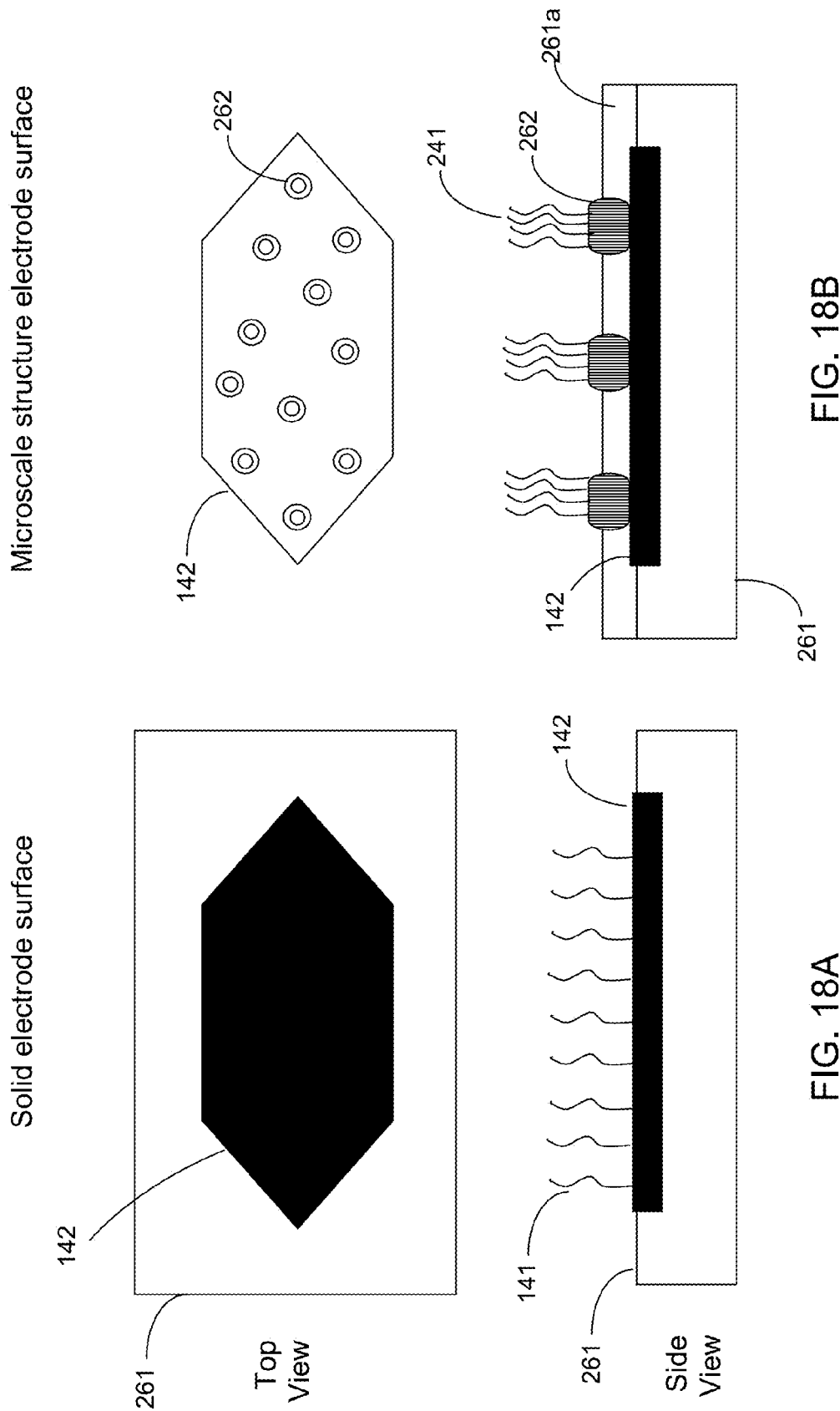
FIG. 18A is a schematic representations of an electrochemical biosensor with a solid electrode surface.
FIG. 18B is a schematic representations of an electrochemical biosensor with a low density of microscale structures.

Another unique aspect of this invention is the ability to support different types of biosensors, including a conventional solid electrode, and variations of an ultrasensitive nanobiosensor. Referring to FIG. 18A, in one embodiment, the working electrode 142 is a solid conductive structure fabricated into a non-conductive or semi-conductive base 261 as is commonly used in a low-cost disposable glucose test strip. In this embodiment the surface area can be approximately $10^{-2}$ cm$^2$. Recognition probes 141 are bound to the working electrode surface to facilitate hybridization with electrochemically detectable tags. The benefit of this biosensor is its low cost and may have adequate sensitivity should the amplification method provide a sufficient amplified level of detectable tags.

As known to those skilled in the art, a smaller working electrode surface area provides a greatly improved signal-to-noise resolution for measuring low level oxidation signals. The improved signal-to-noise resolution provides an improved limit of detection for the biosensor.

One approach for reducing the active surface area of a biosensor working electrode is to replace the active solid working electrode with nanoscale structures on the electrode surface. However, fabrication of nanoscale structures such as 100 nm diameter carbon nanotubes, provides additional complexity over microscale structures which result in the need for specialized production equipment with high cost and limited throughput, poor production yields, and high unit costs for nanobiosensors.

Another unique aspect of this invention is reducing the active surface area of a biosensor working electrode with a very low density of microstructures. This avoids nanopatterning with specialized production equipment. The thicker structures also have a higher yield, and are easier to attach recognition probes with the greater number of walls per nanotube, to provide a lower unit cost than nanobiosensors with nanoscale structures.

The benefit of this variation of a nanobiosensor is a greater sensitivity than the solid working electrode in FIG. 18A. The nanobiosensor variation can be employed when an improved detection level is desirable, at a slightly higher cost per sensor.

Referring to FIG. 18B, in another embodiment, the working electrode 142 is a variation of an ultrasensitive nanobiosensor. The microscale structure electrode surface comprises a low density plurality of electrically conductive microscale structures 262 fabricated on an electrode surface 142. Each microscale structure is encapsulated on its side walls with a non-conductive material 261a. The volume between each microscale structure is filled with said non-conductive material, leaving the tips of the microscale structure as the only exposed portions of the working electrode. This reduces the active surface area of the working electrode to the area of the exposed tips of said microscale structures, which is much smaller than the underlying working electrode. The improved signal-to-noise resolution provides an improved detection limit for the biosensor.

In one embodiment the microscale structures are cylindrical multi-walled tubes, but clearly many different shapes can also be used. An important criteria is the total surface area of all the exposed tips, which is dependent on the diameter of the microscale structures and the number of microscale structures fabricated on the working electrode. For example, if wider microscale structures are used, then the number of said microscale structures need to be reduced to ensure that the total surface area remains sufficiently low to provide the necessary signal-to-noise resolution for the desired detection limit. Unlike nanoscale structures, the microscale structures can more easily be fabricated by using conventional semiconductor fabrication tools to provide greater throughput, higher yields and lower costs.

Another advantage is that microscale structures such as multi-walled tubes have greater surface areas available for attaching recognition probes. In one example, the active surface area of the working electrode microscale structures is $10^{-7}$ cm$^2$ and is comprised of multi-walled tubes with diameters of 0.5 µm, and spaced 1.5 µm apart. In some embodiments the microscale structures are 0.25 µm to 2.5 µm in diameter. In some embodiments the microscale structures are placed 1-5 µm apart. When cylindrical nanoscale structures are used in biosensors, it is known to those skilled in the art that there is a hemispherical diffusion layer around each nanoscale structure from close proximity of neighboring nanoscale structures. This diffusion creates noise that interferes with the extremely low detection signals. The sensitivity of electrochemical biosensor working electrodes can be greatly improved when the diffusion layers of neighboring electrode structures are not overlapping so that each structure behaves independently with minimal diffusion or noise from other electrode structures. Other embodiments can include microscale or nanoscale structures created from rough surfaces, highly porous surfaces, or honeycomb crystal lattices such as graphene.

Because of the relatively high potentials required for guanine oxidation, the choice of structural materials is limited to highly conductive materials that will not oxidize themselves, such as carbonaceous materials and indium tin oxide. One embodiment provides multi-walled carbon nanotubes or nanofibers with diameters of around 0.5 µm comprising multiple walls for attaching recognition probes.

Detection Device

Figure 19:
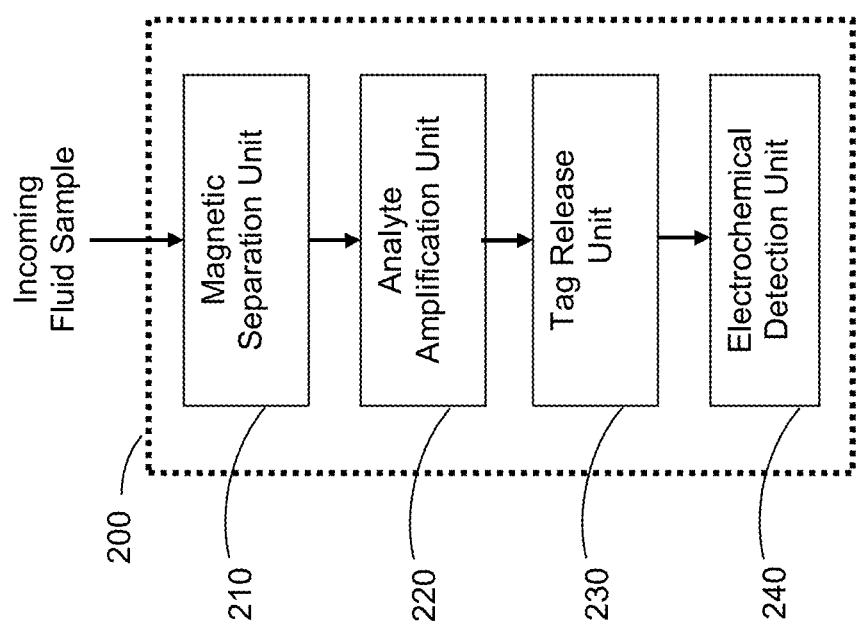
FIG. 19 is a schematic representation of the main units of an analyte detection device according to an embodiment of the present invention.

With reference to FIG. 19, the main units are shown of a device 200 for detecting and/or quantifying the level of one or more target analytes in a fluid sample.

The device first includes a magnetic separation unit 210 comprising one or more sets of magnetic particles, wherein each set comprises a plurality of magnetic particles conjugated with a plurality of an analyte binding material to create analyte-magnetic particle complexes if an associated analyte is present. The magnetic separation unit also comprises a magnet for magnetically extracting said complexes. An incoming fluid sample that may contain non-specific materials and one or more analytes is separated into a target analyte condensate containing said complexes and a non-specific waste solution containing non-specific materials that could interfere with detection or cause false detection outcomes.

The device next includes an analyte amplification unit 220 comprising one or more sets of nonmagnetic particles, wherein each set comprises a plurality of nonmagnetic particles conjugated with a plurality of an analyte binding material and also conjugated with a plurality of electrochemically detectable tags in greater amounts than the bound associated analyte to create electrochemically detectable tag-nonmagnetic particle-analyte-magnetic particle sandwiches if an associated analyte is present. The analyte amplification unit also comprises a magnet for magnetically extracting said sandwiches. An incoming target analyte condensate containing said analytes is separated into a tagged analyte condensate containing the formed sandwiches with an amplified number of electrochemically detectable tags per analyte and a waste solution containing unbound tags that do not link to associated target analytes because they are absent from the fluid sample or already bound to other sandwiches.

The device also includes a tag release unit 230 comprising a system for unbinding the electrochemically detectable tags from the tag-nonmagnetic particle-target analyte-magnetic particle sandwiches, and a magnet for immobilizing the remaining constituents of the sandwiches while the unbound tags are washed and flushed away. An incoming tagged analyte condensate containing an amplified number of electrochemically detectable tags is separated into an amplified tag condensate containing the released tags and a waste solution containing debris from nonmagnetic particles and associated sandwiches.

The device further includes an electrochemical detection unit 240 comprising an electrochemical biosensor with one or more working electrodes, wherein each working electrode is conjugated with a plurality of a recognition probe to bind with associated electrochemically detectable tags, and an electrochemical detection system that produces electrochemical signals on each working electrode in proportion to the level of an associated analyte if said analyte is present in the fluid sample.

The magnetic separation unit 210, analyte amplification unit 220, and tag release unit 230 referred to in FIG. 19 are further described above in the amplification device section and related figures. When these units are used in detection device 200, the detectable tags are limited to electrochemically detectable tags.

Electrochemical Detection Unit

With reference to FIG. 7, there is shown an electrochemical detection unit 240 according to an embodiment of the invention. The incoming amplified tag condensate fills an enclosed mixing chamber 242 containing one or more working electrodes 142. In an example of one embodiment there are 3 working electrodes 142a, 142b, 142c corresponding with three target analytes: analyte A 101a, analyte B 101b, and analyte C 101c.

The electrochemical detection unit further provides one or more sets of recognition probes attached to the surface of one or more working electrodes. In the above embodiment, each of the three working electrodes contains a set of recognition probes 141a, 141b 141c bound to the working electrode surfaces 142a, 142b 142c. Each set of recognition probes can hybridize with its complementary electrochemically detectable tags 127a, 127b, 127c, should said tags be present in the incoming amplified tag condensate. Complementary tags and probes form tag-probe duplexes 156 that become immobilized near the surface of the working electrodes.

The electrochemical detection unit further provides at least one counter electrode 243 and one reference electrode 244 which are used to facilitate electrochemical detection as is known to those skilled in the art. The electrochemical detection unit also provides electronic circuitry 245 that electrically connect each electrode to corresponding connection pads 246. Referring to FIG. 17, an embodiment can contain the working electrodes, counter electrode, reference electrode, electronic circuitry and connector pads as an independent biosensor. In one embodiment there can be one or multiple biosensors contained in an electrochemical detection unit.

Referring to FIG. 7, the connector pads 246 can physically and electrically connect to corresponding connection pads 247. The connection pads 247 are needed to electrically attach the electrochemical detection unit and/or biosensor to a potentiostat 248 or other instrument that can generate an electrical source such as potential to the electrochemical detection unit and measure the resulting electrical signal, such as current that is provided if guanine or other redox materials oxidize. The potentiostat is connected to other apparatuses 249 that may be needed to support the electrochemical detection unit as will be described below. Other electrochemical techniques and configurations can be supported as would be obvious to those skilled in the art.

The electrochemical detection unit may also provide a reservoir 252 containing an electron transport mediator such as ruthenium bipyridine, should an electron transport mediator 253 be used by the detection method.

Another unique aspect of this invention is the ability to support different types of biosensors. Referring to FIG. 18A, in one embodiment, the working electrode 142 is a solid conductive structure fabricated into a non-conductive or semi-conductive base 261 as is commonly used in a low-cost disposable glucose test strip. In this embodiment the surface area can be approximately $10^{-2}$ cm$^2$. Recognition probes 141 are bound to the working electrode surface to facilitate hybridization with electrochemically detectable tags. The benefit of this biosensor is its low cost and may have adequate sensitivity should the amplification method provide a sufficient amplified level of detectable tags.

Referring to FIG. 18B, in another embodiment, the working electrode 142 is a microscale structure electrode surface comprising a low density plurality of electrically conductive microscale structures 262 fabricated on an electrode surface 142. Each microscale structure is encapsulated on its side walls with a non-conductive material 261a. The volume between each microscale structure is filled with said non-conductive material, leaving the tips of the microscale structure as the only exposed portions of the working electrode. This reduces the active surface area of the working electrode to the area of the exposed tips of said microscale structures, which is much smaller than the underlying working electrode. The improved signal-to-noise resolution provides an improved detection limit for the biosensor. The benefit of this biosensor is a greater sensitivity than the solid working electrode in FIG. 18A and can be employed when an improved detection level is desirable, at a slightly higher cost per sensor. Other types of biosensors can also be supported.

Other Configurations

The above invention can also take the form of other configurations that provide beneficial aspects for particular applications. In some embodiments some or all of the reagents and beads can stored in a central location of the analyzer and added to the cartridge or panel as required.

Point of Care/Point of Use Device

Figure 20:
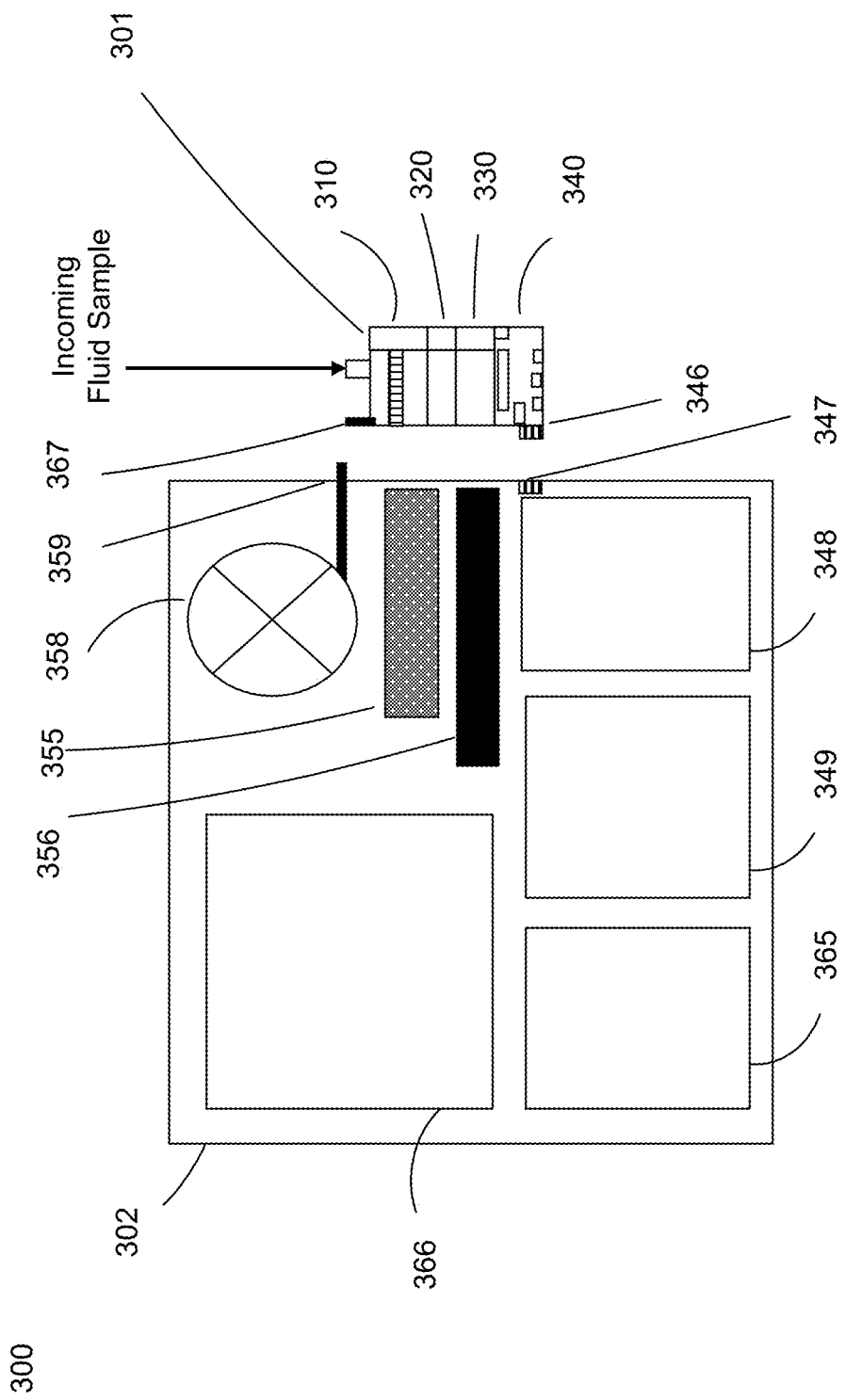
FIG. 20 is a schematic representation of a point of care/point of use analyte analyzer and consumable test cartridge according to one embodiment of the invention.

With reference to FIG. 20, the main units are shown of a point of care/point of use device 300 for detecting and/or quantifying the level of one or more target analytes in a fluid sample according to an embodiment of the invention.

The device first includes a consumable test cartridge 301 that consolidates all of the non-reusable portions of the abovementioned device 200 which are required to process a fluid sample. Said cartridge comprises a magnetic separation compartment 310, an analyte amplification compartment 320, a tag discharge compartment 330, and an electrochemical detection compartment 340. The magnetic separation compartment comprises one or more sets of magnetic particles, wherein each set comprises a plurality of magnetic particles conjugated with a plurality of an analyte binding material to create analyte-magnetic particle complexes if an associated analyte is present. The analyte amplification compartment comprises one or more sets of nonmagnetic particles, wherein each set comprises a plurality of nonmagnetic particles conjugated with a plurality of an analyte binding material and also conjugated with a plurality of detectable tags in greater amounts than the bound associated analyte to create detectable tag-nonmagnetic particle-analyte-magnetic particle sandwiches if an associated analyte is present. The electrochemical detection compartment comprises one or more working electrodes, wherein each working electrode is conjugated with a plurality of a recognition probe to bind with associated electrochemically detectable tags, and an electrochemical detection system that produces electrochemical signals on each working electrode in proportion to the level of an associated analyte if said analyte is present in the fluid sample. Optional pre-treatment processes such as a membrane can also be included in the cartridge.

The device next includes an analyzer 302 that consolidates all reusable portions of the abovementioned device 200 which are required to operate a consumable test cartridge 301 for processing a test sample. Said analyzer provides a mechanical system 358 with a mechanical connector 359 that connects to the cartridge connector 367, a magnet 355, and a tag release system 356 which may include a heater. The analyzer further provides an electrochemical signal generation and signal measurement system 348 with electrical connection 347 to the cartridge connector 346. The analyzer further provides other systems to support the operations, which may include a central processing unit 349, a power supply 365, and a user interface 366.

Low Volume Device

Figure 21:
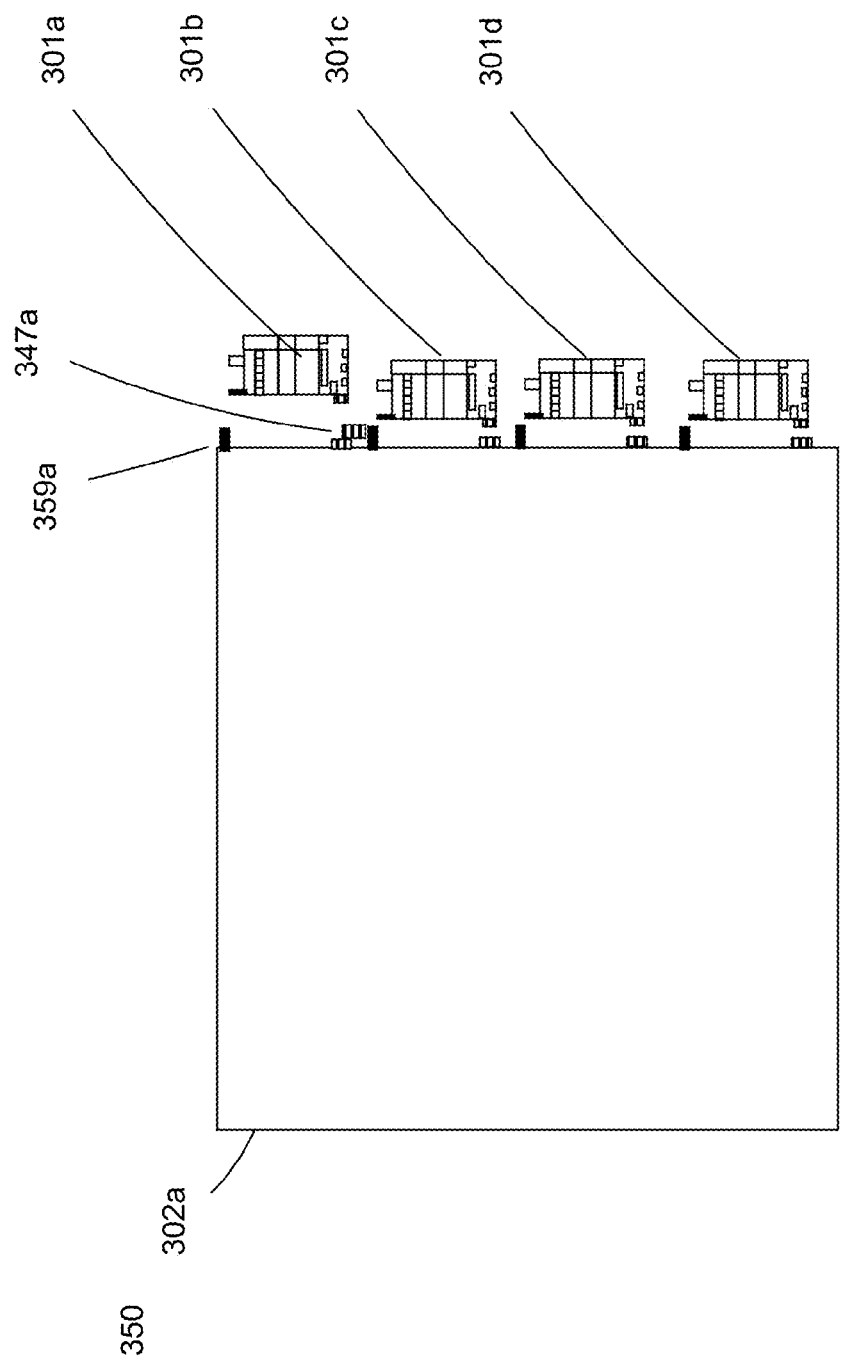
FIG. 21 is a is a schematic representation of a low volume analyte analyzer that can process one or more consumable test cartridges according to one embodiment of the invention.

With reference to FIG. 21, the main units are shown of a low volume device 350 for detecting and/or quantifying the level of one or more target analytes in one or more fluid samples according to an embodiment of the invention.

The device first includes one or more consumable test cartridges 301a, 301b, 301c, 301d, . . . that consolidate all non-reusable portions of the abovementioned device 200 which are required to process a fluid sample. Each cartridge comprises a magnetic separation compartment, an analyte amplification compartment, a tag discharge compartment, and an electrochemical detection compartment. The magnetic separation compartment comprises one or more sets of magnetic particles, wherein each set comprises a plurality of magnetic particles conjugated with a plurality of an analyte binding material to create analyte-magnetic particle complexes if an associated analyte is present. The analyte amplification compartment comprises one or more sets of nonmagnetic particles, wherein each set comprises a plurality of nonmagnetic particles conjugated with a plurality of an analyte binding material and also conjugated with a plurality of detectable tags in greater amounts than the bound associated analyte to create detectable tag-nonmagnetic particle-analyte-magnetic particle sandwiches if an associated analyte is present. The electrochemical detection compartment comprises one or more working electrodes, wherein each working electrode is conjugated with a plurality of a recognition probe to bind with associated electrochemically detectable tags, and an electrochemical detection system that produces electrochemical signals on each working electrode in proportion to the level of an associated analyte if said analyte is present in the fluid sample. Optional pre-treatment processes such as a membrane can also be included in the cartridge.

The device next includes an analyzer 302a that consolidates all reusable portions of the abovementioned device 200 which are required to simultaneously operate one or more consumable test cartridges 301a, 301b, 301c, 301d, . . . for processing one or more test samples. Said analyzer provides one or more mechanical systems with mechanical connectors 359a, . . . that connect to the cartridge connectors, magnet, and tag release system which may include a heater. The analyzer further provides one or more electrochemical signal generation and signal measurement system with electrical connections 347a, . . . to the cartridge connectors. The analyzer further provides other systems to support the operations, which may include a central processing unit, power supply, and user interface.

High Throughput Device

Figure 22:
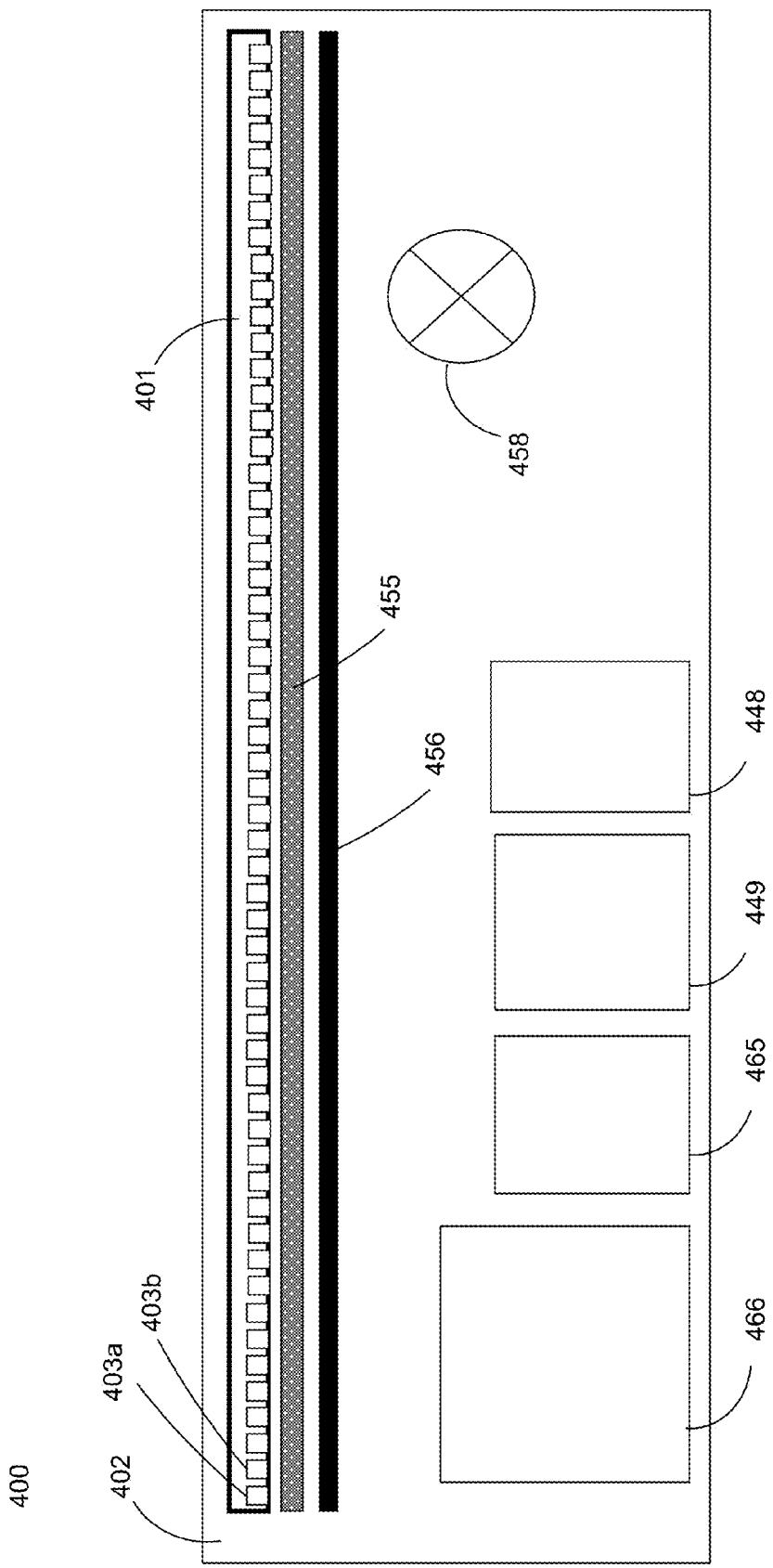
FIG. 22 is a schematic representation of a high throughput analyte analyzer and high throughput test panel according to one embodiment of the invention.

With reference to FIG. 22, the main units are shown of a high throughput device 400 for detecting and/or quantifying the level of one or more target analytes in a plurality of fluid samples according to an embodiment of the invention.

The device first includes a high throughput test panel 401 comprising a plurality of wells 403a, 403b, . . . that consolidate all non-reusable portions of the abovementioned device 200 which are required to process a fluid sample. Each well comprises a magnetic separation compartment, an analyte amplification compartment, a tag discharge compartment, and an electrochemical detection compartment. The magnetic separation compartment comprises one or more sets of magnetic particles, wherein each set comprises a plurality of magnetic particles conjugated with a plurality of an analyte binding material to create analyte-magnetic particle complexes if an associated analyte is present. The analyte amplification compartment comprises one or more sets of nonmagnetic particles, wherein each set comprises a plurality of nonmagnetic particles conjugated with a plurality of an analyte binding material and also conjugated with a plurality of detectable tags in greater amounts than the bound associated analyte to create detectable tag-nonmagnetic particle-analyte-magnetic particle sandwiches if an associated analyte is present. The electrochemical detection compartment comprises one or more working electrodes, wherein each working electrode is conjugated with a plurality of a recognition probe to bind with associated electrochemically detectable tags, and an electrochemical detection system that produces electrochemical signals on each working electrode in proportion to the level of an associated analyte if said analyte is present in the fluid sample. Optional pre-treatment processes such as a membrane can also be included in the wells.

The device next includes a high throughput analyzer 402 that consolidates all reusable portions of the abovementioned device 200 which are required to operate a high throughput test panel 401 comprising a plurality of wells 403a, 403b, . . . for processing test samples. Said analyzer provides one or more mechanical systems 458 that connect to the wells, a magnet 455, and tag release system which may include one or more heater 456. The analyzer further provides one or more electrochemical signal generation and signal measurement system 448 with electrical connections to the wells. The analyzer further provides other systems to support the operations, which may include one or more central processing unit 449, power supply 465, and user interface 466.

Autonomous Networked Device

Figure 23:
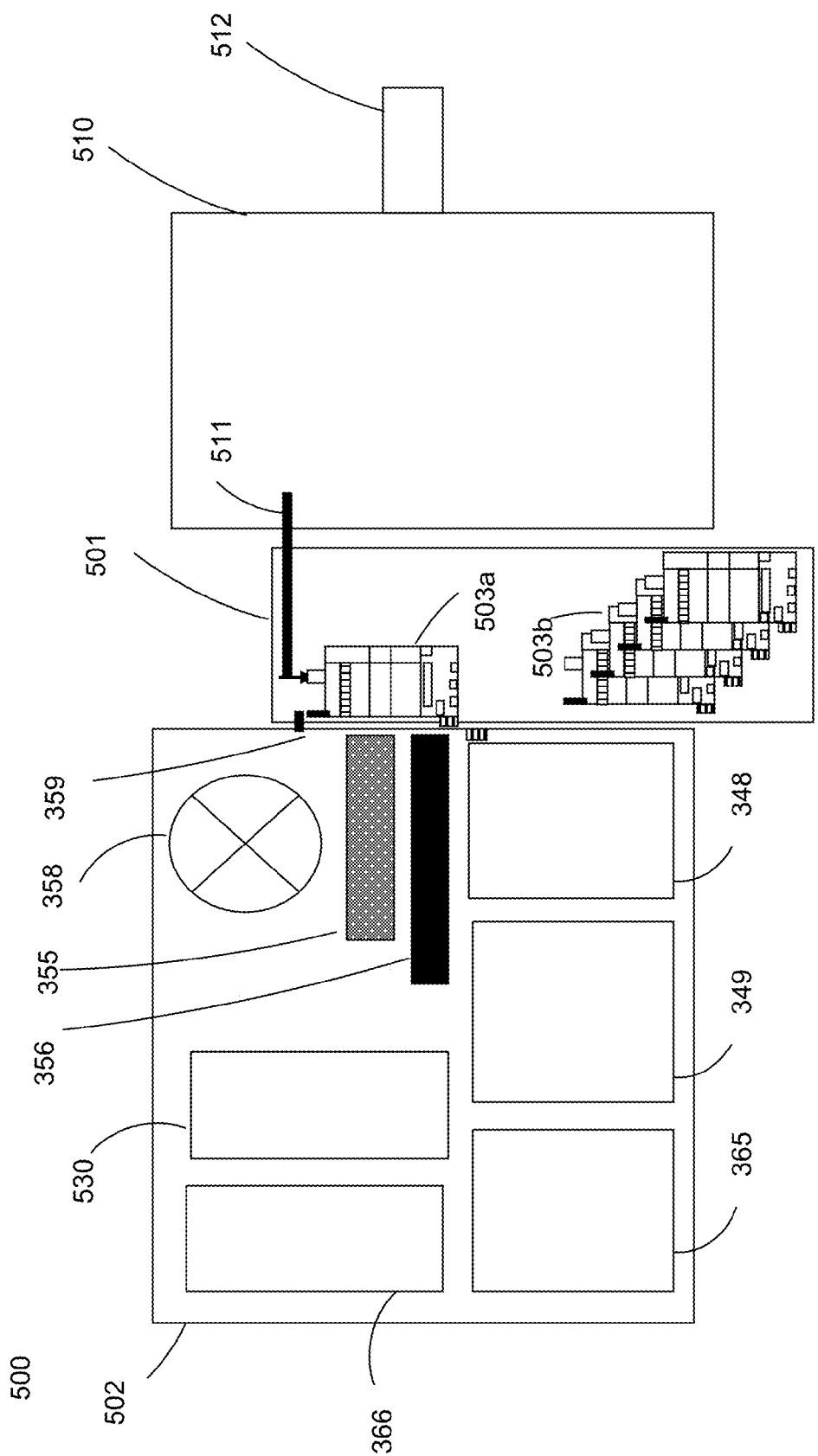
FIG. 23 is a schematic representation of an autonomous networked analyzer, consumable test cartridges, and sample collection and concentration unit according to one embodiment of the invention.

With reference to FIG. 23, the main units are shown of an autonomous networked device 500 capable of integrating with an automated sampling and concentration instrument to remotely analyze field samples without a technician in an autonomous networked application for detecting and/or quantifying the level of one or more target analytes in a fluid sample according to an embodiment of the invention.

The device first includes a test cartridge assembly 501 that includes one or more test cartridges 503a, 503b, . . . that consolidate all non-reusable portions of the abovementioned device 200 which are required to process a fluid sample. Each cartridge comprises a magnetic separation compartment, an analyte amplification compartment, a tag discharge compartment, and an electrochemical detection compartment. The magnetic separation compartment comprises one or more sets of magnetic particles, wherein each set comprises a plurality of magnetic particles conjugated with a plurality of an analyte binding material to create analyte-magnetic particle complexes if an associated analyte is present. The analyte amplification compartment comprises one or more sets of nonmagnetic particles, wherein each set comprises a plurality of nonmagnetic particles conjugated with a plurality of an analyte binding material and also conjugated with a plurality of detectable tags in greater amounts than the bound associated analyte to create detectable tag-nonmagnetic particle-analyte-magnetic particle sandwiches if an associated analyte is present. The electrochemical detection compartment comprises one or more working electrodes, wherein each working electrode is conjugated with a plurality of a recognition probe to bind with associated electrochemically detectable tags, and an electrochemical detection system that produces electrochemical signals on each working electrode in proportion to the level of an associated analyte if said analyte is present in the fluid sample. Optional pre-treatment processes such as a membrane can also be included in the cartridge.

The device next includes an analyzer 502 that consolidates all reusable portions of the abovementioned device 200 which are required to operate a consumable test cartridge 501 for processing a test sample. Said analyzer provides a mechanical system 358 with a mechanical connector 359 that connects to the cartridge connector, a magnet 355, and a tag release system 356 which may include a heater. The analyzer further provides an electrochemical signal generation and signal measurement system 348 with electrical connection to the cartridge connector. The analyzer further provides other systems to support the operations, which may include a central processing unit 349, a power supply 365, and a user interface 366.

An optional communications capability 530 may be included in the analyzer 502 or as a separate unit to communicate test results and other information through wireless or wired communications.

The device next includes a sample collection and concentration unit 510 that automatically samples and/or concentrates air, water, or other media through an input mechanism 512. Said sample collection and concentration unit delivers a processed and/or concentrated sample to the inlet 511 of an unused test cartridge 503.

Developer Kit

Figures 24A, 24B:
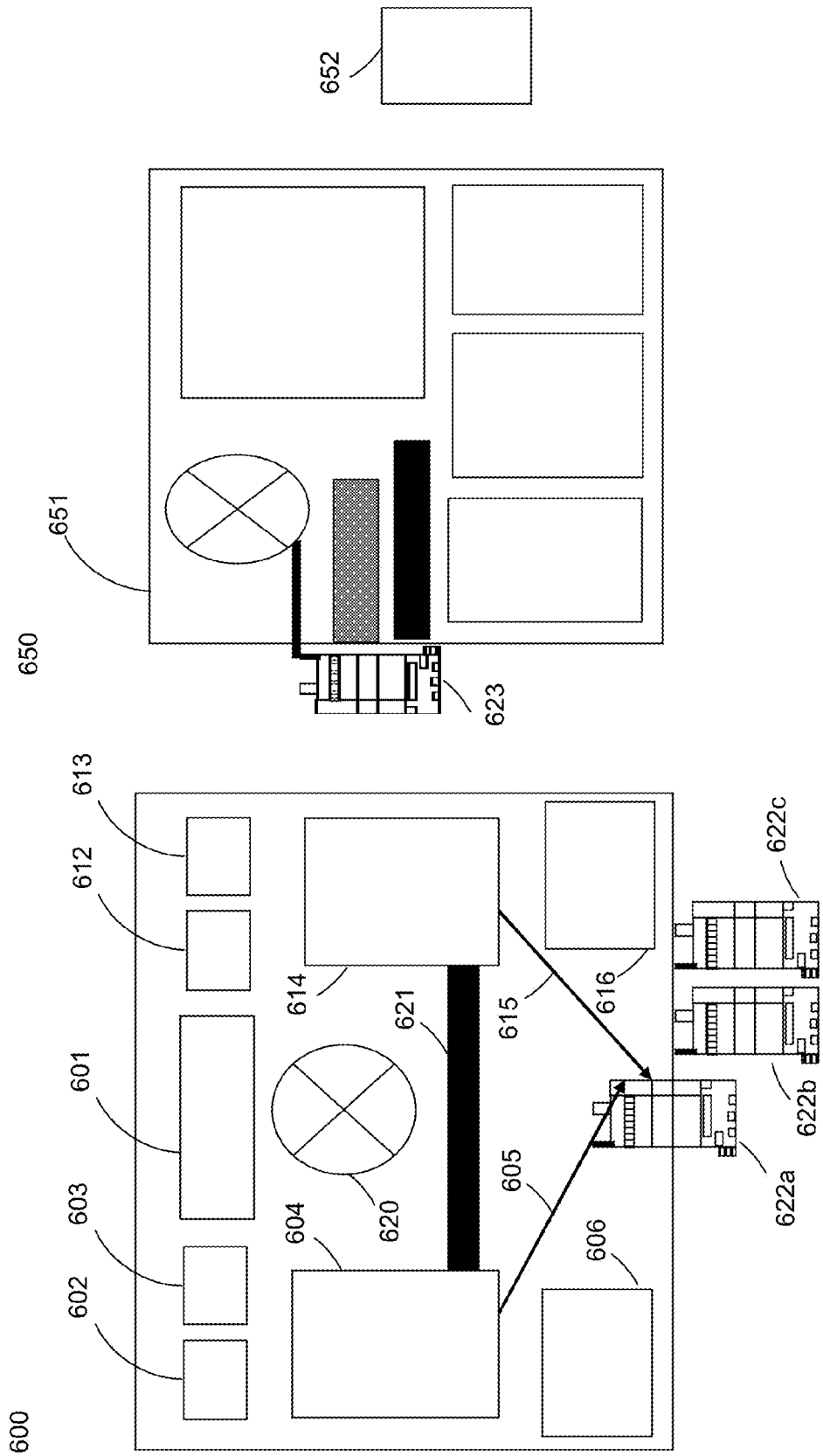
FIGS. 24A and 24B are a schematic representation of a developer kit according to one embodiment of the invention comprising a cartridge preparation instrument in FIG. 24A and a cartridge validation instrument in FIG. 24B.

With reference to FIGS. 24A and 24B, the main units are shown of a developer kit for developing test cartridges and test panels for applications of the invention. The kit can be used for validating different antibodies, DNA probes, amplification ratios and process protocols. The kit can also be used for producing low volume batches of test cartridges and test panels.

The kit first includes a cartridge preparation instrument 600 that automates one or more standard protocols for conjugating antibodies and DNA probes to particles such as the protocol used in the Pierce Direct Magnetic IP and Co-IP Kit (Thermo Fisher Scientific, Pierce Antibodies, Rockford, Ill.). The instrument comprises a reagent storage compartment 601, a magnetic particle storage compartment 602, an antibody or DNA probe storage compartment 603, and a preparation chamber 604. The antibodies or DNA probes to be validated are provided by the developer. Said instrument provides a mechanical system 620 and a heater 621. The instrument further provides other systems to support the various operations, which may include a central processing unit, power supply, and user interface. Once the conjugation protocol is completed, the conjugated magnetic particles are transferred out 605 of the preparation chamber 604 and inserted into a portion of a developer kit test cartridge 622a. Said developer kit test cartridge is similar to test cartridge 301 but does not include conjugated magnetic particles or conjugated nonmagnetic particles.

The instrument further comprises a nonmagnetic particle storage compartment 612, an antibody or DNA probe storage compartment 613, and a preparation chamber 614. The antibodies or DNA probes to be validated are provided by the developer. Nonmagnetic particles with oligonucleotide guanine tags are selected by the developer based on the amplification ratio of guanine molecules per target to be tested. Once the conjugation protocol is completed, the conjugated nonmagnetic particles are transferred out 615 of the preparation chamber 614 and inserted into a portion of a developer kit test cartridge 622a. After the conjugated magnetic particles and conjugated nonmagnetic particles are inserted, the developer kit test cartridge 622a would be sealed, have a identification code printed on its surface and be ready for validation testing as a developer kit validation cartridge 623.

In applications which require multiplexing, there would be sets of magnetic particles and nonmagnetic particles required for each target analyte. The instrument further comprises a conjugated magnetic particle storage compartment 606 and a conjugated nonmagnetic particle storage compartment 616 to temporarily store conjugated magnetic particles and conjugated nonmagnetic particles while other sets are being separately conjugated. Once all of the sets are conjugated they could be inserted into the appropriate portion of a developer kit test cartridge 622a.

As would be understood by those skilled in the art, the cartridge preparation instrument 600 can be configured to produce a plurality of developer kit test cartridges 622a, 622b, 622c, . . . in the same batch. The instrument 600 can further be configured to prepare and transfer conjugated magnetic particles and conjugated nonmagnetic particles to a high throughput test panel 401.

The developer kit 600 next includes a cartridge validation instrument 651 that consolidates all reusable portions of the abovementioned device 200 which are required to operate one or more consumable test cartridge 301, or developer kit validation cartridge 623 for processing a test sample. Said instrument provides one or more mechanical systems with mechanical connectors that connect to the cartridge connectors, magnet, and tag release system which may include a heater. The instrument further provides one or more electrochemical signal generation and signal measurement system with electrical connections to the cartridge connectors. The instrument further provides other systems to support the operations, which may include a central processing unit, power supply, and user interface. The instrument further provides software 652 that allows a developer to select and configure the process protocols to be used to process the sample, that analyzes test data and generates statistical test results for the developer, and that produces standard curves.

EXAMPLES

In order that this invention may be better understood, the following examples are set forth. These examples are provided solely for the purpose of further illustrating certain specific aspects and embodiments of the invention. Although embodiments of the invention have been disclosed for illustrative purposes, those skilled in the art will appreciate that various modifications, additions and substitutions are possible, without departing from the scope and spirit of the invention as herein described, and all are included within the scope of the invention.

Example 1

Determination of New Assay Requirements: An assay was required to measure approximately $5\times10^{-21}$ M *E. coli* O157:H7 analytes in a 1 mL liquid solution with at least 2 orders of magnitude linear dynamic range. The number of analytes to be detected from 1 mL was calculated to be $5\times10^{-24}$ mols, or approximately 3 molecules by multiplying the number of mols by Avogadro constant of $6.02\times10^{23}$/mol. A graphene oxide—glassy carbon working electrode was selected with 1 mm² surface area which is capable of measuring at least approximately $1\times10^8$ guanine molecules. The required amplification ratio was estimated to be at least $5\times10^7$ guanines per analyte based on the sensor detection capability of $1\times10^8$ guanine molecules divided by 3 target molecules divided by about 60% recovery from the antibody matched pairs. According to Table 10, approximately $1\times10^8$ guanines could be delivered per bead using 15 micron diameter polystyrene beads with a capacity of $7\times10^6$ oligonucleotides per bead and 20 guanines per oligonucleotides. The associated working electrode would need to have at least $7\times10^6$ cytosine oligonucleotides to hybridize with the guanine oligonucleotide tags. For a 2 order of magnitude linear dynamic range there needs to be at least 100 times the number of duplexes hybridized, requiring at least approximately $7\times10^8$ cytosine oligonucleotides per working electrode.

TABLE 10

Maximum Loading Capacity of Guanines Per Bead With Different Polystyrene Bead Diameters and Guanine Bases Per Oligonucleotide

| Polystyrene Bead Options | | Guanines per Oligonucleotide and Guanines per Bead based on Bead Diameter | | | |
|---|---|---|---|---|---|
| Bead Diameter | Oligos per Bead | 5 | 20 | 100 | 250 |
| 1 micron | $3 \times 10^4$ | $2 \times 10^6$ | $6 \times 10^5$ | $3 \times 10^6$ | $8 \times 10^6$ |
| 15 micron | $7 \times 10^6$ | $4 \times 10^7$ | $1 \times 10^8$ | $7 \times 10^8$ | $2 \times 10^9$ |
| 35 micron | $4 \times 10^7$ | $2 \times 10^8$ | $8 \times 10^8$ | $4 \times 10^9$ | $1 \times 10^{19}$ |
| 100 micron | $3 \times 10^8$ | $2 \times 10^9$ | $6 \times 10^9$ | $3 \times 10^{19}$ | $8 \times 10^{19}$ |

Example 2

Calculation of Inputs: Commercially available polystyrene beads were identified from multiple suppliers in 15.28 micron diameter size. The oligonucleotide loading capacity was determined to be about $7.3 \times 10^6$ guanine rich oligonucleotides per bead. Approximately $7.5 \times 10^{13}$ guanine rich oligonucleotides were available from a 2.5 μL volume of 5 μM oligonucleotide concentration and mixed with 100,000 beads from a 20 μL volume and 10 g/μL concentration. This provided approximately $7.5 \times 10^8$ guanine rich oligonucleotides per bead with sufficient oligonucleotides to saturate the 15.28 micron bead surface with oligonucleotides.

TABLE 11

Computation of Inputs for Required Amplification Ratio

| Parameter | Inputs | | Assay Requirements |
|---|---|---|---|
| Maximum Guanine Oligos per Bead | | | |
| Nonmagnetic Beads | Diameter | 15.28 microns | $7.3 \times 10^6$ guanine rich oligos/bead |
| Guanine Oligo Solution | | | |
| Guanine rich oligonucleotides | Volume Concentration | 2.5 μL 5 μM | $7.5 \times 10^{13}$ guanine rich oligos |
| Nonmagnetic beads | Volume Concentration | 20 μL 10 g/μL | $1.0 \times 10^5$ nonmagnetic beads |
| Guanine oligos available per bead | Guanine oligos Number of nonmagnetic Beads | $7.5 \times 10^{13}$ Guanine rich oligos $1.0 \times 10^5$ nonmagnetic beads | $7.5 \times 10^8$ guanine rich oligos/bead |
| Amplification Ratio | | | |
| Amplification Ratio | Maximum guanine oligos per bead Number of guanines per oligo | $7.3 \times 10^6$ guanine rich oligos/bead 20 | $1.5 \times 10^8$ guanines/bead |

Example 3

Preparation of Nonmagnetic Particles with Guanine Tags: Approximately 20 μL of nominally 15.28 micron diameter commercial polystyrene microspheres precoated with avidin (Bangs Laboratories, Inc., Fishers, Ind.) were pipette into a 1.5 mL Eppendorph tube with 2.5 μL deionized water and 2.5 μL of 5 μM oligonucleotide tags containing 20 guanines of 30 bases GTG GGT GGG TAA GGA GTG AGG GTG GGA GTT. The solution was incubated for 20 minutes at room temperature with pipette mixing then centrifuged. The supernatant was removed and the solution was washed with 500 μL deionized water followed by repeated centrifuge, supernatant removal and washing. Then 25 μL of 1 mg/mL Anti-*Escherichia coli* O157:H7 Antibody, Biotin-labeled (KPL Inc., Gaithersburg, Md.) was added, pipette mixed and incubated for 15 minutes at room temperature. The particles were washed with Imidazole Buffered Saline and Tween (KPL Inc., Gaithersburg, Md.) diluted 20:1 by adding 500 μL, centrifuge, and removing supernatant. Following repeated washing, centrifuge and supernatant removal, the particles were re-suspended in 20 μL deionized water.

Example 4

Preparation of Working Electrode. Graphene oxide (GO) was deposited on a glassy carbon electrode (GCE) by electrodeposition and dip-coating. A graphite/graphene oxide powder (Graphene Supermarket, Calverton, N.Y.) was exfoliated in 0.1 M pH 9.18 phosphate buffer solution by ultrasonication for 30 minutes to form a homogeneous brown GO colloidal dispersion with 0.5 mg/mL concentration. Cyclic voltammetric reduction was performed in the GO dispersion with magnetic stirring using a three-electrode system with the GCE working electrode, a Pt mesh counter electrode, and Ag/AgCl reference electrode using a Gamry 600 potentiostat. Potential was scanned from 1.5 to 1 V at a rate of 50 mV/s with 2 mV step size for 18-30 cycles. After deposition, the working electrode was washed with deionized water, and then dried in vacuum at room temperature. The electrode substrate was immersed in 0.5 mg/mL graphene oxide solution for 5 hours. The electrode was then prepared for functionalization by electrochemically etching at 1.5 V vs. saturated calomel electrode for 120 seconds in 1.0 M NaOH. 10 μL of 400 mM EDC and 100 mM NHS in 0.1 M MES (2-(N-morpholino)ethanesulfonic acid) buffer (pH 5.9) was placed onto the GO-COOH/GCE for 1 hour. The electrode was washed with MES buffer and dried with nitrogen. EDC-NHS was then used to attach amine terminated oligonucleotide probes CAC CCA CCC ATT CCT CAC TCC CAC CCT CAA-3' to the activated GO-COOH/GCE surface through the amine groups at the 5' terminal. 10 μL of a 5 μM probe solution was added to the electrode in 0.1 M PBS buffer and incubated at 25° C. for 1 hour.

Example 5

Test Cycle. A 1 mL sample containing $5 \times 10^{-20}$ M *E. coli* O157:H7 nonpathogenic strain (American Type Culture Collection, Manassas, Va.) was mixed at room temperature for 10 minutes with 20 μL Dynabead MAX *E. coli* O157:H7 magnetic beads (Life Technologies, Carlsbad, Calif.). Established Dynabead kits and protocols were used to prepare and separate magnetic bead-*E. Coli* O157:H7 complexes using magnetic separation. The supernatant was removed and the magnetic bead-*E. Coli* O157:H7 complexes were resuspended in 500 mL deionized water, followed by repeated separation and resuspension, then centrifuging the final sample for one minute. 20 μL of nonmagnetic beads with guanine tags and Anti-*Escherichia coli* O157:H7 Antibody as described in Example 3 were added to the magnetic bead complex solution and incubated at room temperature for 10 minutes. The above magnetic separation protocol was repeated to produce the sandwich structures. After centrifuging, all but 25 μL of supernatant was removed. The remaining sample was incubated in a water bath at 90° C. for three minutes to elute the guanine tags. The remaining supernatant was delivered to the Probe/GO-COOH/GCE electrode described in Example 4 and was incubated with 10 μL of 0.1 M PBS buffer (pH 7.4) for 1 hour at room temperature, followed by washing with 0.1 M PBS buffer. Differential pulse voltammetry (DPV) was applied and potential was scanned from 0.5 V to 1.2 V in 0.2 M NaOAC buffer (pH 5) containing 5.0 μM Ru(bpy)$_3^{2+}$ as the electron transport mediator for electrochemical measurements. Scan parameters were 10 mV step size, 20 mV pulse size, 2 second sample period, and 0.1 second pulse time.

Example 6

Linear Dynamic Curve. The test cycle described in example 5 was repeated with different known concentrations of *E. Coli* O157:H7 nonpathogenic strain. 5.0 μM Ru(bpy)$_3^{2+}$ was used in each test cycle as a reference value for comparing scans from different sensors. At least 3 DPV scans were conducted for each E. Coli O157:H7 concentration. The first scan peak amplitude (Scan 1) was produced from the redox oxidation signal of guanine associated with the E. Coli O157:H7 concentration plus the Ru(bpy)$_3^{2+}$ electron transport mediator. The second scan peak amplitude (Scan 2) was produced from the redox oxidation signal from only the Ru(bpy)$_3^{2+}$ electron transport mediator. The guanine signal associated with the E. coli O157:H7 concentration was measured as the difference in peak signals from Scan 1 minus Scan 2. The linear concentration curve in FIG. 25 was produced by plotting the normalized guanine oxidation peak signal versus associated E. coli O157:H7 concentration. The normalized guanine oxidation peak signal for each concentration was determined by dividing the peak signal from guanine associated with E. Coli O157:H7 (Scan 1-Scan 2) by the peak signal from the Ru(bpy)$_3^{2+}$ electron transport mediator (Scan 2).

Example 7

Present/Absent Test. The test cycle described in example 5 was repeated with a test concentration of E. coli O157:H7 nonpathogenic strain. Three DPV scans were conducted. The guanine signal associated with the E. coli O157:H7 concentration was measured as the difference in peak signals from Scan 1 minus Scan 2 to be 94 nA. A third scan was performed to measure the redox oxidation signal from only the Ru(bpy)$_3^{2+}$ electron transport mediator. The threshold noise associated with variability in the Ru(bpy)$_3^{2+}$ signal in the absence of guanine associated with E. Coli O157:H7 was 7 nA. Since the E. coli O157:H7 signal was greater than the threshold value for noise, the E. coli O157:H7 analyte was determined to be present in the test sample.

Example 8

Quantification Test. The present/absent test described in Example 7 was further evaluated to obtain a quantitative value associated with the E. coli O157:H7 sample. The peak E. coli O157:H7 signal of 94 nA from Scan 1-Scan 2 and associated normalized signal of 0.77, was compared with the linear dynamic curve described in Example 6. The associated concentration from the normalized signal was determined to be about $5\times10^{-19}$ M E. coli O157:H7.

Example 9

Control Validation: The present/absent test described in Example 7 was further evaluated to ensure that the signal associated with 5.0 µM Ru(bpy)$_3^{2+}$ electron transport mediator was within a certain range of values from the pre-determined control signal. The level measured from the Scan 2 value was within 2 percent of the control value of suggesting that the test sample was indeed representative.

Example 10

Multiplex Antigen/Antibody Test for HIV. A multiplex assay was required to measure antigens and antibodies associated with HIV. Multiple analytes can be measured at the same time from the same sample using unique sets of magnetic beads, nonmagnetic beads, guanine tags, working electrodes and cytosine recognition probes associated with specific analytes. A first analyte was 0.05 pg/mL of HIV-1 p24 antigens. The corresponding molar concentration of 0.002 pM was found by dividing 0.05 pg/mL by the molecular weight of 24,000 g/mol times 1000 mL/L. The number of p24 antigens to be detected from 100 µL whole blood was calculated to be $2\times10^{-17}$ mols, or approximately $1.2\times10^5$ molecules by multiplying the number of mols by Avogadro constant of $6.02\times10^{23}$/mol. A multiplex sensor was selected with multiple graphene oxide—glassy carbon working electrodes as in Example 1. Each working electrode is capable of measuring at least approximately $1\times10^8$ guanine molecules. The required amplification ratio was estimated to be at least $1.4\times10^3$ guanines per analyte based on the sensor detection capability of $1\times10^8$ guanine molecules divided by approximately $1.2\times10^5$ target molecules divided by about 60% recovery from the antibody matched pairs. The amplification ratio would be calculated in a similar manner for each additional analyte such as HIV-1 gp 41 antibodies, and appropriate markers associated with HIV-2 and HIV-1 Group M. Commercial products are available from numerous vendors such as Thermo Fisher Pierce Antibodies (Rockford, Ill.) for procuring assay requirements including matched antibodies for HIV-1 p24 antigens, recombinant antigens for target antibodies, magnetic beads and kits for conjugating antibodies and recombinant antigens to magnetic beads. Oligonucleotide tags from Example 3 containing 20 guanines of 30 bases GTG GGT GGG TAA GGA GTG AGG GTG GGA GTT can be used for the first analyte. Different guanine oligonucleotide tags can be used for subsequent analytes that do not cross react with the first tag. Oligonucleotide sequences can be selected using commercial tools for oligonucleotide and PCR primer design. Once done, the beads and working electrodes can be prepared as described in the above examples.

Example 11

Multiplex Test for Multiple Low Level Cancer Markers. The multiplex assay in Example 10 can be modified to simultaneously detect and quantify multiple different tumor markers from a blood sample. Tumor markers are measurable biomaterials associated with a malignancy and are produced by tumor cells or the body in response to tumor cells. Although thousands of tumor markers have been identified very few are in clinical practice because most tumor markers a) are produced in extremely low levels, b) cannot be amplified with PCR or enrichment, c) are surrounded by other materials in several orders of magnitude greater amounts, d) have a normal level in healthy people and an elevated level in cancer patients which is still relatively low, e) have healthy and normal levels which can vary greatly from person to person, f) have an elevated level for a limited period of time, g) are not specific to a single cancer, h) can significantly increase in specificity to a single cancer when multiple markers are analyzed together, i) can be present as different proteins, nucleic acids and metabolites. An assay can be developed from the invention that measures multiple markers at the same time from the same sample using unique sets of magnetic beads, nonmagnetic beads, guanine tags, working electrodes and cytosine recognition probes associated with specific marker analytes. Each marker would require a base pair of analyte binding materials that would likely be custom fabricated then used in making the assay as described in Example 10. In the case of small sized markers, as is known in the industry, small analyte molecules which do not have sufficient surface volume for base pairs typically have a single analyte binding material which is bound to a larger structure, which in turn can have base pairs.

Example 12

Figure 26:
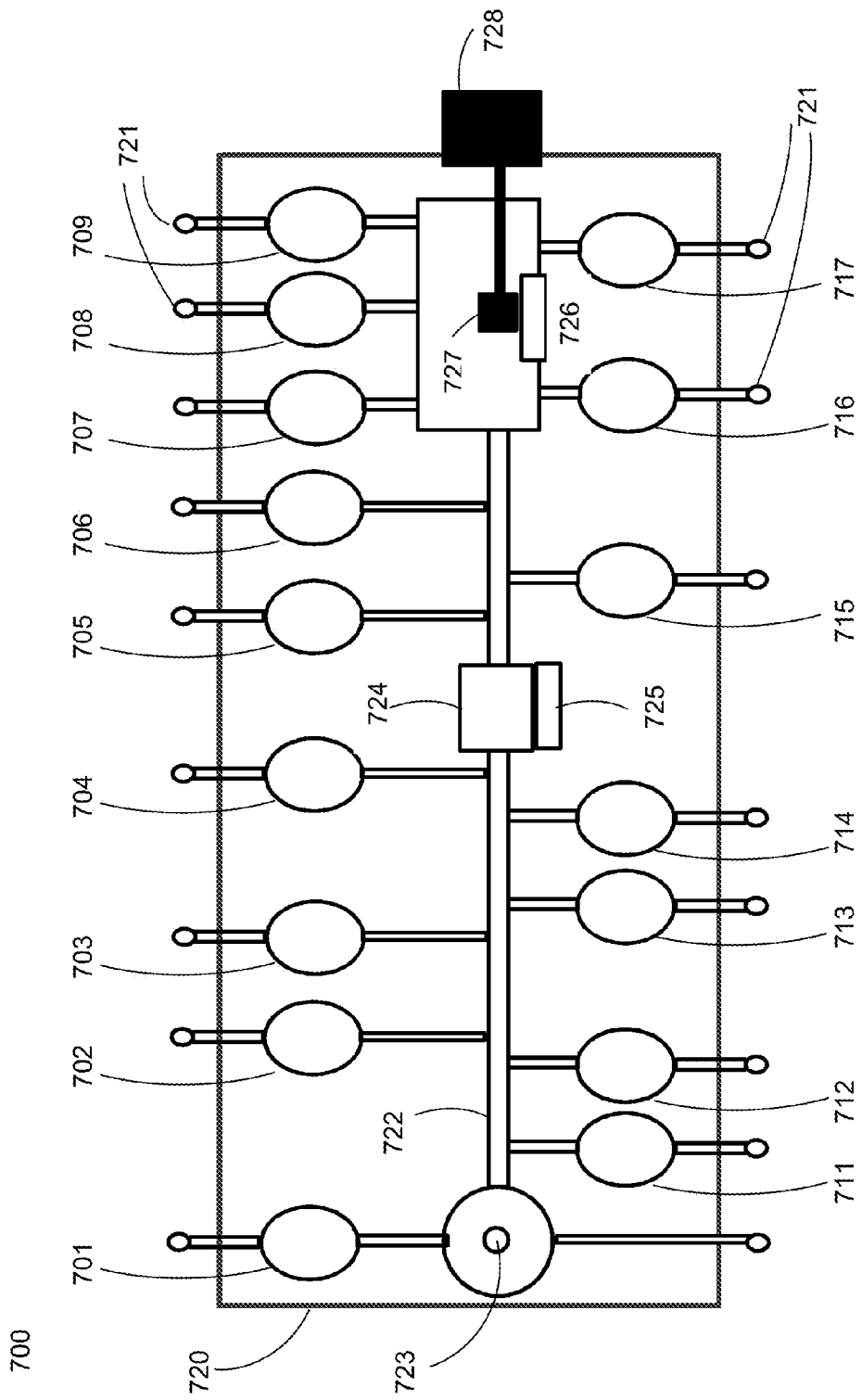
FIG. 26 is a schematic representation of a disposable test cartridge for conducting a test cycle using a point-of-care analyzer or point-of-use analyzer.

Disposable Test Cartridge. A pre-fabricated disposable test cartridge as illustrated in FIG. 26 allows a test cycle to be conducted using a point-of-care analyzer. The consumable test cartridge 700 comprises a magnetic separation compartment 724, an analyte amplification compartment which is also conducted in 724, a tag discharge compartment which is also conducted in 724, and an electrochemical detection compartment 727. The compartments are enclosed in a housing 720 which also contains an electro-magnetic in the magnetic separation compartment 724, heater 725, biosensor 727 with at least one working electrode, heater 726, a sample input chamber 723, chambers 701-717 for storing consumable test materials listed in Table 12, and microfluidics channels 722 which connect said chambers and compartments, and allow fluids to flow within the cartridge during a test cycle. The cartridge further comprises inlet values 721 which connect each chamber to an external analyzer that employs a pump and compressor for pumping and pulling fluids within the cartridge, and electrical connectors 728 which connect the electrical circuits to an external analyzer for electrically operating the biosensor, heater, and electro-magnet.

TABLE 12

Disposable Test Cartridge Solutions

| Chamber | Content | Volume |
|---|---|---|
| 701 | Magnetic Bead Solution | 200 μL |
| 702 | Suspension Buffer | 300 μL |
| 703 | Nonmagnetic Beads Solution | 200 μL |
| 704 | Eluent | 160 μL |
| 705 | Empty-for Waste from Magnetic Bead Solutions | |
| 706 | Empty-for Waste from Non-magnetic Bead Solutions | |
| 707 | Hybridization Buffer | 100 μL |
| 708 | Hybridization Wash 1 | 200 μL |
| 709 | Hybridization Wash 2 | 200 μL |
| 711 | Vent | |
| 712 | Magnetic Bead Wash 1 | 200 μL |
| 713 | Magnetic Bead Wash 2 | 200 μL |
| 714 | Nonmagnetic Bead Wash 1 | 200 μL |
| 715 | Nonmagnetic Bead Wash 2 | 200 μL |
| 716 | Empty-for Waste from Suspension Buffer Solutions | |
| 717 | Empty-for Waste from Hybridization Solutions | |
| 718 | Electron Transport Mediator | 200 μL |

In this example, a 100 μL sample is manually injected into sample input chamber 723 and vented though Chamber 711. A magnetic bead solution from Chamber 701 is pumped to the sample chamber 723 and mixed between Chambers 701 and 711. The magnetic field is turned on and solutions are mixed by pumping and pulling fluids between Chambers 711 and 705. The magnetic bead wash 1 is pumped from Chamber 712 and mixed between Chambers 712 and 705. Waste is moved to Chamber 705. The magnetic bead wash 2 is pumped from Chamber 713 and mixed between Chambers 713 and 705. Waste is moved to Chamber 705. The magnetic field is turned off, and the suspension buffer is pumped from Chamber 702 and suspends the magnetic bead complexes at the magnet 724 and then is mixed in Chamber 716. Waste is moved to Chamber 716. The nonmagnetic beads solution is pumped between Chamber 703 and 716. The magnetic field is turned on, and the solution is mixed between Chambers 716 and 703. Waste is moved to Chamber 706. The nonmagnetic bead wash 1 is pumped from Chamber 714 and mixed between Chambers 714 and 706. Waste is moved to Chamber 706. The nonmagnetic bead wash 2 is pumped from Chamber 715 and mixed between Chambers 715 and 706. Waste is moved to Chamber 705. With the magnetic field still on, eluent is pumped from Chamber 704. The solution is heated with heater 725 and drawn to Chamber 717. Guanine tags in the solution come in contact with cytosine probes at the biosensor 727. The hybridization buffer is pumped from Chamber 707, drawn to Chamber 717 and mixed with the solution at the biosensor 727 and heat is applied from heater 726. Waste is moved to Chamber 717. Hybridization wash 1 is pumped from Chamber 708 and mixed between Chambers 708 and 717. Waste is moved to Chamber 717. Hybridization wash 2 is pumped from Chamber 709 and mixed between Chambers 709 and 717. Waste is moved to Chamber 717. The electron transport mediator is pumped from Chamber 718 to biosensor 727. All systems are turned off and a DPV protocol is applied.

What is claimed is:

1. A signal amplification sandwich structure for amplifying, detecting and/or quantifying an analyte or multiple different analytes in a fluid sample, wherein said structure consists of:
   (a) a first outer layer comprising a magnetic particle conjugated with a plurality of a first analyte binding material for binding the analyte;
   (b) an inner layer comprising said analyte; and
   (c) a second outer layer comprising a nonmagnetic particle conjugated with a plurality of a second analyte binding material for binding said analyte that is a matched pair with the first analyte binding material, and the nonmagnetic particle is also conjugated on its outer structure or temporarily filled in its inner structure with a plurality of an electrochemically detectable oligonucleotide tag in greater amounts than said analyte from said inner layer,
   wherein:
   (i) said electrochemically detectable oligonucleotide tags are for signal amplification, wherein the majority of nucleotides within said oligonucleotide tags are guanine, wherein said nucleotides within said oligonucleotide tags are selected from the group consisting of guanine, adenine, and thymine, and wherein the combination of said nucleotides produces a unique oligonucleotide tag that is used to amplify, detect and/or quantify said analyte or multiple different analytes;
   (ii) analyte amplification performance of said signal amplification sandwich structure can be tuned to meet the desired limit of detection by adjusting one or more of the following parameters: (a) the number of electrochemically detectable oligonucleotide tags per nonmagnetic particle; (b) the number of guanines per electrochemically detectable oligonucleotide tag; (c) the size of the nonmagnetic particle; and (d) the surface area of the nonmagnetic particle for conjugating electrochemically detectable oligonucleotide tags;
   (iii) the number of electrochemically detectable oligonucleotide tags per nonmagnetic particle ranges from $10^2$ to $10^{13}$, the number of guanines per electrochemical detectable oligonucleotide tag ranges from 10 to 400, wherein the nonmagnetic particles are spherical and/or nonspherical, the diameter of spherical nonmagnetic particles ranges from 1 to 400 micrometers, the surface area of nonspherical nonmagnetic particles has an equivalent surface area of spherical nonmagnetic particles with ranges from 1 to 400 micrometers, and the surface of the nonmagnetic particles is smooth, rough, porous, or extended with attachments to other nonmagnetic particles; and
   (iv) no optically detectable tags are used for amplification, detection or quantification.

2. The structure of claim 1, wherein the nonmagnetic particle in claim 1 (c) is selected from the group consisting of styrene, polystyrene, polymer, agarose, glass, ceramic, composite material, and combinations thereof, and the first analyte binding material in claim 1 (a) and the second analyte binding material in claim 1 (c) are selected from the group consisting of antibodies, monoclonal antibodies, polyclonal antibodies, amino acids, peptides, proteins, haptens, nucleic acids, oligonucleotides, DNA, RNA, aptamers, matched pairs thereof and combinations thereof.

3. A device for amplifying, detecting and/or quantifying an analyte or multiple different analytes in a fluid sample, wherein said device consists of:
   (a) a magnetic separation unit configured to form a first outer layer and inner layer of signal amplification sandwich structures,
   (b) an analyte amplification unit configured to form a second outer layer of signal amplification sandwich structures,
   (c) a tag discharge unit configured to discharge electrochemically detectable oligonucleotide tags from signal amplification sandwich structures, and
   (d) an electrochemical detection unit with at least one biosensor working electrode configured to measure detection signals from the electrochemically detectable oligonucleotide tags,
   wherein said device employs the units from step (a), step (b), step (c) and step (d), collectively referred to as the device units, to form one or more signal amplification sandwich structures for amplifying detection signals from said analyte or multiple different analytes in a fluid sample, wherein said signal amplification sandwich structure consists of a first outer layer comprising a magnetic particle conjugated with a plurality of a first analyte binding material for binding said analyte, an inner layer comprising said analyte, and a second outer layer comprising a nonmagnetic particle conjugated with a plurality of a second analyte binding material for binding said analyte that is a matched pair with the first analyte binding material and the nonmagnetic particle is also conjugated on its outer structure or temporarily filled in its inner structure with a plurality of an electrochemically detectable oligonucleotide tag in greater amounts than said analyte from said inner layer,
   wherein:
   (i) said electrochemically detectable oligonucleotide tags are for signal amplification, wherein the majority of nucleotides within said oligonucleotide tags are guanine, wherein said nucleotides within said oligonucleotide tags are selected from the group consisting of guanine, adenine, and thymine, and wherein the combination of said nucleotides produces a unique oligonucleotide tag that is used to amplify, detect and/or quantify said analyte or multiple different analytes;

(ii) analyte amplification performance of said signal amplification sandwich structure can be tuned to meet the desired limit of detection by adjusting one or more of the following parameters: (a) the number of electrochemically detectable oligonucleotide tags per nonmagnetic particle; (b) the number of guanines per electrochemically detectable oligonucleotide tag; (c) the size of the nonmagnetic particle; and (d) the surface area of the nonmagnetic particle for conjugating electrochemically detectable oligonucleotide tags;

(iii) the number of electrochemically detectable oligonucleotide tags per nonmagnetic particle ranges from $10^2$ to $10^{13}$, the number of guanines per electrochemical detectable oligonucleotide tag ranges from 10 to 400, wherein the nonmagnetic particles are spherical and/or nonspherical, the diameter of spherical nonmagnetic particles ranges from 1 to 400 micrometers, the surface area of nonspherical nonmagnetic particles has an equivalent surface area of spherical nonmagnetic particles with ranges from 1 to 400 micrometers, and the surface of the nonmagnetic particles is smooth, rough, porous, or extended with attachments to other nonmagnetic particles; and (iv) no optically detectable tags are used for amplification, detection or quantification.

4. The device of claim 3, wherein the analyte amplification unit comprises one or more sets of nonmagnetic particles for creating electrochemically detectable oligonucleotide tag-nonmagnetic particle-analyte-magnetic particle structures if the analyte is present, wherein each set of nonmagnetic particles employs a plurality of a unique electrochemically detectable oligonucleotide tag for signal amplification, wherein the majority of the nucleotides within said oligonucleotide tags are guanine, wherein the nucleotides within the oligonucleotide tags are selected from the group consisting of guanine, adenine, and thymine, and wherein the combination of said nucleotides produces a unique oligonucleotide tag that is used to amplify, detect and/or quantify said analyte or multiple different analytes.

5. The device of claim 3, wherein the electrochemical detection unit consists of (a) an electrochemical biosensor or nanobiosensor comprising one or more working electrodes, wherein each working electrode is associated with said analyte from claim 3 that may be present in the sample and wherein each working electrode is conjugated with a plurality of an oligonucleotide recognition probe to bind or hybridize with associated electrochemically detectable oligonucleotide tags that is complementary to the oligonucleotide recognition probes, and (b) an electrochemical detection system that produces electrochemical signals on each working electrode in proportion to the quantity of said analyte if said analyte is present in the fluid sample, wherein the oligonucleotide recognition probes are oligonucleotides, wherein the majority of the nucleotides within said oligonucleotide recognition probes are cytosine, wherein the nucleotides within the oligonucleotide recognition probes are selected from the group consisting of cytosine, thymine, and adenine, wherein the combination of said nucleotides produces oligonucleotide recognition probes, and wherein each oligonucleotide recognition probe is complementary to a unique electrochemically detectable oligonucleotide tag defined in claim 3.

6. The device of claim 3, wherein the electrochemical detection unit produces a linear dynamic concentration range for quantifying the analyte in the fluid sample from known quantities of said analyte, and wherein said linear dynamic concentration range can be tuned by adjusting one or more of the following parameters: the size of the working electrode, the surface area of the working electrode, the number of oligonucleotide recognition probes per working electrode, and the amplification ratio of electrochemically detectable oligonucleotide tags per analyte.

7. The device of claim 3, wherein multiple different analytes can be measured simultaneously from the said fluid sample:

(i) as multiple different analytes measured individually at unique biosensor working electrodes associated with each different analyte wherein each said analyte is associated with (a) a unique magnetic particle conjugated with a plurality of a first analyte binding material that binds with said analyte; (b) a unique nonmagnetic particle conjugated with a plurality of a second analyte binding material that is a matched pair with the first analyte binding material and that binds with said analyte, and is also conjugated with a plurality of a unique electrochemically detectable oligonucleotide tag for signal amplification of said analyte, wherein the majority of the nucleotides within said oligonucleotide tags are guanine, wherein the nucleotides within the oligonucleotide tags are selected from the group consisting of guanine, adenine, and thymine, and wherein the combination of said nucleotides produces a unique oligonucleotide tag that is used to amplify, detect and/or quantify said analyte; and (c) a unique working electrode conjugated with a plurality of a unique oligonucleotide recognition probe to bind or hybridize with the complementary electrochemically detectable oligonucleotide tag of said analyte to determine the quantity of said analyte; or (ii) as multiple different analytes measured as a group at a common biosensor working electrode associated with any analyte in said group of multiple different analytes wherein each said analyte in said group is associated with (a) a unique magnetic particle conjugated with a plurality of a first analyte binding material that binds with said analyte, (b) a unique nonmagnetic particle conjugated with a plurality of a second analyte binding material that is a matched pair with the first analyte binding material for said analyte, and is also conjugated with a plurality of a common electrochemically detectable oligonucleotide tag for signal amplification of any said analyte in said group, wherein the majority of the nucleotides within said oligonucleotide tags are guanine, wherein the nucleotides within the oligonucleotide tags are selected from the group consisting of guanine, adenine, and thymine, and wherein the combination of said nucleotides produces a unique oligonucleotide tag that is used to amplify, detect and/or quantify any analyte in said group; and (c) a unique working electrode that is conjugated with a plurality of a unique oligonucleotide recognition probe to bind or hybridize with the common complementary electrochemically detectable guanine tag for any said analyte in said group to determine the combined quantity for all said analytes in said group.

8. The device of claim 3, wherein the electrochemical detection unit produces a linear dynamic concentration range for quantifying the analyte in the fluid sample from known quantities of said analyte in two or more standard samples, and wherein said linear dynamic concentration range can be increased in range by diluting a portion of one of the standard samples into a second standard sample, and diluting a portion of the second standard sample into a third standard sample, and diluting a portion of subsequent standard samples into derivative diluted standard samples.

9. The device of claim 3, wherein the device units in claim 3 are configured to comprise:
   (a) one or more consumable test cartridges comprising portions of the device units for processing one or more samples; and
   (b) a portable analyzer comprising portions of the device units for operating the one or more consumable test cartridges to process one or more samples.

10. The device of claim 9, wherein the one or more consumable test cartridges comprise one or more of microfluidics, a specimen inlet, sealable or nonsealable openings for magnetic particle and nonmagnetic particle solutions, reservoirs containing reagents, channels and mixing chambers, biosensors or nanobiosensors, heaters, magnet, valves, inlets for air connections, electrical connectors and circuitry for signal measurements and electrical systems, bar code, and Quick Response (QR) code.

11. The device of claim 9, wherein the one or more consumable test cartridges further provide one or more of dilution chambers, dilution reagents, and additional unique sets of working electrodes to create a larger linear dynamic concentration range for quantifying said analyte.

12. The device of claim 3, wherein the device units in claim 3 are configured to comprise:
   (a) one or more consumable high throughput test panels comprising portions of the device units for processing one or more samples; and
   (b) a high throughput analyzer comprising portions of the device units for operating the one or more consumable high throughput test panels to process one or more samples.

13. The device of claim 3, wherein the device units in claim 3 are configured to comprise:
   (a) one or more consumable test cartridges comprising portions of the device units for processing one or more samples;
   (b) an autonomous networked analyzer comprising portions of the device units for operating the one or more consumable test cartridges to process one or more samples;
   (c) a sample collection and concentration unit; and
   (d) a communications unit.

14. The device of claim 3, wherein the device units in claim 3 are configured to comprise:
   (a) one or more consumable development cartridges comprising portions of the device units for processing one or more samples, wherein each consumable development cartridge has openings for inserting conjugated magnetic particles and conjugated nonmagnetic particles;
   (b) a development analyzer comprising portions of the device units for operating the one or more consumable development cartridges to process one or more samples;
   (c) algorithms for measuring the effectiveness of analyte binding materials, tag elution, and tag-probe hybridization, algorithms for generating concentration curves, and algorithms for identifying information associated with specific consumable development cartridges; and
   (d) an insertion tool for inserting conjugated magnetic particles and conjugated nonmagnetic particles into the consumable development cartridges.

15. The device of claim 14, wherein the one or more consumable development cartridges comprise one or more of microfluidics, a specimen inlet, sealable or nonsealable openings for magnetic particle and nonmagnetic particle solutions, reservoirs containing reagents, channels and mixing chambers, biosensors or nanobiosensors, heaters, magnet, valves, inlets for air connections, electrical connectors and circuitry for signal measurements and electrical systems, bar code, and Quick Response (QR) code.

16. The device of claim 3, wherein the magnetic separation unit, the analyte amplification unit and the tag discharge unit in claim 3 are configured to comprise:
   (a) one or more consumable amplification cartridges comprising portions of the magnetic separation unit, the analyte amplification unit and the tag discharge unit for processing one or more samples; and
   (b) an amplification instrument comprising portions of the magnetic separation unit, the analyte amplification unit and the tag discharge unit for operating the one or more consumable amplification cartridges to process one or more samples.

17. A method for amplifying, detecting and/or quantifying an analyte or multiple different analytes in a fluid sample, wherein said method consists of the following steps performed sequentially:
   (a) providing the fluid sample that may contain non-specific materials and an analyte or multiple different analytes;
   (b) providing one or more sets of magnetic particles, wherein each set comprises a plurality of a magnetic particle conjugated with a plurality of a first analyte binding material to create analyte-magnetic particle complexes if said analyte or said multiple different analytes are present;
   (c) providing one or more sets of nonmagnetic particles, wherein each set comprises a plurality of a nonmagnetic particle conjugated with a plurality of a second analyte binding material that is a matched pair with the first analyte binding material and is also conjugated with a plurality of a second electrochemically detectable oligonucleotide tag in greater amounts than said analyte to create electrochemically detectable oligonucleotide tag-nonmagnetic particle-analyte-magnetic particle structures if said analyte is present; and
   (d) providing one or more working electrodes, wherein each working electrode is associated with said analyte or said group of multiple different analytes that may be present in said sample and wherein each working electrode is conjugated with a plurality of an oligonucleotide recognition probe to bind with associated electrochemically detectable oligonucleotide tags, and an electrochemical detection technique produces electrochemical signals on each working electrode in proportion to the quantity of said analyte or said group of multiple different analytes if said analyte or said group of multiple different analytes is present in the fluid sample;
   wherein said method employs one or more signal amplification sandwich structures for amplifying detection signals from the analyte or multiple different analytes in the fluid sample, wherein said structure consists of a first outer layer comprising a magnetic particle conjugated with a plurality of a first analyte binding material for binding said analyte, an inner layer comprising said analyte, and a second outer layer comprising a nonmagnetic particle conjugated with a plurality of a second analyte binding material for binding said analyte that is a matched pair with the first analyte binding material and the nonmagnetic particle is also conjugated on its outer structure or temporarily filled in its inner structure with a plurality of an electrochemically detectable oligonucleotide tag in greater amounts than said analyte from said inner layer, wherein:

(i) said electrochemically detectable oligonucleotide tags are for signal amplification, wherein the majority of nucleotides within said oligonucleotide tags are guanine, wherein said nucleotides within said oligonucleotide tags are selected from the group consisting of guanine, adenine, and thymine, and wherein the combination of said nucleotides produces a unique oligonucleotide tag that is used to amplify, detect and/or quantify said analyte or said group of multiple different analytes;

(ii) analyte amplification performance of said signal amplification sandwich structure can be tuned to meet the desired limit of detection by adjusting one or more of the following parameters: (a) the number of electrochemically detectable oligonucleotide tags per nonmagnetic particle; (b) the number of guanines per electrochemically detectable oligonucleotide tag; (c) the size of the nonmagnetic particle; and (d) the surface area of the nonmagnetic particle for conjugating electrochemically detectable oligonucleotide tags;

(iii) the number of electrochemically detectable oligonucleotide tags per nonmagnetic particle ranges from $10^2$ to $10^{13}$, the number of guanines per electrochemical detectable oligonucleotide tag ranges from 10 to 400, wherein the nonmagnetic particles are spherical and/or nonspherical, the diameter of spherical nonmagnetic particles ranges from 1 to 400 micrometers, the surface area of nonspherical nonmagnetic particles has an equivalent surface area of spherical nonmagnetic particles with ranges from 1 to 400 micrometers, and the surface of the nonmagnetic particles is smooth, rough, porous, or extended with attachments to other nonmagnetic particles; and (iv) no optically detectable tags are used for amplification, detection or quantification.

18. The method of claim 17, wherein the electrochemical detection technique in step (d) performs a first, a second and a third amperometric detection scan with an electron transport mediator on each working electrode, whereby (e) the generated signal from guanine oxidation is measured as the difference in peak signal from a first scan minus peak signal from a second scan;

(f) said analyte is determined to be present if the generated signal from the associated electrochemically detectable oligonucleotide tags in step (e) is greater than the greatest variation in signal from a second scan minus a third scan; and (g) the quantity of said analyte is determined by comparing the generated electrochemical signal from an associated electrochemically detectable oligonucleotide tag in step (e) with predetermined signals from known quantities of said analyte.

19. The method of claim 17, wherein said method further comprises:

(h) the analyte-magnetic particle complexes in step (b) are magnetically immobilized and the non-magnetically immobilized constituents of the fluid sample which may contain non-specific materials is washed and flushed away;

(i) the electrochemically detectable oligonucleotide tag-nonmagnetic particle-analyte-magnetic particle structures in step (c) are magnetically immobilized and unbound nonmagnetic particles conjugated with electrochemically detectable oligonucleotide tags are washed and flushed away;

(j) after step (c) the electrochemically detectable oligonucleotide tag-nonmagnetic particle-analyte-magnetic particle structures are magnetically immobilized and electrochemically detectable oligonucleotide tags are unbound from said structures, and washed and delivered to the working electrodes in step (d); and (k) after step (a) the fluid sample may optionally be treated by one or more of the following: a membrane, a chemical adherent, a disaggregation technique involving one or more of a chemical surfactant, sonication, and hydrodynamic cavitation to disaggregate clumps potentially containing said analytes, and a dilution technique to provide multiple concentrations of samples that can be separately processed as a larger range to quantify said analyte.

20. A method for amplifying an analyte or multiple different analytes in a fluid sample, wherein said method consists of the following steps performed sequentially:

(a) providing the fluid sample that may contain non-specific materials and an analyte or multiple different analytes;

(b) providing one or more sets of magnetic particles, wherein each set comprises a plurality of a magnetic particle conjugated with a plurality of a first analyte binding material to create analyte-magnetic particle complexes if said analyte or said multiple different analytes are present;

(c) providing one or more sets of nonmagnetic particles, wherein each set comprises a plurality of a nonmagnetic particle conjugated with a plurality of a second analyte binding material that is a matched pair with a first analyte binding material and is also conjugated with a plurality of a second electrochemically detectable oligonucleotide tag in greater amounts than said analyte to create electrochemically detectable oligonucleotide tag-nonmagnetic particle-analyte-magnetic particle structures if said analyte is present; and (d) said electrochemically detectable oligonucleotide tag-nonmagnetic particle-analyte-magnetic particle structures are magnetically immobilized and said electrochemically detectable oligonucleotide tags are unbound from said structures, and washed and delivered as electrochemically detectable oligonucleotide tags for amplifying detection signals from said analytes in said fluid sample, wherein said method employs one or more signal amplification sandwich structures for amplifying detection signals from the analyte or multiple different analytes in the fluid sample, wherein said structure consists of a first outer layer comprising a magnetic particle conjugated with a plurality of a first analyte binding material for binding said analyte, an inner layer comprising said analyte, and a second outer layer comprising a non-magnetic particle conjugated with a plurality of a second analyte binding material for binding said analyte that is a matched pair with the first analyte binding material and the nonmagnetic particle is also conjugated on its outer structure or temporarily filled in its inner structure with a plurality of an electrochemically detectable oligonucleotide tag in greater amounts than said analyte from said inner layer, wherein:

(i) said electrochemically detectable oligonucleotide tags are for signal amplification, wherein the majority of nucleotides within said oligonucleotide tags are guanine, wherein said nucleotides within said oligonucleotide tags are selected from the group consisting of guanine, adenine, and thymine, and wherein the combination of said nucleotides produces a unique oligonucleotide tag that is used to amplify said analyte or a group of multiple different analytes;

(ii) analyte amplification performance of said signal amplification sandwich structure can be tuned to meet the desired limit of detection by adjusting one or more of the following parameters: (a) the number of electrochemically detectable oligonucleotide tags per nonmagnetic particle; (b) the number of guanines per electrochemically detectable oligonucleotide tag; (c) the size of the nonmagnetic particle; and (d) the surface area of the nonmagnetic particle for conjugating electrochemically detectable oligonucleotide tags;

(iii) the number of electrochemically detectable oligonucleotide tags per nonmagnetic particle ranges from $10^2$ to $10^{13}$, the number of guanines per electrochemical detectable oligonucleotide tag ranges from 10 to 400, wherein the nonmagnetic particles are spherical and/or nonspherical, the diameter of spherical nonmagnetic particles ranges from 1 to 400 micrometers, the surface area of nonspherical nonmagnetic particles has an equivalent surface area of spherical nonmagnetic particles with ranges from 1 to 400 micrometers, and the surface of the nonmagnetic particles is smooth, rough, porous, or extended with attachments to other nonmagnetic particles; and (iv) no optically detectable tags are used for amplification.

* * * * *

SEQUENCE LISTING

<160> NUMBER OF SEQ ID NOS: 8

<210> SEQ ID NO 1
<211> LENGTH: 38
<212> TYPE: DNA
<213> ORGANISM: Artificial Sequence
<220> FEATURE:
<223> OTHER INFORMATION: Synthesized oligonucleotide, rich in
      electrochemically detectable guanine, to act as a tag for
      amplifying analyte detection signals

<400> SEQUENCE: 1
gggggggggg gggggggggg gggggggggg ggggggg                           38

<210> SEQ ID NO 2
<211> LENGTH: 38
<212> TYPE: DNA
<213> ORGANISM: Artificial Sequence
<220> FEATURE:
<223> OTHER INFORMATION: Synthesized oligonucleotide, rich in cytosine,
      to act as a probe for hybridizing complementary oligonucleotide amplification tag rich in guanine

<400> SEQUENCE: 2
cccccccccc cccccccccc cccccccccc ccccccc                              38

<210> SEQ ID NO 3
<211> LENGTH: 40
<212> TYPE: DNA
<213> ORGANISM: Artificial Sequence
<220> FEATURE:
<223> OTHER INFORMATION: Synthesized oligonucleotide, rich in
      electrochemically detectable guanine, to act as a tag for
      amplifying analyte detection signals

<400> SEQUENCE: 3
gggaaaggga gggaaagaaa gggaaaggga gggaaagaaa                           40

<210> SEQ ID NO 4
<211> LENGTH: 40
<212> TYPE: DNA
<213> ORGANISM: Artificial Sequence
<220> FEATURE:
<223> OTHER INFORMATION: Synthesized oligonucleotide, rich in cytosine,
      to act as a probe for hybridizing complementary oligonucleotide
      amplification tag rich in guanine

<400> SEQUENCE: 4 cccttccct ccctttcttt ccctttccct ccctttcttt                            40

<210> SEQ ID NO 5
<211> LENGTH: 40
<212> TYPE: DNA
<213> ORGANISM: Artificial Sequence
<220> FEATURE:
<223> OTHER INFORMATION: Synthesized oligonucleotide, rich in
      electrochemically detectable guanine, to act as a tag for
      amplifying analyte detection signals

<400> SEQUENCE: 5
gggattggga gggattgatt gggattggga gggattgatt                           40

<210> SEQ ID NO 6
<211> LENGTH: 40
<212> TYPE: DNA
<213> ORGANISM: Artificial Sequence
<220> FEATURE:
<223> OTHER INFORMATION: Synthesized oligonucleotide, rich in cytosine,
      to act as a probe for hybridizing complementary oligonucleotide
      amplification tag rich in guanine

<400> SEQUENCE: 6
ccctaaccct ccctaactaa ccctaaccct ccctaactaa                           40

<210> SEQ ID NO 7
<211> LENGTH: 30
<212> TYPE: DNA
<213> ORGANISM: Artificial Sequence
<220> FEATURE:
<223> OTHER INFORMATION: Synthesized oligonucleotide, rich in
      electrochemically detectable guanine, to act as a tag for
      amplifying analyte detection signals

<400> SEQUENCE: 7
gtgggtgggt aaggagtgag ggtgggagtt                                      30

<210> SEQ ID NO 8
<211> LENGTH: 30

```
<212> TYPE: DNA
<213> ORGANISM: Artificial Sequence
<220> FEATURE:
<223> OTHER INFORMATION: Synthesized oligonucleotide, rich in cytosine,
      to act as a probe for hybridizing complementary oligonucleotide
      amplification tag rich in guanine

<400> SEQUENCE: 8
cacccaccca ttcctcactc ccaccctcaa                                              30
```